(12) United States Patent
Mita et al.

(10) Patent No.: US 8,354,529 B2
(45) Date of Patent: Jan. 15, 2013

(54) POLYAMINE DERIVATIVE AND POLYOL DERIVATIVE

(75) Inventors: Naruyoshi Mita, Sodegaura (JP); Mitsuaki Chida, Sodegaura (JP); Masaru Kawaguchi, Omuta (JP); Kengo Otsuka, Sodegaura (JP); Naoshi Nagai, Sodegaura (JP); Takaaki Yamazaki, Tokyo (JP); Tetsuya Ichihashi, Fujimi (JP)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/289,013

(22) Filed: Nov. 4, 2011

(65) Prior Publication Data

US 2012/0053270 A1    Mar. 1, 2012

Related U.S. Application Data

(63) Continuation of application No. 11/795,216, filed as application No. PCT/JP2006/000607 on Jan. 18, 2006, now Pat. No. 8,076,478.

(30) Foreign Application Priority Data

Jan. 21, 2005    (JP) .................. 2005-013663

(51) Int. Cl.
*C07D 401/14* (2006.01)
*C08K 5/3492* (2006.01)
*C08L 101/00* (2006.01)
*C09K 15/30* (2006.01)

(52) U.S. Cl. ........ 544/198; 544/209; 524/100; 252/405; 252/401; 252/407

(58) Field of Classification Search .................. 544/198, 544/209; 524/100; 252/405
See application file for complete search history.

(56) References Cited

U.S. PATENT DOCUMENTS

| | | | | |
|---|---|---|---|---|
| 4,263,434 A | 4/1981 | Cassandrini et al. | ......... | 544/198 |
| 4,288,593 A | 9/1981 | Rody | ................. | 4/198 |
| 4,322,337 A | 3/1982 | Rody | ................. | 4/100 |
| 4,496,726 A | 1/1985 | Wiezer et al. | ................. | 544/198 |
| 4,533,688 A | 8/1985 | Toda et al. | ................. | 524/100 |
| 5,130,429 A | 7/1992 | Piccinelli et al. | ............. | 544/212 |
| 5,134,181 A | 7/1992 | Masina | ......... | 524/100 |
| 8,076,478 B2 * | 12/2011 | Mita et al. | .................. | 544/198 |

FOREIGN PATENT DOCUMENTS

| | | |
|---|---|---|
| BE | 904401 | 6/1986 |
| EP | 0399953 A2 | 11/1990 |
| EP | 0468923 | 1/1992 |
| JP | 05-043745 | 2/1993 |

OTHER PUBLICATIONS

Derwent Abstract 92-028947/04 for JP 3-275746, (Dec. 1991).
Derwent Abstract 93-061760/08 for JP 5-009356, (Jan. 1993).
Patent Abstracts of Japan Publication No. 05-043745, (Feb. 1993).
English Language Abstract for IT 1200450, (Jan. 1989) which is equivalent to BE 904401, (Jun. 1986).
English Language Abstract for JP 8048888, (Feb. 1996).
English Language Abstract for JP 6263929, (Sep. 1994).

\* cited by examiner

*Primary Examiner* — Venkataraman Balasubramanian
(74) *Attorney, Agent, or Firm* — Tyler A. Stevenson

(57) ABSTRACT

A novel polyamine derivative, or polyol derivative, having a piperidylaminotriazine skeleton; salts of such compounds; a process for producing them; an organic material stabilizer comprising any of such compounds; a method of stabilizing an organic material; and a stabilized organinc material. Compounds of the general formula: (1) (wherein X is $N(R^4)$ or an oxygen atom; $R^1$ is an n-valent hydrocarbon group; $R^2$ is an hydrogen atom or an alkyl; $R^3$ is a hydrogen atom, an alkyl, an alkoxy or an acyl; $R^4$ is a hydrogen atom or an alkyl; and n is an integer of 3 to 16) are effective in the stabilization of an organic material against deterioration by light, heat, oxygen, ozone and electromagnetic waves, such as X-rays and γ-rays.

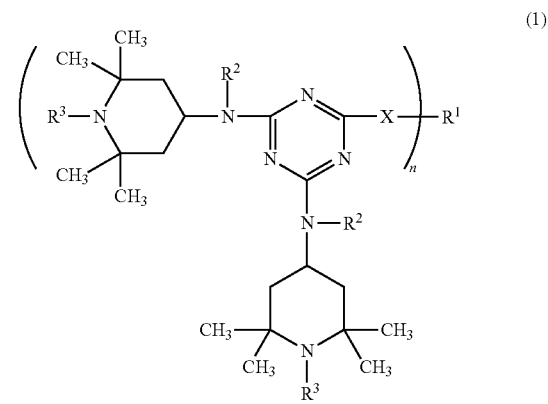

7 Claims, No Drawings

POLYAMINE DERIVATIVE AND POLYOL DERIVATIVE

This application is a continuation of U.S. application Ser. No. 11/795,216, filed Feb. 21, 2008 now U.S. Pat. No. 8,076,478, which is a 371 of PCT/JP2006/300607, filed Jan. 18, 2006, the contents of which are incorporated by reference.

TECHNICAL FIELD

The present invention relates to a polyamine derivative and a polyol derivative having a novel piperidylaminotriazine skeleton and a preparation process thereof. Further, the present invention relates to a stabilizer for an organic material comprising the compound, a stabilization method for the organic material by the compound and the organic material stabilized by the method.

BACKGROUND ART

Organic materials, particularly polymer materials including polypropylene are light weight and high in shape freedom and are widely used for applications in which weather resistance is required in the range from automobile-related usage to building material-related usage, agricultural film usage and household electric article-related usage. A substance which imparts weather resistance to these polymer materials is a light stabilizer and among them, a hindered amine based light stabilizer (HALS: Hindered Amine Light Stabilizer) is usually used as an indispensable resin additive at present.

The existing HALS is classified broadly into a low molecular weight type compound having a molecular weight of 1000 or less and a high molecular weigh type compound having a molecular weight of 1500 or more and by separate usage or usage in combination of these compounds, in the usage of both thin articles (the thin layer-like polymer material) and thick articles (the polymer material other than the thin article), stabilization relative to light is intended. However, in the low molecular type compounds, it is difficult to continuously impart a stabilization effect in the thin article usage. Further, there is a problem of bleeding out, fogging, sick house or the like originated in the low molecular weight type compounds. Whereas, in the high molecular weight type compounds, the stabilization effect is small in the thick article usage and it is further known that pigment dispersibility is also insufficient. Further, even in combination usage of compounds of both types, an additive/synergistic effect is not generally recognized. Further, in both low molecular weight type compounds and high molecular weight compounds, it is recognized to contaminate a metal die at molding and there is a problem in that increase in the number of cleaning of the metal causes reduction in productivity.

In the polyamine derivative having the piperidylaminotriazine skeleton, as the compound in which all amino groups derived from the polyamine main skeleton linked to the triazine ring are linked to only one methylene group in the polyamine main skeleton respectively of the compound having 3 or more triazine rings, there are compounds described in Patent Document 1 and compounds disclosed in very wide Marcush structure of Patent Documents 2 to 8. Further, in the polyol derivative having the piperidylaminotriazine skeleton, as the compound in which the polyol main skeleton is a hydrocarbon group of the compound having 3 or more triazine rings, there are compounds disclosed in very wide Marcush structure of Patent Documents 2 and 7. However, these compounds involve problems described above or problems of difficulty in obtaining the raw material for production and problems of production process such as extended production step (including a production step of polyamine and polyol, i.e., intermediates).

Patent Document 1: Japanese Unexamined Patent Publication No. Sho 59-122487
Patent Document 2: Japanese Unexamined Patent Publication No. Sho 52-73886
Patent Document 3: Japanese Unexamined Patent Publication No. Sho 63-286448
Patent Document 4: Japanese Unexamined Patent Publication No. Hei 1-190678
Patent Document 5: Japanese Unexamined Patent Publication No. Hei 3-275746
Patent Document 6: Japanese Unexamined Patent Publication No. Hei 5-9356
Patent Document 7: EP Unexamined Patent Publication No. 468923 Specification
Patent Document 8: Japanese Unexamined Patent Publication No. Hei 5-43745

DISCLOSURE OF THE INVENTION

Problem to be Solved by the Invention

It is an object of the present invention to provide a compound as a novel HALS in which light stability is imparted to organic materials of both thin articles and thick articles, and which compound causes no problem of bleeding out, fogging, sick house, pigment low dispersibility, contamination of a metal die at molding or the like and can be produced easily. It is also an object of the present invention to provide a preparation process of the compound, a stabilizer for organic materials comprising the compound, a stabilization method of the organic materials using the compound and stabilized organic materials.

Means for Solving the Problem

The present inventors made intensive studies to attain the above objects, and as a result, they have found polyamine derivatives and polyol derivative having a novel piperidylaminotriazine skeleton and further have found a preparation process thereof, a stabilizer for the organic material comprising the compound, a stabilization method of organic materials using the compound and organic materials stabilized by the method, thereby leading to completion of the present invention.

Namely, according to the present invention, a compound represented by general formula (1):

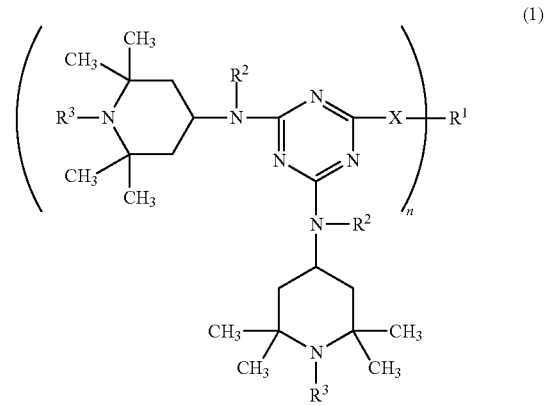

(wherein X represents $N(R^4)$ or an oxygen atom, $R^1$ represents an n-valent hydrocarbon group (provided that in cases where X is N(R$^4$), a nitrogen atom or an oxygen atom may be contained in the hydrocarbon group R$^1$, and the following formula (1-2) is excluded), R$^2$ represents a hydrogen atom or an alkyl group having from 1 to 9 carbon atoms, R$^3$ represents a hydrogen atom, an alkyl group having from 1 to 9 carbon atoms, an alkoxy group having from 1 to 9 carbon atoms or an acyl group having from 2 to 9 carbon atoms, R$^4$ represents a hydrogen atom or an alkyl group having from 1 to 9 carbon atoms and n represents an integer of from 3 to 16) or its salt is provided.

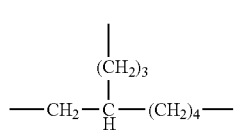

(1-2)

Further, according to the present invention, a preparation process of the compound represented by the general formula (1):

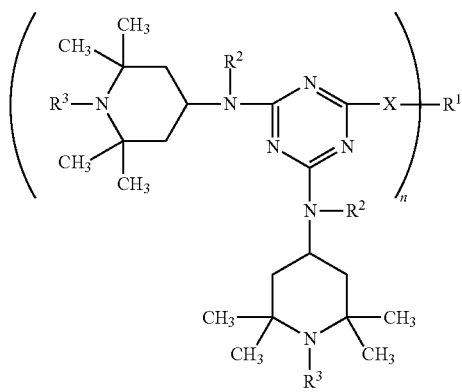

(1)

comprising coupling a compound represented by general formula (6-1):

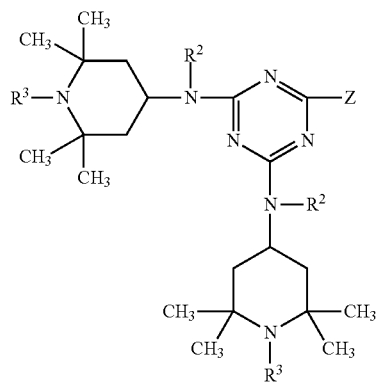

(6-1)

(wherein R$^2$ and R$^3$ have the same meanings as defined in the general formula (1) and Z represents a halogen atom) with a compound represented by general formula (6-2):

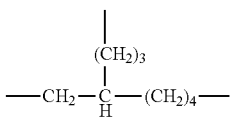

(6-2)

(wherein X, R$^1$ and n have the same meanings as defined in the general formula (1)). is provided.

Further, according to the present invention, a stabilizer for the organic material containing at least one of the compound represented by the general formula (1) or its salt; a use method of the compound represented by the general formula (1) or its salt for stabilizing the organic material for deterioration by light, heat, oxygen, ozone and an electromagnetic wave such as X ray and γ ray; and the organic material composition in which at least one of the compound represented by the general formula (1) or its salt is added in an amount of 0.001 to 15 parts by weight to 100 parts by weight of the organic material are provided.

EFFECT OF THE INVENTION

Although the polyamine derivative and the polyol derivative having the piperidylaminotriazine skeleton of the present invention are the HALS classified into the high molecular weight type compound having a molecular weight of 1500 or more, they effectively impart the light stability to the organic material of both thin articles and thick articles. Further, they do not cause the problems of bleeding out, fogging, sick house, pigment low dispersibility, contamination of the metal die at molding or the like. Further, the compound of the present invention can be produced easily. The compound prevents deterioration by the light, heat, oxygen, ozone and the electromagnetic wave such as X ray and γ ray and can stabilize the organic materials.

BEST MODE FOR CARRYING OUT THE INVENTION

In the following, the present invention is explained in detail.

The polyamine derivative and the polyol derivative having a novel piperidylaminotriazine skeleton of the present invention are represented by the general formula (1).

In the general formula (1) and the general formula (6-2), the n-valent hydrocarbon group represented by R$^1$ includes a straight, branched or cyclic group. The hydrocarbon group represented by R$^1$ is usually a group having from 3 to 100 carbon atoms, preferably from 3 to 50 carbon atoms. An aliphatic cyclic hydrocarbon group and/or an aromatic hydrocarbon group may be included in R$^1$. Further, in cases where X is N(R$^4$), a nitrogen atom or an oxygen atom may be included in R$^1$ but the following formula (1-2) is excluded.

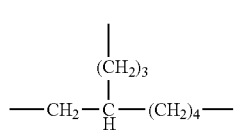

(1-2)

n represents an integer of from 3 to 16, preferably 3, 4 or 8, and particularly preferably 3 or 4.

As a group represented by R$^1$, in cases where X is N(R$^4$), a group represented by general formula (2-1):

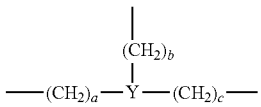

(2-1)

or general formula (2-2):

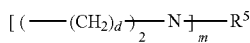
(2-2)

is preferable.

In the general formula (2-1), Y represents CH or a nitrogen atom and a, b, c each independently represent an integer of from 1 to 6. However, when Y is CH, the case where a, b, c are simultaneously a=1, b=3 and c=4 is excluded. Preferably, a, b, c each independently represent an integer of from 1 to 4, and in cases where Y is CH, the case where a, b, c are simultaneously a=b=3 and c=1 is most preferably and in cases where Y is a nitrogen atom, the case where a, b, c are simultaneously a=b=c=2 or a=b=c=3 is most preferably.

In the general formula (2-2), $R^5$ represents an m-valent hydrocarbon group. The m-valent hydrocarbon group of $R^5$ includes a straight, branched or cyclic group and preferably has from 2 to 100 carbon atoms, preferably from 2 to 50 carbon atoms. At least one group selected from the aliphatic cyclic hydrocarbon group or the aromatic hydrocarbon group may be included in $R^5$. At least one atom selected from the nitrogen atom or the oxygen atom may be further included in $R^5$.

m represents an integer of from 2 to 8, preferably 2 or 4, more preferably 2.

When m is 2, the divalent hydrocarbon group represented by $R^5$ is particularly preferably a group having from 2 to 20 carbon atoms. In cases where $R^5$ is a straight hydrocarbon group, the preferable group can include an ethylene group, a trimethylene group, a tetramethylene group, a pentamethylene group, a hexamethylene group, a heptamethylene group, an octamethylene group, a nonamethylene group, a decamethylene group, an undecanemethylene group and a dodecamethylene group. Among them, the ethylene group, the trimethylene group, the tetramethylene group, the pentamethylene group and the hexamethylene group are particularly preferably groups. In cases where $R^5$ represents a branched hydrocarbon group, it can include a 1-methylethylene group, in cases where $R^5$ represents a hydrocarbon group including an aliphatic cyclic hydrocarbon group, it can include a group represented by formula (7-1) or (7-2) and in cases where $R^5$ represents a hydrocarbon group including an aromatic hydrocarbon group, it can include a group represented by formula (7-3) or (7-4). Further, the group containing a nitrogen atom can include a group represented by formula (7-5) and the group containing an oxygen atom can include a group represented by formula (7-6).

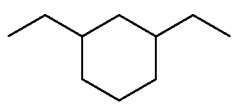
(7-1)

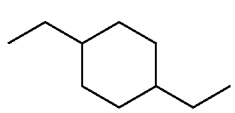
(7-2)

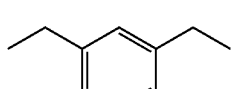
(7-3)

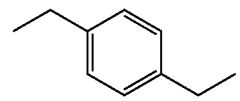
(7-4)

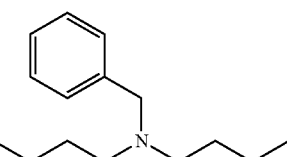
(7-5)

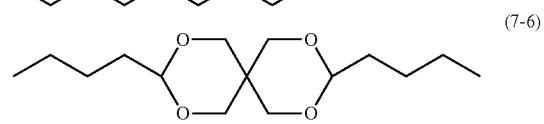
(7-6)

d represents an integer of from 1 to 6, preferably from 1 to 4, more preferably 2 or 3, and most preferably 3.

In cases where X is $N(R^4)$, as a group represented by

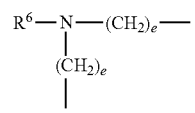
(3-1)

(wherein $R^6$ represents general formula (3-2) or (3-3))

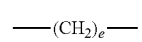
(3-2)

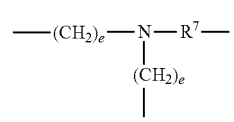
(3-3)

is also preferable.

In the general formulae (3-1), (3-2) and (3-3), e represents 2 or 3, and preferably 3.

In the general formula (3-3), $R^7$ represents a divalent hydrocarbon group. Further, $R^7$ is linked to a nitrogen atom in the general formula (3-1).

The divalent hydrocarbon group represented by $R^7$ includes a straight, branched or cyclic group, and preferably a group having from 2 to 30 carbon atoms. At least one group selected from an aliphatic cyclic hydrocarbon group or an aromatic hydrocarbon group may be contained in $R^7$. Further, at least one atom selected from a nitrogen atom or an oxygen atom may be contained in $R^7$. In cases where $R^7$ represents a straight hydrocarbon group, more preferable group can include an ethylene group, a trimethylene group, a tetramethylene group, a pentamethylene group, a hexamethylene group, a heptamethylene group, an octamethylene group, a nonamethylene group, a decamethylene group, an undecamethylene group and a dodecamethylene group. Among them, the ethylene group, the trimethylene group, the tetramethylene group, the pentamethylene group and the hexamethylene group are particularly preferable groups. In cases where $R^7$ represents a branched hydrocarbon group, it can include a 1-methylethylene group, in cases where $R^7$ represents a hydrocarbon group including an aliphatic cyclic hydrocarbon group, it can include a group represented by the formula (7-1) or (7-2) and in cases where $R^7$ represents a hydrocarbon group including an aromatic hydrocarbon group, it can include a group represented by the formula (7-3) or (7-4). Further, the group containing a nitrogen atom can include the group represented by the formula (7-5) and the group containing an oxygen atom can include the group represented by the formula (7-6).

In cases where X is an oxygen atom, as a group represented by $R^1$, the group represented by general formula (4):

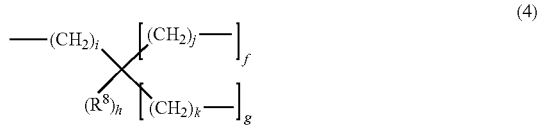

(4)

is preferred.

In the general formula (4), f represents an integer of from 0 to 4, preferably from 0 to 3, g represents an integer of from 0 to 3, preferably from 0 to 2 and h represents 0 or 1. Provided that a relationship of f+g+h=3 is established for f, g and h. i, j and k each independently represent an integer of from 0 to 9, preferably each independently represent an integer of from 0 to 5. Further, the case where i, j and k are 0 means a direct link by a single bond.

The alkyl group having from 1 to 9 carbon atoms of $R^2$ and $R^3$ in the general formulae (1) and (6-1), $R^4$ in the general formulae (1) and (6-2) and $R^8$ in the general formula (4) includes straight, branched and cyclic groups and can include a methyl group, an ethyl group, a n-propyl group, an isopropyl group, a n-butyl group, an isobutyl group, a sec-butyl group, a tert-butyl group, a pentyl group, a hexyl group, a heptyl group, an octyl group, a nonyl group, a cyclopentyl group, a cyclohexyl group and a cycloheptyl group.

The alkoxy group having from 1 to 9 carbon atoms of $R^3$ includes straight, branched and cyclic groups and can include a methoxy group, an ethoxy group, a n-propoxy group, an isopropoxy group, a n-butoxy group, an isobutoxy group, a sec-butoxy group, a tert-butoxy group, a pentyloxy group, a hexyloxy group, a heptyloxy group, an octyloxy group, a nonyloxy group, a cyclopentyloxy group, a cyclohexyloxy group and a cycloheptyloxy group.

The acyl group having from 2 to 9 carbon atoms of $R^3$ includes straight, branched and cyclic groups and can include an acetyl group, a propionyl group, a butyryl group, an isobutyryl group, a valeryl group, an isovaleryl group, a pivaloyl group, an acryloyl group, a propioloyl group, a methacryloyl group, a crotonoyl group and a benzoyl group.

The arylalkyl group having from 7 to 12 of $R^8$ can include a benzyl group, a phenethyl group or the like.

As $R^2$, an alkyl group having from 2 to 6 carbon atoms is particularly preferable and a n-butyl group is most preferable.

As $R^3$, a hydrogen atom, an alkyl group having from 1 to 4 carbon atoms, an alkoxy group having from 1 to 8 carbon atoms and an acetyl group are preferable and a hydrogen atom and a methyl group are most preferable.

As $R^4$, a hydrogen atom and an alkyl group having from 1 to 4 carbon atoms are preferable, a hydrogen atom and a methyl group are more preferable and a hydrogen atom is most preferable.

As $R^8$, a hydrogen atom and an alkyl group having from 1 to 4 carbon atoms are preferable and a hydrogen atom, a methyl group and an ethyl group are most preferable.

In the general formula (6-1), the halogen atom of Z can include a fluorine atom, a chlorine atom, a bromine atom and an iodine atom.

The salt of the compound represented by the general formula (1) of the present invention includes a salt with an inorganic acid or organic acid. The inorganic acid in this case can include hydrochloric acid, hydrobromic acid, hydroiodic acid, sulfuric acid, carbonic acid, phosphoric acid or the like. Further, the organic acid may be any one of an optically active organic acid and an optically inactive organic acid and can include carboxylic acids such as formic acid, acetic acid, propionic acid, benzoic acid, trifluoroacetic acid, tartaric acid and mandelic acid; sulfonic acids such as methanesulfonic acid, ethanesulfonic acid, benzenesulfonic acid and p-toluenesulfonic acid; amino acids; and its derivative. A composition ratio of the compound of the present invention and an acid in the salt may be equivalent or an arbitrary value.

The compound represented by the general formula (1) can include the compound of the formulae (5-1) to (5-34) but the compound is not limited to these as a matter of course.

(5-1)

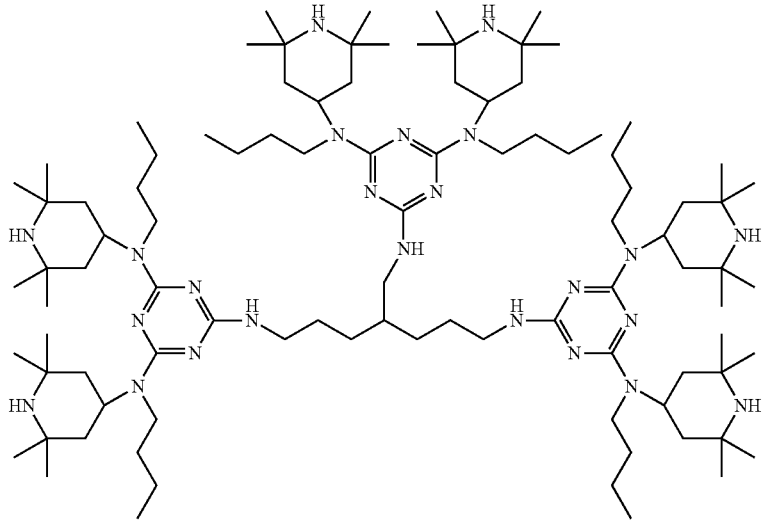

(5-2)
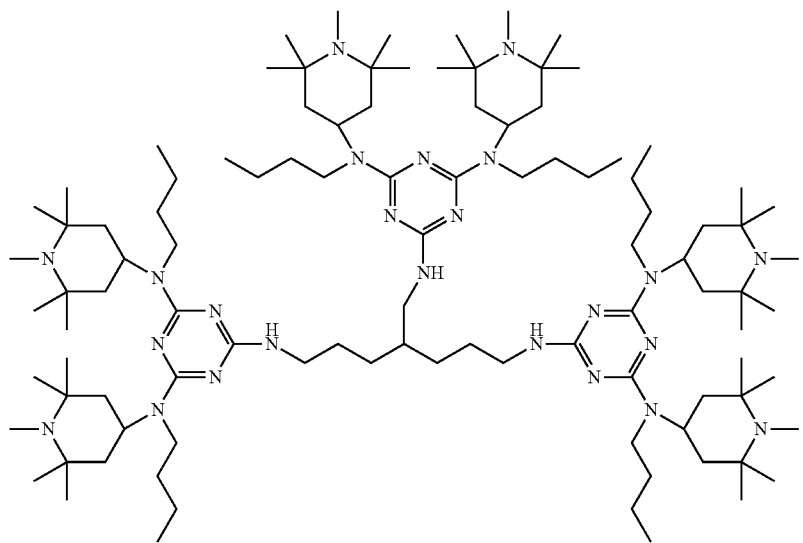
(5-3)
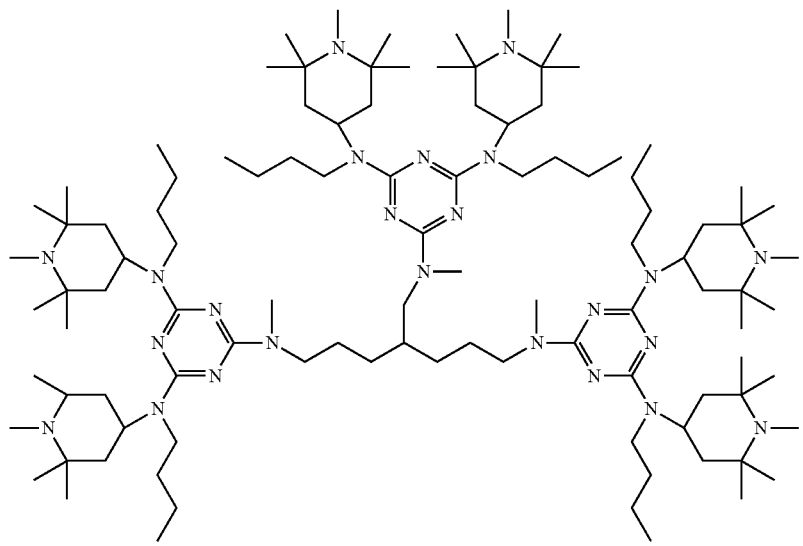
(5-4)
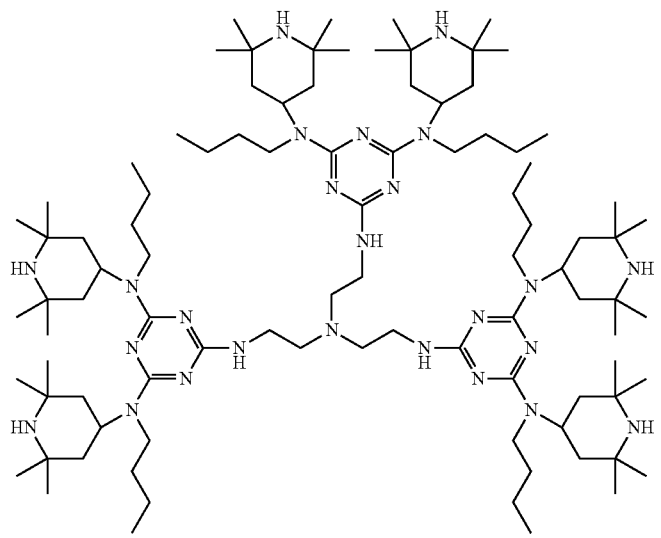

-continued
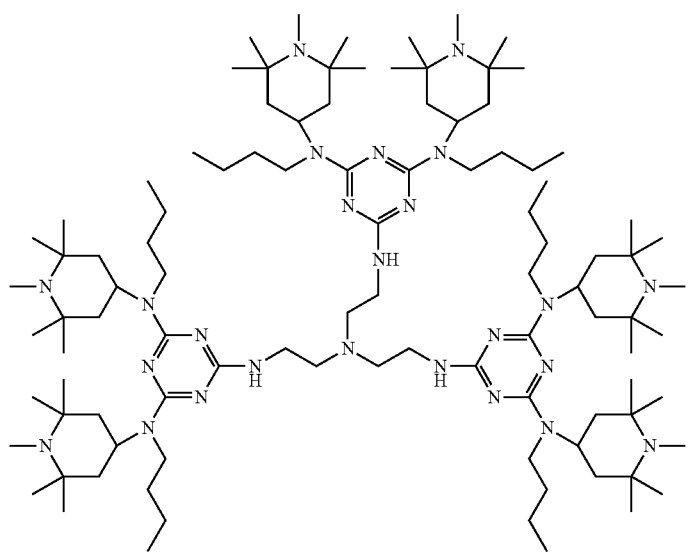
(5-5)
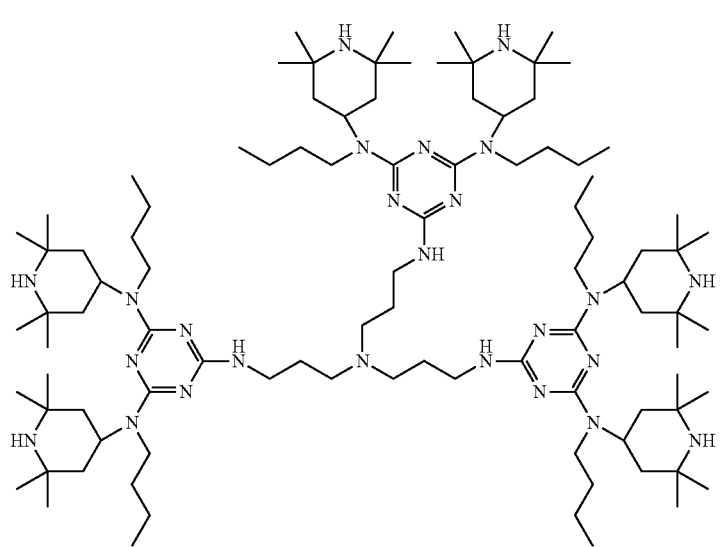
(5-6)
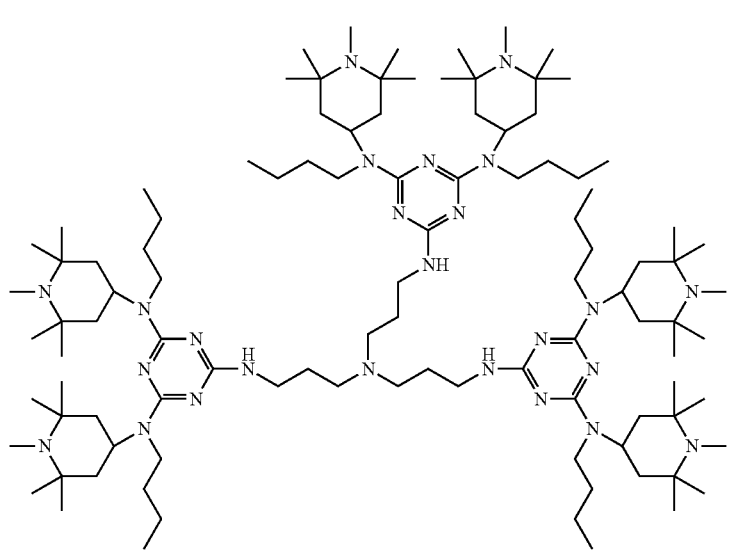
(5-7)

(5-8)
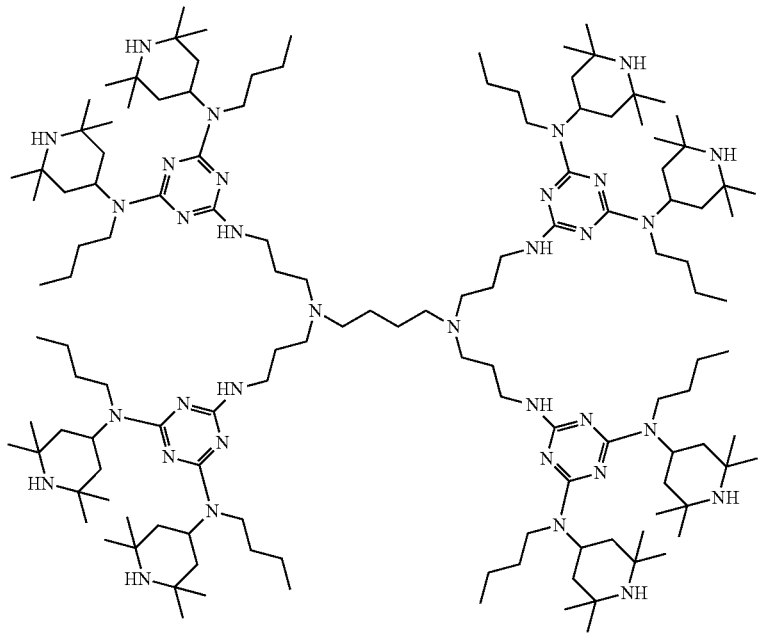
(5-9)
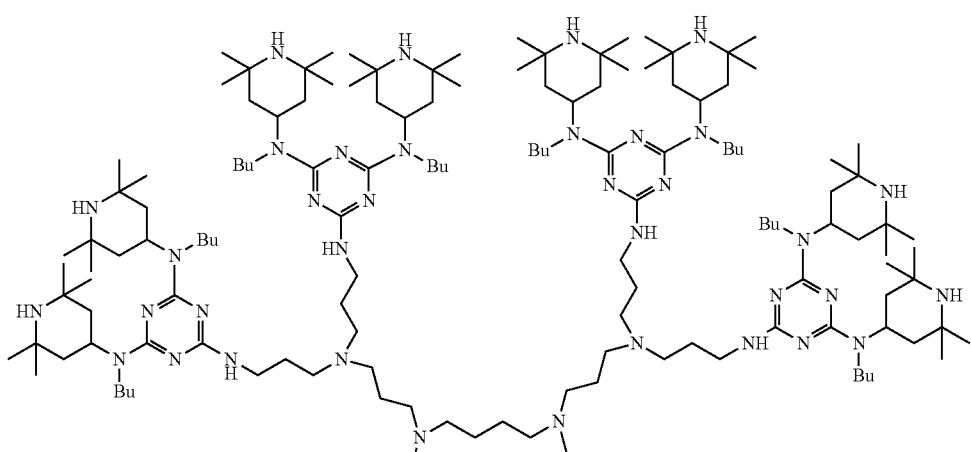
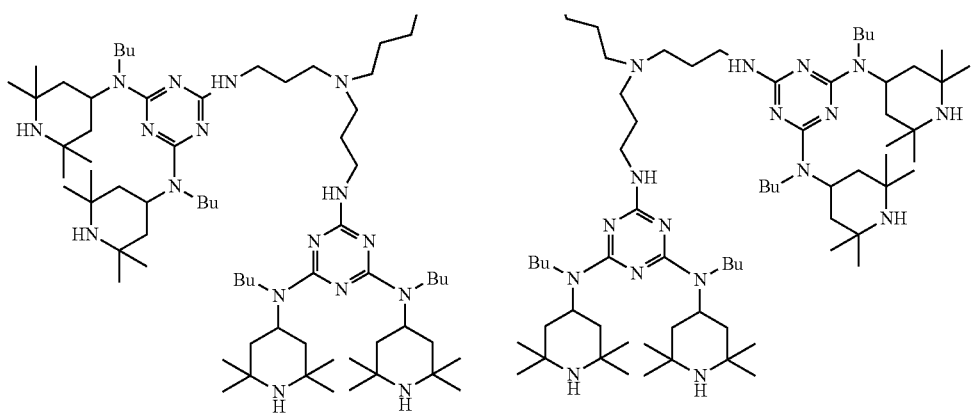

(5-10)
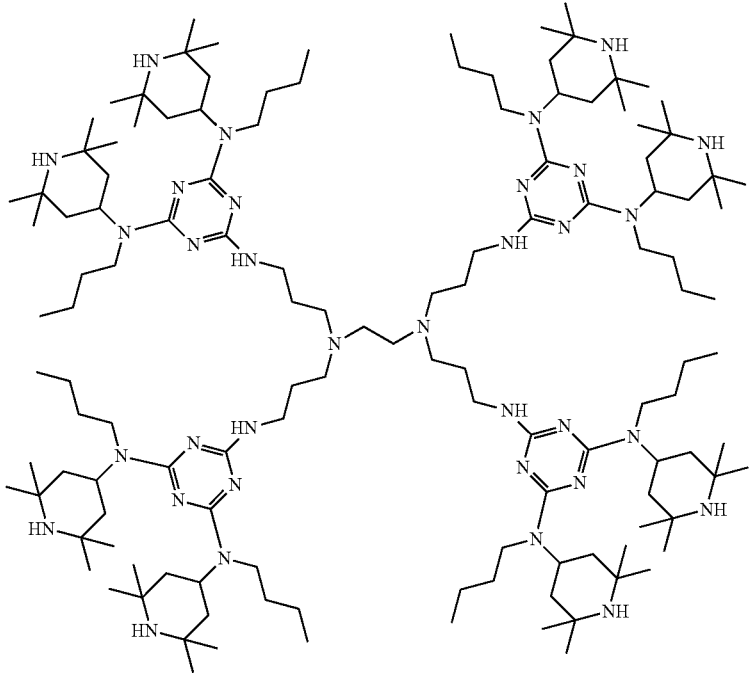
(5-11)
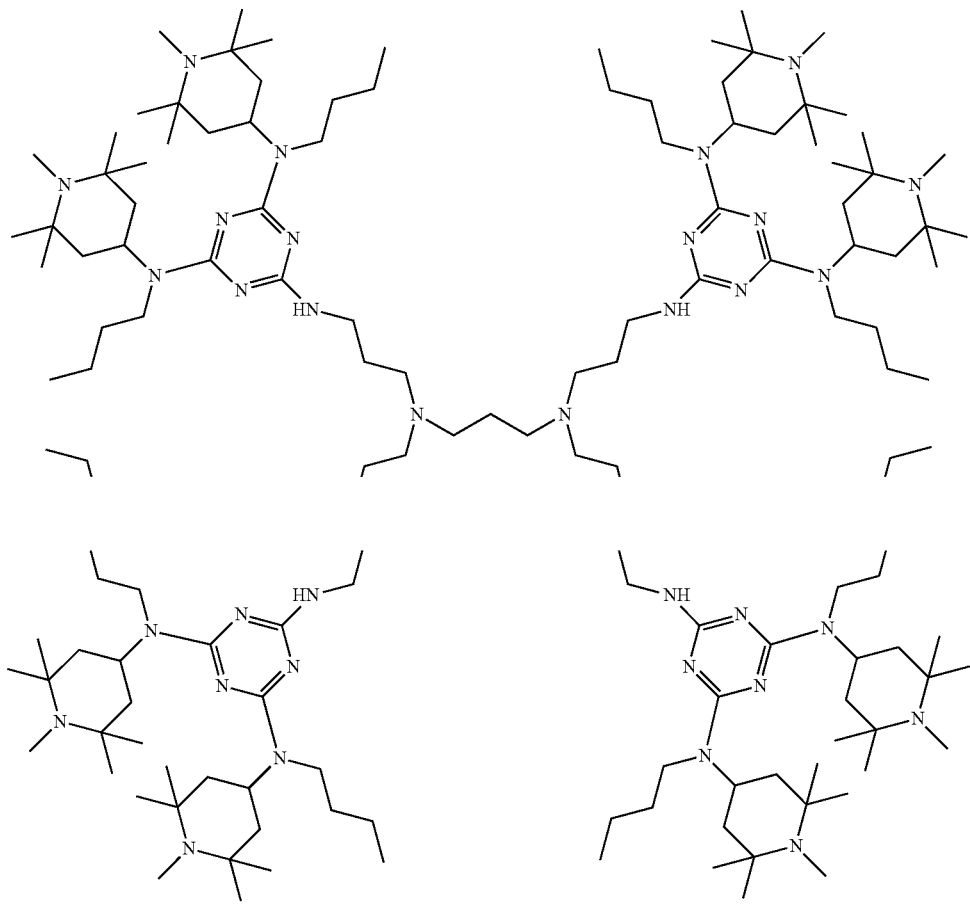

-continued
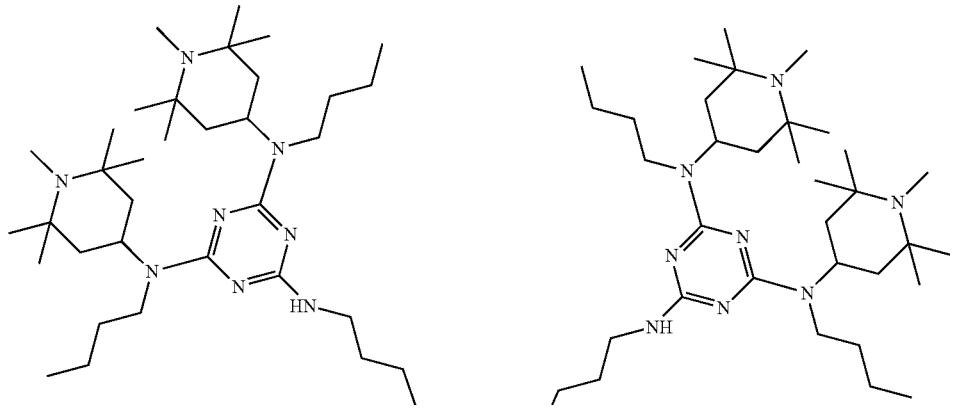
(5-12)
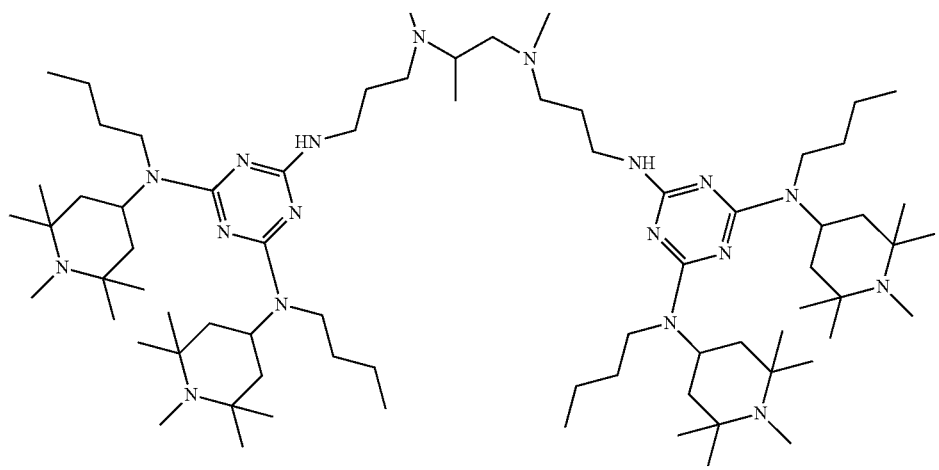
(5-13)
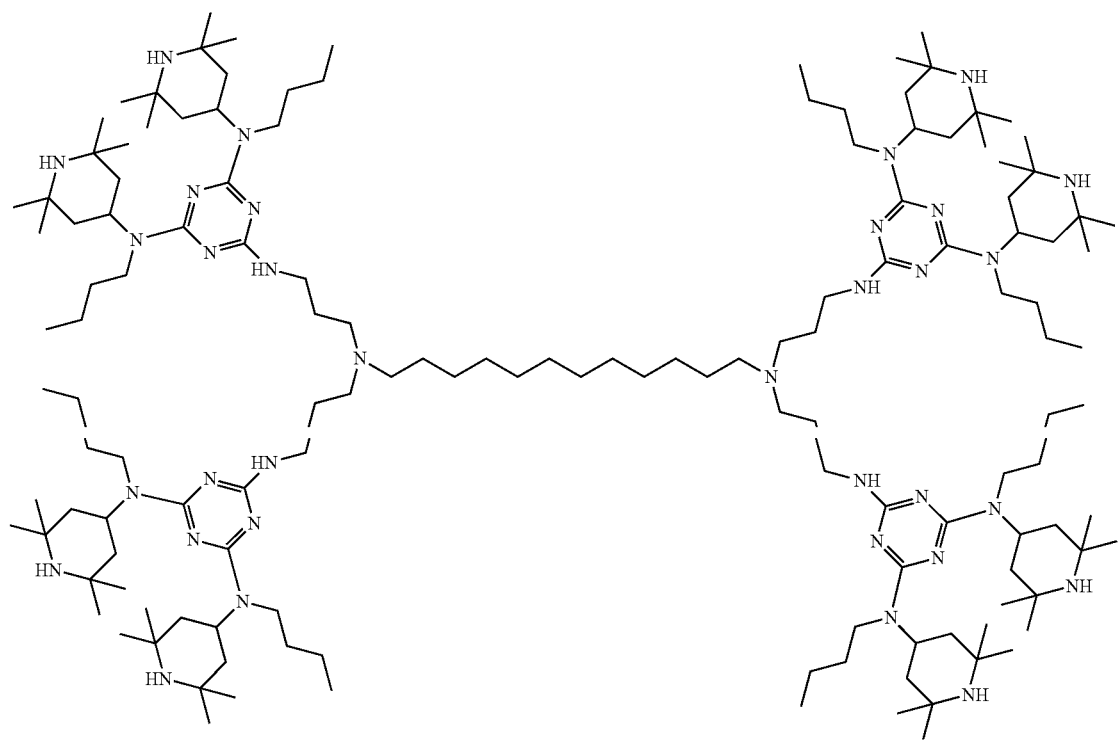

(5-14)
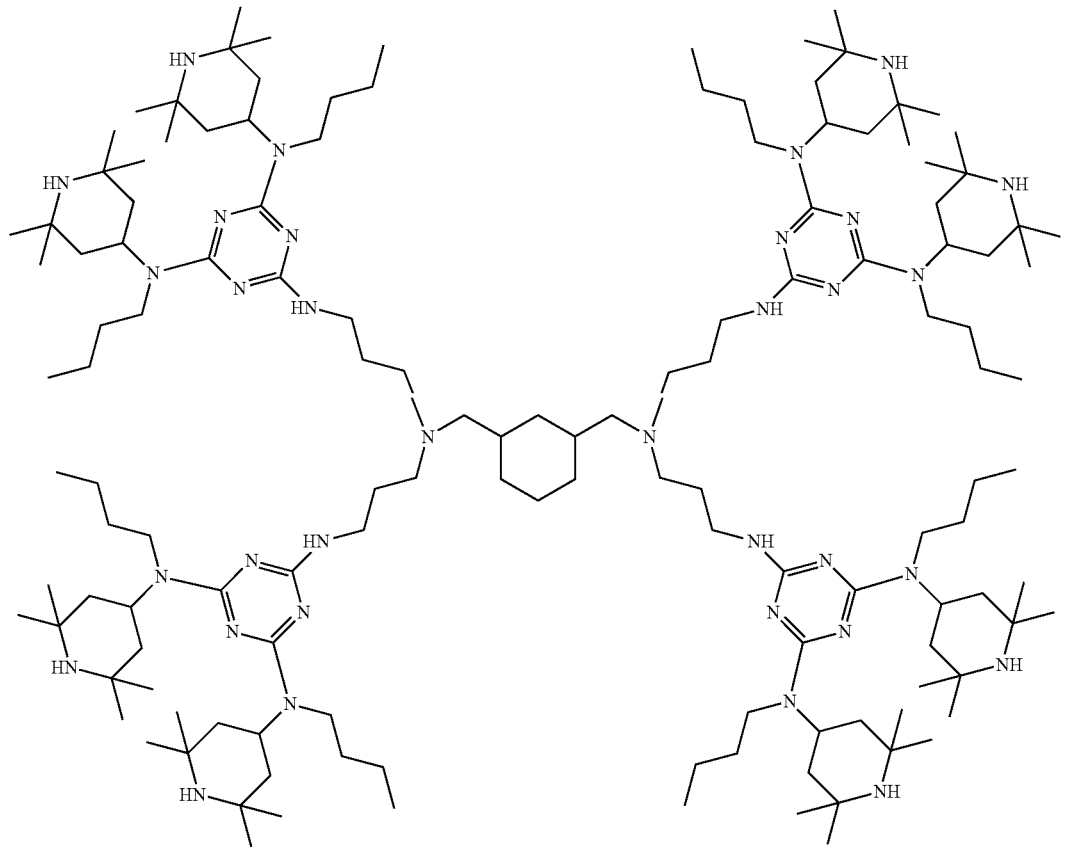
(5-15)
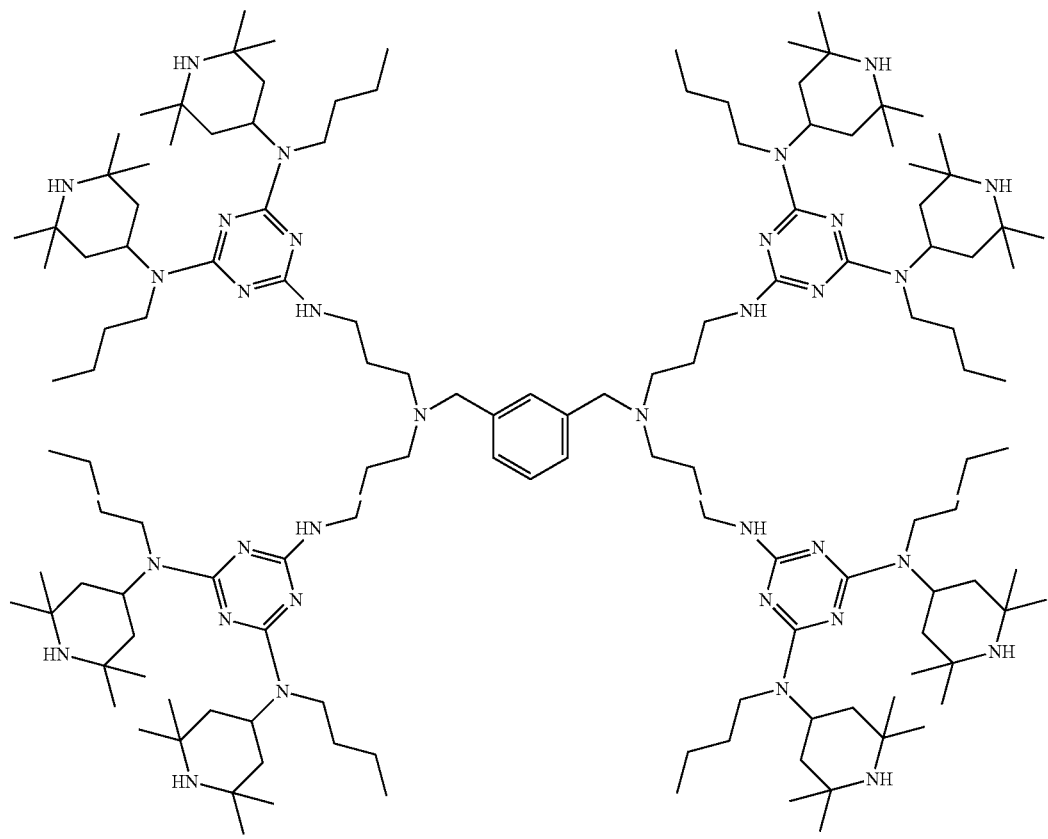

(5-16)
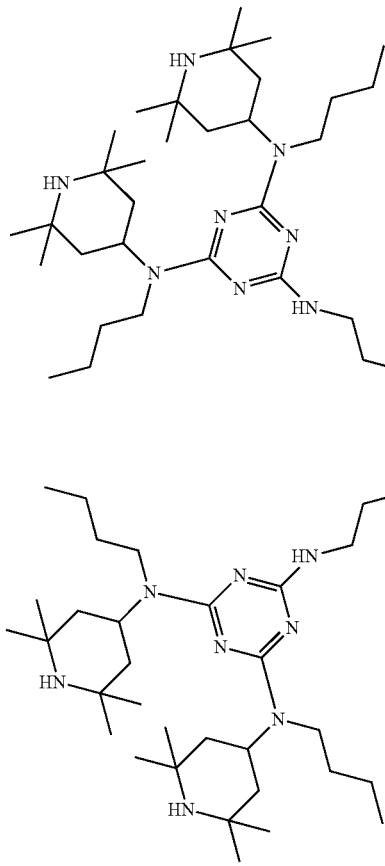 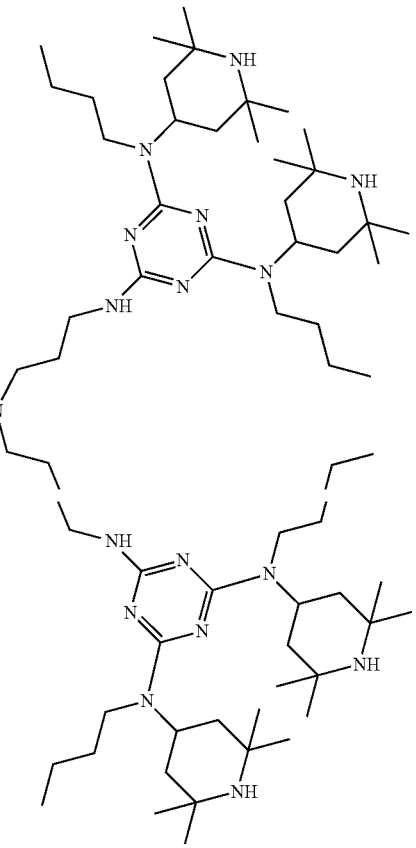
(5-17)
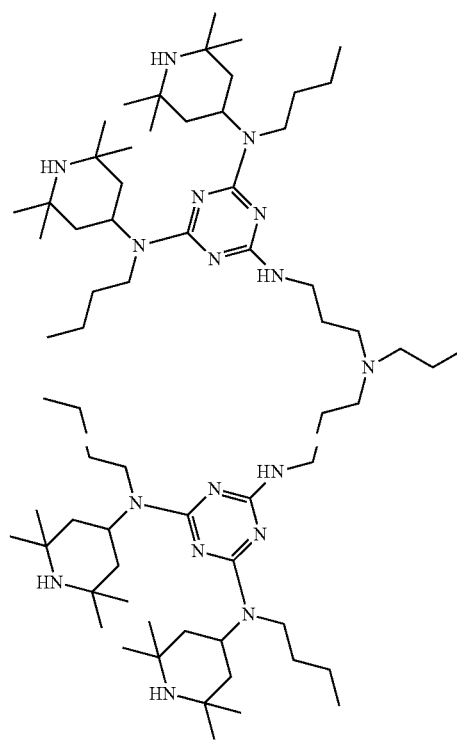 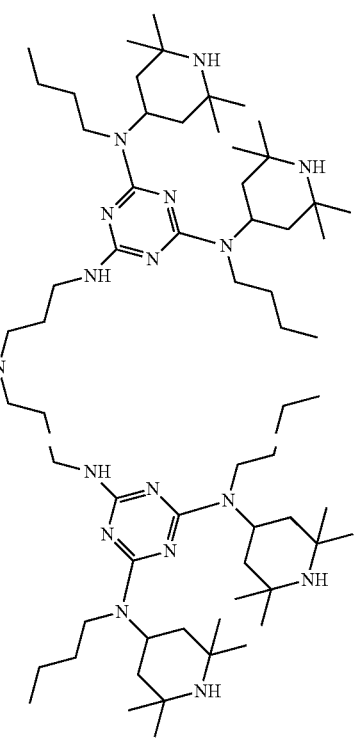

-continued
(5-18)
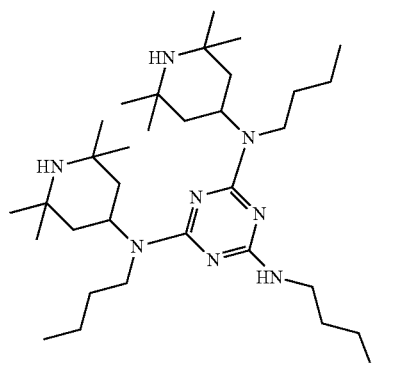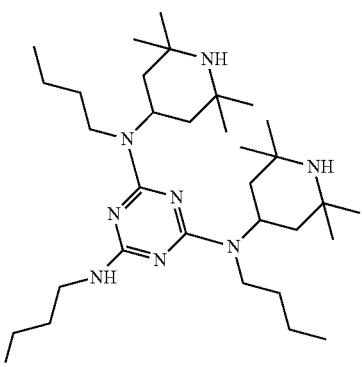
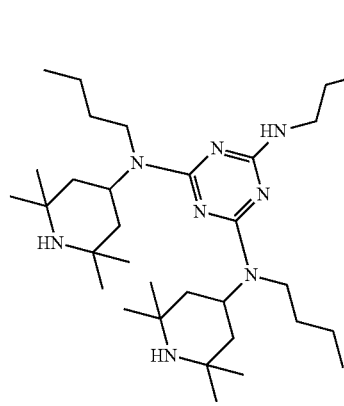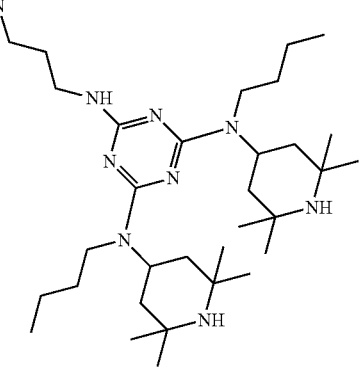
(5-19)
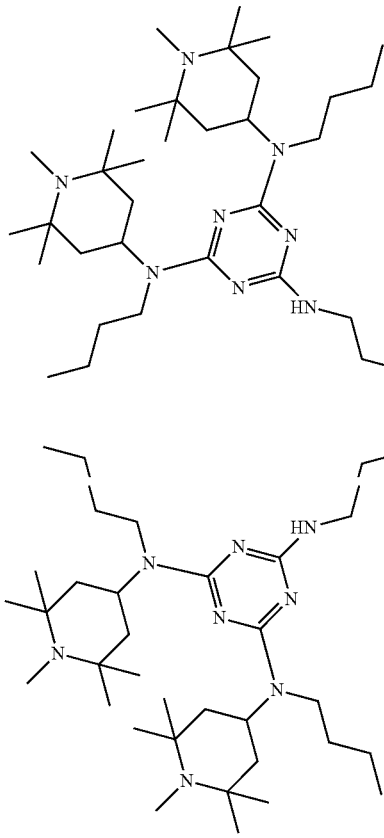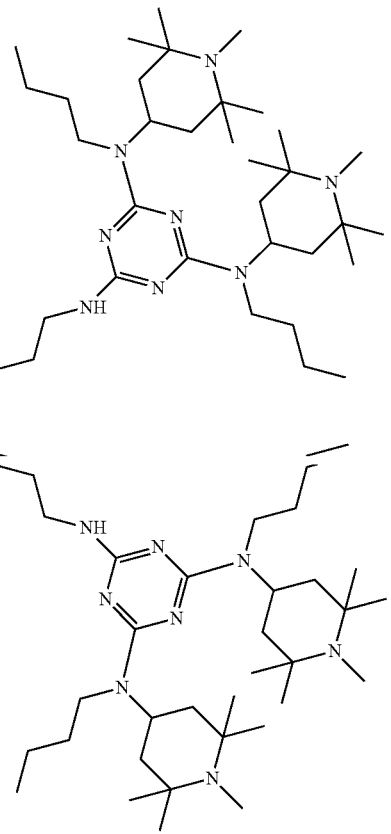

-continued
(5-20)
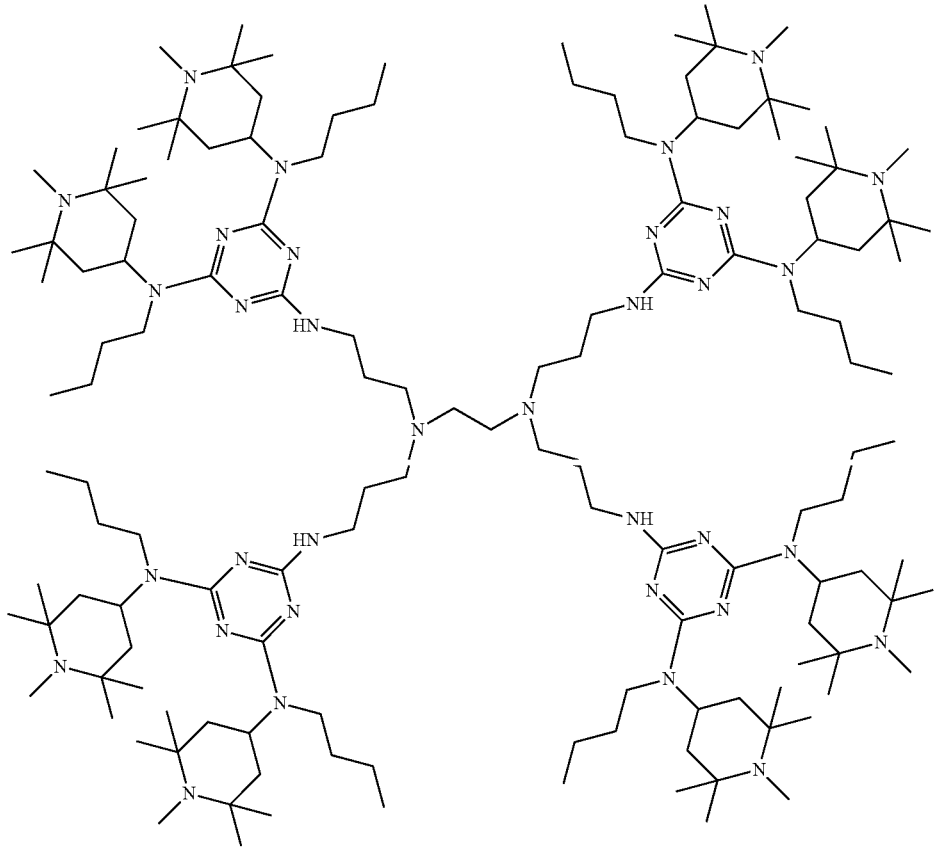
(5-21)
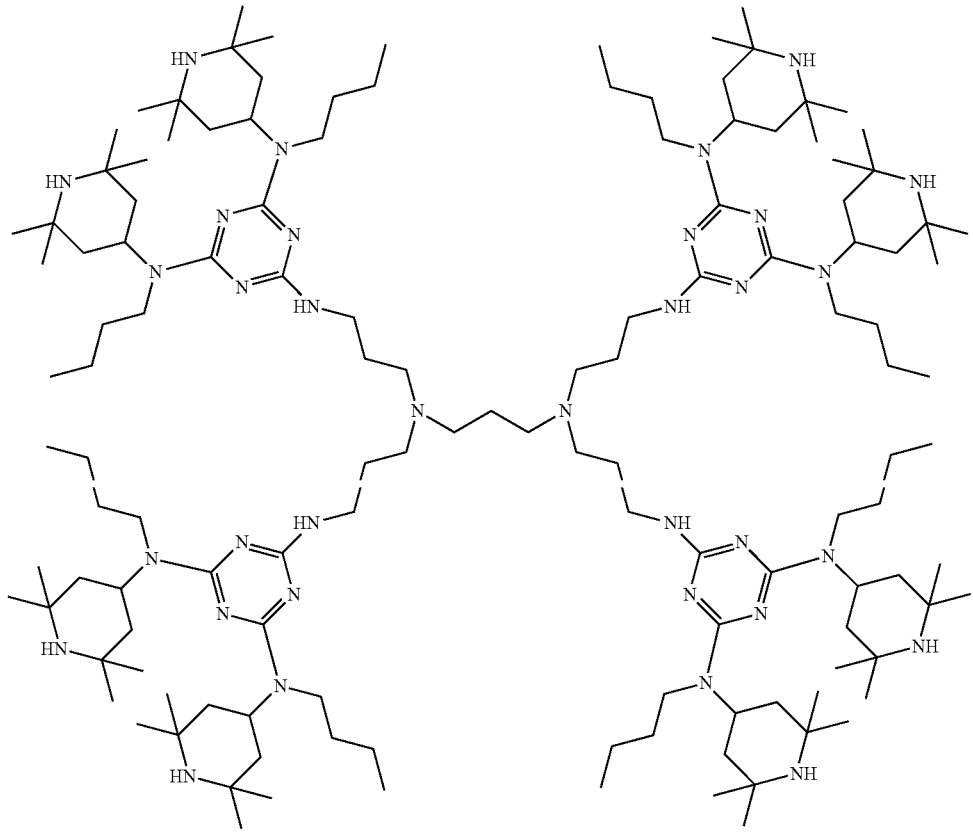

(5-22)
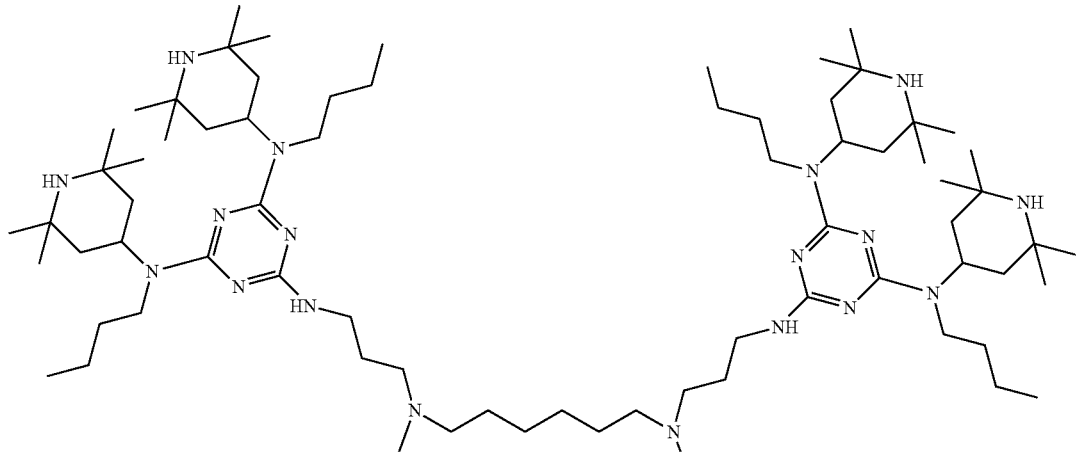
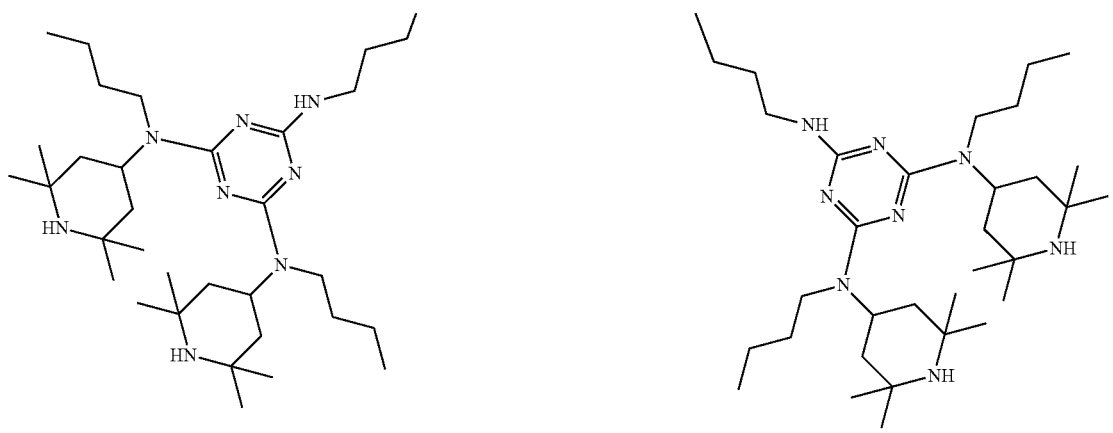
(5-23)
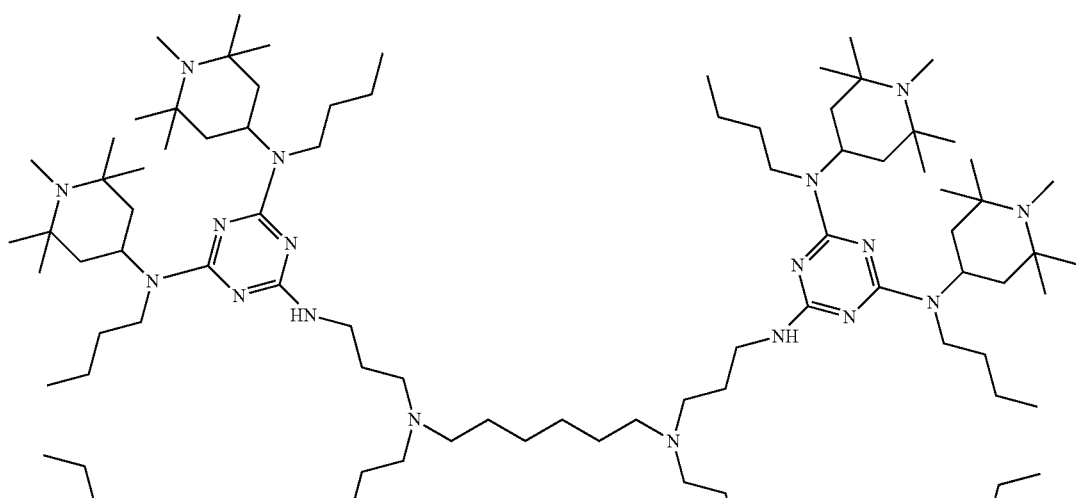

29
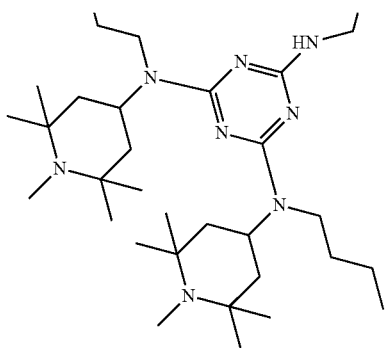
30
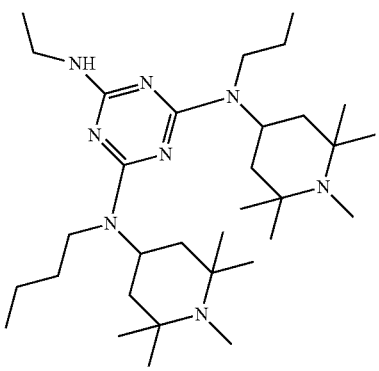
(5-24)
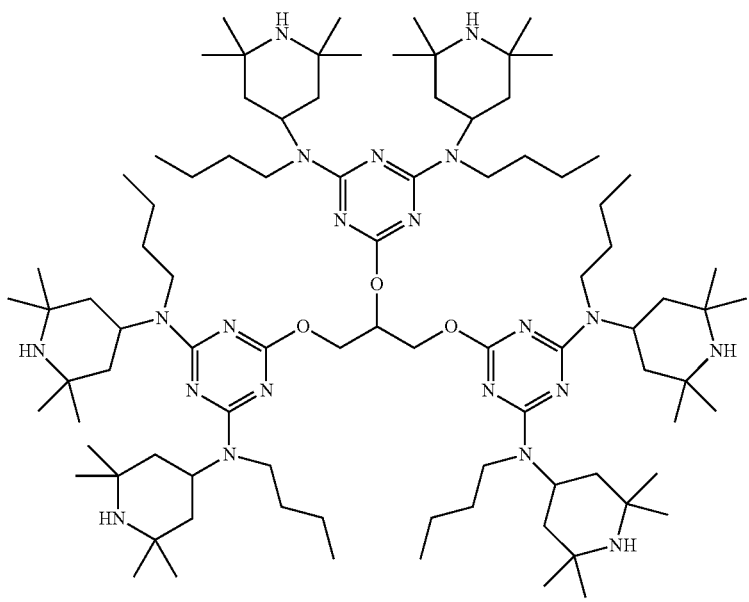
(5-25)
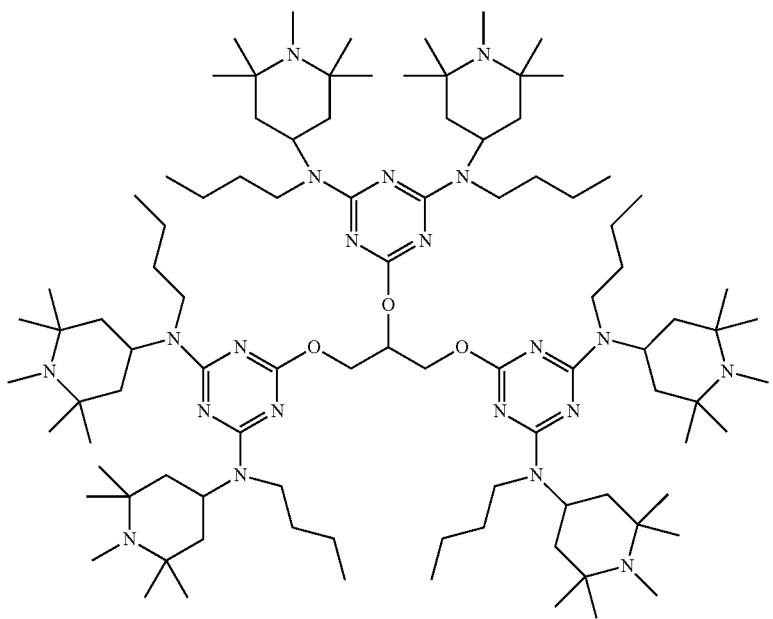

(5-26)
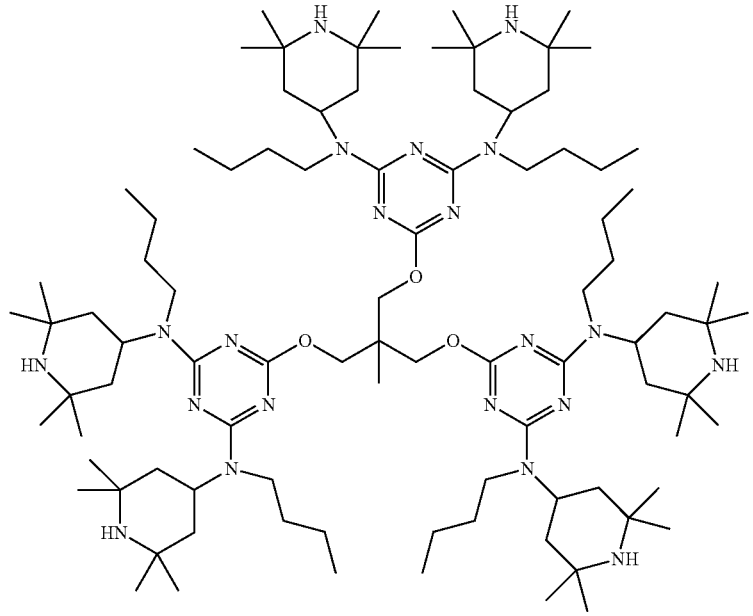
(5-27)
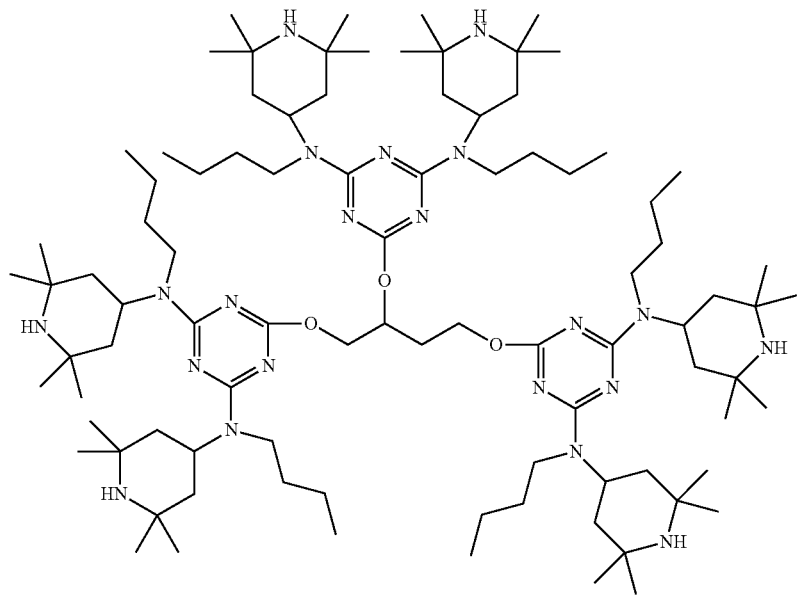

(5-28)
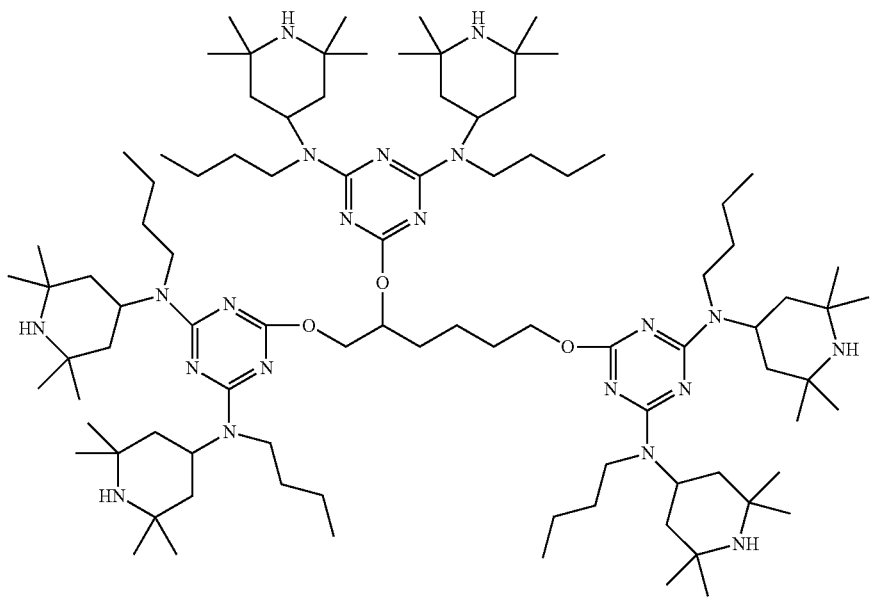
(5-29)
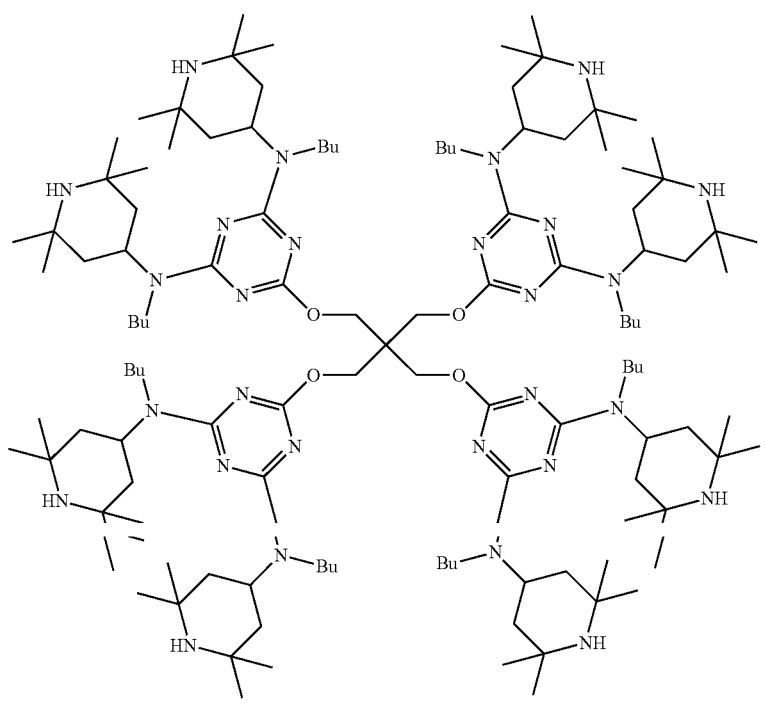

(5-30)
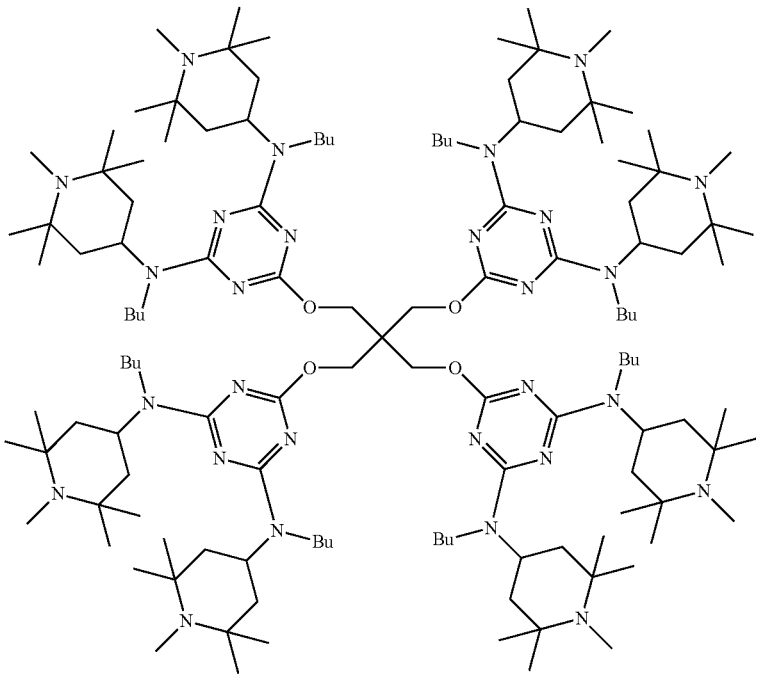
(5-31)
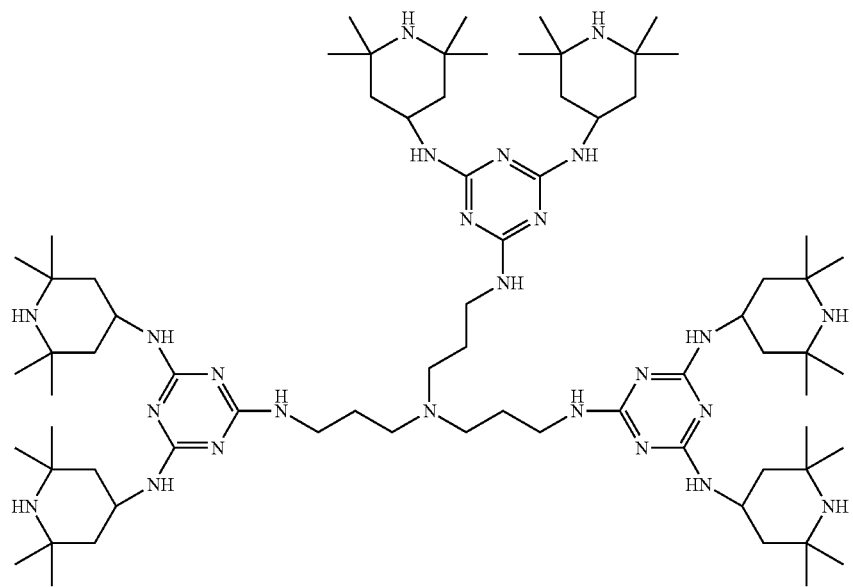

(5-32)
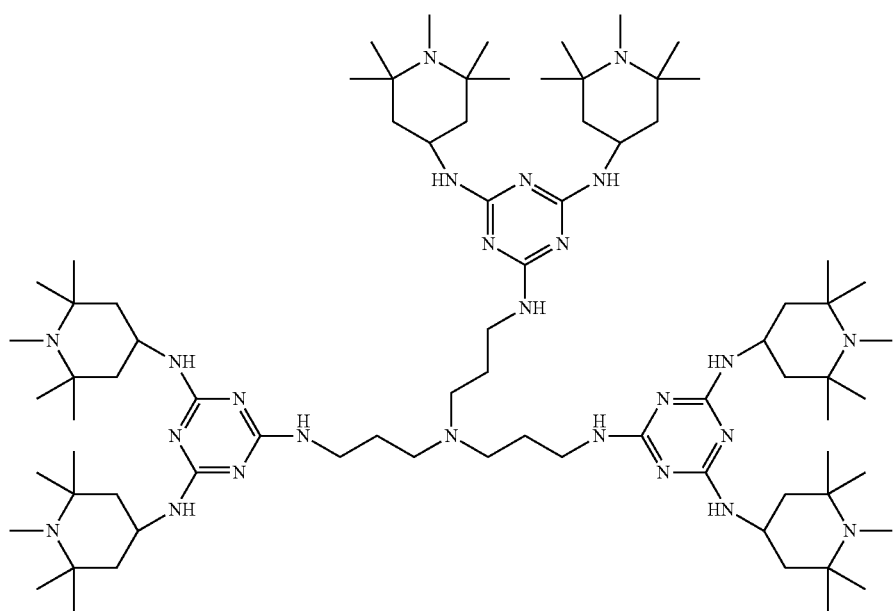
(5-33)
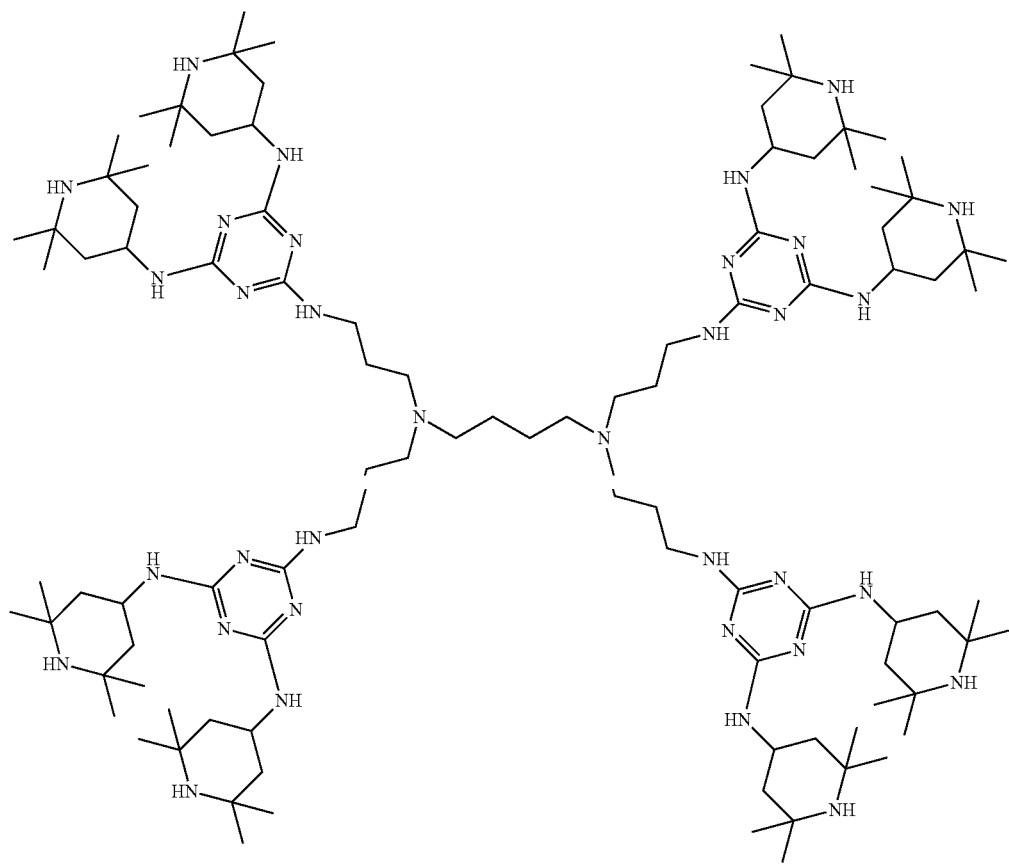

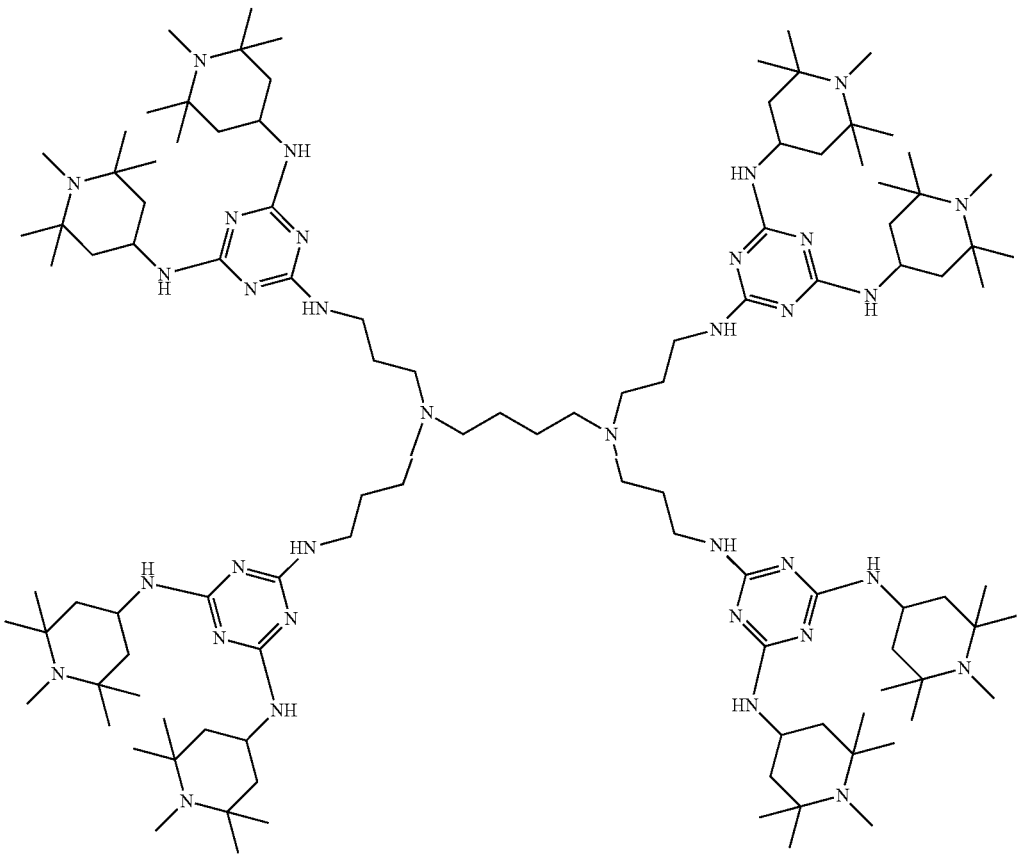

(5-34)

[Preparation Process of the Compound of the Present Invention]

The compound represented by the general formula (1) of the present invention can be prepared by coupling the compound represented by the general formula (6-1):

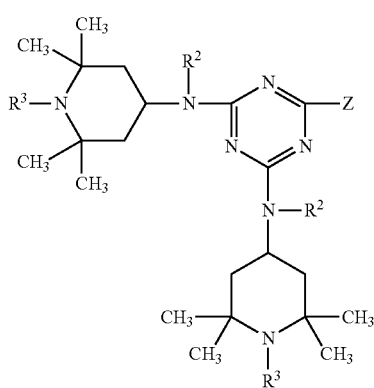

(6-1)

(wherein $R^2$, $R^3$ and Z have the same meanings as defined above)
and the compound represented by the general formula (6-2):

(6-2)

(wherein $R^1$, X and n have the same meanings as defined above).

The n-valent amine and alcohol represented by the general formula (6-2) used as a material of the present reaction can be obtained by purchase of commercially available products on the market or a known synthesis method. For example, tris(2-aminoethyl)amine, tris(3-aminopropyl)amine, N,N,N',N'-tetrakis(3-aminopropyl)-1,4-butanediamine, glycerin, 1,1,1-tris(hydroxymethyl)ethane, 1,2,4-butanetriol, 1,2,6-hexanetriol and pentaerythritol are commercially available. Whereas, for example, in the general formula (6-2), among the compounds in which $R^1$ is represented by the general formula (2-2), the compounds in which d represents 3 to 6 can be synthesized by methods described in Patent Document 9 (Japanese Unexamined PCT Publication No. Hei 6-506501) and Patent Document 10 (Japanese Unexamined PCT Publication No. Hei 9-508170).

In the following, the process for obtaining the compound represented by the general formula (1) of the present invention by the reaction of the compound represented by the general formula (6-1) and the compound represented by the general formula (6-2) is explained in more detail.

The molar ratio of the compound represented by the general formula (6-1) and the compound represented by the general formula (6-2) is most preferably n:1 but any one of the compounds may be supplied in an excessive amount. In cases where the compound is used in an excessive amount, the amount is from 1.01 to 10.0 times relative to the preferable amount. The charging method of both compounds to a reactor is not particularly limited. For example, the whole amounts of both compounds are collectively transferred to the reactor and the reaction may be started, or one of the compounds may be added gradually to the other compound while reacting the compounds.

The reaction may be carried out in the presence of a deoxidizer. The deoxidizer employable can include inorganic salts such as sodium hydroxide, potassium hydroxide, sodium carbonate and potassium carbonate; and organic bases such as triethylamine, tributylamine, pyridine, N,N-dimethylaniline, N-methylimidazole and 1,8-diazabicyclo[5.4.0]undec-7-ene (DBU). Further, in cases where the compound of the general formula (6-2) is alcohol, alcoholate such as sodium methoxide may be used.

The solvent used in the reaction is not particularly limited so long as it does not affect the reaction and can include water; saturated hydrocarbons such as pentane, hexane, heptane and cyclohexane; aromatic hydrocarbons such as benzene, toluene, xylene, mesitylene and ethylbenzene; halogenated hydrocarbons such as dichloromethane, chloroform, carbon tetrachloride, dichloroethane, chlorobenzene and dichlorobenzene; ethers such as ethylene glycol dimethyl ether, 1,3-dioxane, 1,4-dioxane, tetrahydrofuran, dimethyl ether, diethyl ether, diisopropyl ether and dibutyl ether; amides such as N,N-dimethylformamide; nitriles such as acetonitrile; ketones such as acetone, methyl ethyl ketone and methyl isobutyl ketone; esters such as methyl acetate and ethyl acetate; sulfur-containing solvents such as dimethyl sulfoxide; and 1,3-dimethyl-2-imidazolidinone (DMI).

These solvents are used singly or as a mixture thereof and in cases where they are used as the mixture, they can be used at an arbitrary ratio. The compound represented by the general formula (6-1) and the compound represented by the general formula (6-2), i.e., the raw materials may be dissolved in the reaction solvent to react them and may be reacted in a slurry state. In cases where a mixture of an organic solvent immiscible in water and water is selected as the reaction solvent, a phase transfer catalyst such as a tetrabutyl ammonium salt (for example, tetrabutyl ammonium hydrogensulfate) may be coexisted.

The amount of the reaction solvent used is not particularly limited and is in a range of from 1 to 1000 g, preferably from 1 to 500 g, and more preferably from 1 to 100 g relative to 1 g of the compound represented by the general formula (6-1), i.e., the raw material.

The present reaction is carried out in a temperature range from 0° C. to a boiling point of the solvent. Further, in cases where the reaction is carried out in an autoclave, the reaction temperature is not limited to the temperature range and the reaction is carried out in a range from 0 to 300° C., preferably from 0 to 250° C.

While the reaction time is not particularly limited and is appropriately determined depending on the raw material, the reaction condition or the like, it is usually from 10 minutes to 72 hours.

The isolation method of the compound represented by the general formula (1) of the present invention is not particularly limited. In cases where the product is precipitated from the reaction solvent, it can be isolated by filtration or centrifugal separation. In cases where it is dissolved in the reaction solvent, there is adopted a method for distilling off the solvent under reduced pressure or a method for precipitating by adding an appropriate solvent, followed by collecting by filtration or centrifugal separation. Further, the operation may be carried out by treating the compound with an appropriate acid to form a salt and may be performed by combining these methods.

With respect to the compound represented by the general formula (1) of the present invention, in cases where purification is required, a method well known as a conventional method can be adopted and can include a recrystallization method, a column chromatography method, washing (sludge treatment) by a solvent and activated carbon treatment. These purifications may be also carried out after the compound represented by the general formula (1) is treated with an appropriate acid to form a salt.

The solvent used in the recrystallization method, the column chromatography method, the washing by the solvent and the activated carbon treatment is not particularly limited and can include water, ammonia water; saturated hydrocarbons such as pentane, hexane, heptane and cyclohexane; aromatic hydrocarbons benzene, toluene, xylene and ethylbenzene; halogenated hydrocarbons such as dichloromethane, chloroform, carbon tetrachloride, dichloroethane, chlorobenzene and dichlorobenzene; lower alcohols such as methanol, ethanol, 1-propanol, isopropyl alcohol and tert-butyl alcohol; glycols such as ethylene glycol, diethylene glycol and propylene glycol; ethers such as ethylene glycol dimethyl ether, 1,3-dioxane, 1,4-dioxane, tetrahydrofuran, dimethyl ether, diethyl ether, diisopropyl ether and dibutyl ether; amides such as formamide and N,N-dimethylformamide; nitriles such as acetonitrile; ketones such as acetone and methyl ethyl keton; sulfur-containing solvents such as dimethyl sulfoxide; and 1,3-dimethyl-2-imidazolidinone.

These solvents are used singly or as a mixture thereof and in cases where they are used as the mixture, they can be used at an arbitrary ratio.

The amount of the solvent used at the time of the recrystallization, sludge treatment and activated carbon treatment is in a range of from 1 to 1000 g, preferably from 1 to 300 g relative to 1 g of the compound represented by the general formula (1).

The compound in which $R^3$ is a methyl group in the general formula (1) can be prepared by leading it to a compound in which R3 is a methyl group in the general formula (6-1) once using 1,2,2,6,6-pentamethyl-4-piperidone as a starting material and reacting this with the compound represented by the general formula (6-2). Further, the compound in which $R^3$ is a hydrogen atom in the general formula (1) can be also prepared by performing Eschweiler-Clarke reaction.

Here, the Eschweiler-Clarke reaction is one kind of Leuckart-Wallach reaction and means a reaction utilizing formaldehyde for methylation of amine.

The compound in which $R^3$ is a methyl group and X is N—$CH_3$ (namely, $R^4$ is a methyl group) in the general formula (1) can be synthesized by performing Eschweiler-Clarke reaction of the compound in which $R^3$ is a hydrogen atom and X is N—H (namely, $R^4$ is a hydrogen atom) in the general formula (1) or the compound in which $R^3$ is a methyl group and X is N—H.

The compound represented by the general formula (1) of the present invention can be also prepared by reacting the compound represented by general formula (8):

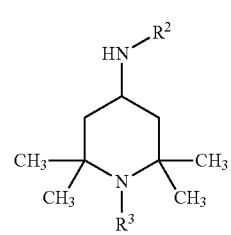

(8)

(wherein $R^2$ and $R^3$ have the same meanings as defined above) with cyanuric halides such as cyanuric chloride to lead it to the compound represented by the general formula (6-1) and reacting this with the compound represented by the general formula (6-2) at one pot without isolating it. These reactions are carried out under similar conditions to the reaction of the compound represented by the general formula (6-1) and the compound represented by the general formula (6-2) explained above.

[Organic Material Capable of Being Stabilized]

The compound represented by the general formula (1) of the present invention is extremely effective for improving an optical stability of an organic material, particularly a polymer material. Further, the compound can be utilized for improving stability of the organic material with respect to deterioration by heat and oxygen. Here, the oxygen includes not only molecular oxygen but also active oxygen. Example of the active oxygen can include singlet oxygen, hydroxyl radical, alkoxy radical, peroxy radical and hydroperoxide.

Examples of the organic material capable of being stabilized are shown in the following.

1. polymer of monoolefin and diolefin, for example, polypropylene, polyisobutylene, polybutene-1, poly(4-methylpentene-1), polyisoprene or polybutadiene and cycloolefin, for example, polymer of cyclopentene or norbornene, polyethylene (capable of being cross-linked if desired), for example, high density polyethylene (HDPE), high density and high molecular weight polyethylene (HDPE-HMW), high density and ultra high molecular weight polyethylene (HDPE-UHMW), middle density polyethylene (MDPE), low density polyethylene (LDPE), linear low density polyethylene (LLDPE) and branched low density polyethylene (BLDPE).

2. a mixture of the polymers described in 1., for example, a mixture of polypropylene and polyisobutylene, a mixture of polypropylene and polyethylene (for example, PP/HDPE, PP/LDPE) and various types of mixtures of polyethylene (for example, LDPE/HDPE, LLDPE/LDPE).

3. a copolymer of monoolefin and diolefin each other or with other vinyl monomer, for example, an ethylene/propylene copolymer, a propylene/butene-1 copolymer, a propylene/isobutylene copolymer, an ethylene/butene-1 copolymer, an ethylene/hexane copolymer, an ethylene/methylpentene copolymer, an ethylene/heptene copolymer, an ethylene/octene copolymer, a propylene/butadiene copolymer, an isobutylene/isoprene copolymer, an ethylene/alkyl acrylate copolymer, an ethylene/alkyl methacrylate copolymer, an ethylene/vinyl acetate copolymer and a copolymer of these copolymers and carbon monooxide or an ethylene/acrylic acid copolymer and those salts (ionomer), and a terpolymer of ethylene, propylene and diene, for example, hexadiene, dicyclopentadiene or ethylidene-norbornene; and a mixture of the copolymers each other and a mixture with the polymers described in 1., for example, a polypropylene/ethylene-propylene copolymer, a LDPE/ethylene-vinyl acetate (EVA) copolymer, a LDPE/ethylene acrylic acid (EAA) copolymer, LLDPE/EVA, LLDPE/EAA and random or alternate polyalkylene/carbon mono-oxide copolymer; and a mixture of these polymers and other polymers, for example, polyamide.

4. a resin containing a hydrogenated modified substance (for example, viscosity imparting agent) and a mixture of polyalkylene and starch in a hydrocarbon resin (for example, having from 5 to 9 carbon atoms).

5. polystyrene, poly-(p-methylstyrene), poly-(α-methylstyrene).

6. a copolymer of styrene or α-methylstyrene and diene or acrylic derivative, for example, styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; a mixture having high impact strength of a styrene copolymer and other copolymers, for example, polyacrylate, diene polymer or ethylene/propylene/diene terpolymer; and a block copolymer of styrene, for example, styrene/butadiene/styrene, styrene/isoprene/styrene, styrene/ethylene/butylene/styrene or styrene/ethylene/propylene/styrene.

7. a graft copolymerized polymer of styrene or α-methylstyrene, for example, a copolymer in which styrene is graft-copolymerized to polybutadiene, a copolymer in which a substance such as styrene is graft-copolymerized to polybutadiene-acrylonitrile; a copolymer in which styrene and acrylonitrile (or methacrylonitrile) are graft-copolymerized to polybutadiene; a copolymer in which styrene, acrylonitrile and methyl methacrylate are graft-polymerized to polybutadiene; a copolymer in which styrene and maleic anhydride are graft-copolymerized to polybutadiene; a copolymer in which styrene, acrylonitrile and maleic anhydride or maleinimide are graft-copolymerized to polybutadiene; a copolymer in which styrene and maleinimide are graft-copolymerized to polybutadiene; a copolymer in which styrene and alkyl acrylate or methacrylate are graft-copolymerized to polybutadiene; a copolymer in which styrene and acrylonitrile are graft-copolymerized to an ethylene/propylene/diene terpolymer; a copolymer in which styrene and acrylonitrile are graft-copolymerized to polyacrylate or polymethacrylate; a copolymer in which styrene and acrylonitrile are graft-copolymerized to an acrylate/butadiene copolymer; and a mixture of these copolymers and the copolymers listed in 6., for example, a copolymer mixture known as ABS, MBS, ASA and AES polymer.

8. a halogen-containing polymer, for example, polychloroprene, chlorinated rubber, chlorinated or chlorosulfonated polyethylene, a copolymer of ethylene and chlorinated ethylene, epichlorohydrin homopolymer and copolymer, particularly a polymer from a halogen-containing vinyl compound, for example, polyvinyl chloride, polyvinylidene chloride, polyvinyl fluoride, and polyvinylidene fluoride and these copolymers, for example, vinyl chloride/vinylidene chloride, vinyl chloride/vinyl acetate or vinylidene chloride/vinyl acetate copolymer.

9. a polymer derived from α,β-unsaturated acid and its derivative, for example, polyacrylate and polymethacrylate; polymethyl methacrylate in which an impact resistance is improved by butyl acrylate, polyacrylamide and polyacrylonitrile.

10. a copolymer of the monomers each other listed in above 9 or other unsaturated monomers, for example, an acrylonitrile/butadiene copolymer, an acrylonitrile/alkyl acrylate copolymer, an acrylonitrile/alkoxyalkyl acrylate or acrylonitrile/halogenated vinyl copolymer or an acrylonitrile/alkyl methacrylate/butadiene terpolymer.

11. a polymer derived from unsaturated alcohol and amine or their acyl derivative or their acetal, for example, polyvinyl alcohol, polyvinyl acetate, polyvinyl stearate, polyvinyl benzoate, polyvinyl maleate, polyvinyl butyral, polyallyl phthalate or polyallyl melamine; and a copolymer of these with the olefin described in above 1.

12. a homopolymer and a copolymer of cyclic ether, for example, polyalkylene glycol, polyethylene oxide, polypropylene oxide or a copolymer of those with bis-glycidyl ether.

13. polyacetal, for example polyoxymethylene containing polyoxymethylene and ethyleneoxide as a comonomer; polyacetal modified by thermoplastic polyurethane, acrylate or MBS.

14. polyphenylene oxide and polyphenylene sulfide and a mixture of polyphenylene oxide and polystyrene or polyamide.

15. polyurethane and its precursor substance derived from polyether containing a hydroxyl terminal group, polyester or polybutadiene as one component and aliphatic or aromatic polyisocyanate as the other component.

16. polyamide and copolyamide derived from diamine and dicarboxylic acid and/or aminocarboxylic acid or corresponding lactam. For example, polyamide 4, polyamide 6, polyamide 6/6, polyamide 6/10, polyamide 6/9, polyamide 6/12, polyamide 4/6 and polyamide 12/12, polyamide 11, polyamide 12, aromatic polyamide obtained by condensation of m-xylenediamine and adipic acid; polyamide prepared from hexamethylenediamine and isophthalic acid and/or terephthalic acid and, if desired, an elastomer as a modifying agent, for example, poly-(2,4,4-trimethylhexamethylene) terephthalamide or poly-m-phenyleneisophthalamide; further, a copolymer of the above polyamide with polyolefin, an olefin copolymer, ionomer or an elastomer chemically bonded or grafted; or a copolymer of those with polyether, for example, polyethylene glycol, polypropylene glycol or polytetramethylene glycol; and polyamide or copolyamide modified by EPDM or ABS; polyamide (RIM-polyamide system) condensed during processing.

17. polyurea, polyimide, polyamide-imide, polyether imide, polyester imide, polyhydantoin and polybenzimidazole.

18. polyester derived from dicarboxylic acid and diol and/or hydroxycarboxylic acid or correcponding lactone, for example, polyethylene terephthalate, polybutylene terephthalate, poly-1,4-dimethylol-cyclohexane terephthalate and polyhydroxybenzoate and block-copolyether-ester drived from polyether containing a hydroxyl terminal group; and polyester improved by polycarbonate or MBS.

19. polycarbonate and polyester-carbonate.

20. polysulfone, polyether sulfone and polyether ketone.

21. a cross-linked polymer derived from aldehyde as one component and phenol, urea or melamine as the other componet, for example, phenol/formaldehyde resin, urea/formaldehyde resin and melamine/formaldehyde resin.

22. dry or non-dry alkyd resin.

23. unsaturated polyester resin derived from a copolyester of saturated and unsaturated dicarboxylic acid, polyvalent alcohol and a vinyl compound as a cross-linking agent and their halogen-containing modified substance having low combustion property.

24. a substituted acrylic acid ester, for example, a cross-linking acrylic resin derived from epoxy acrylate, urethane acrylate or polyester-acrylate 25. melamine resin, urea resin, alkyd resin cross-linked by polyisocyanate or epoxy resin, polyester resin and acrylate resin.

26. a cross-linked epoxy resin derived from an aliphatic, cyclic aliphatic, heterocyclic or aromatic glycidyl compound, for example, a product of diglycidyl ether of bisphenol A and bisphenol F which is cross-linked by a usually used curing agent, for example, anhydride or amine by using or not using an accelerator.

27. a natural polymer, for example, cellulose, rubber, gelatin and a chemically modified homologous derivative, for example, cellulose acetate, cellulose propionate and cellulose butyrate, and cellulose ether, for example, methyl cellulose; and rosin and their derivative.

28. a mixture (polyblend) of the above polymers, for example, PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic PUR, POM/acrylate, POM/MBS, PPO/HIPS, PPO/PA 6.6 and a copolymer, PA/HDPE, PA/PP, PA/PPO, PBT/PC/ABS or PBT/PET/PC.

29. a natural and synthetic organic material comprising a pure monomer compound or their mixture, for example, a mineral oil, an animal or plant fat, oil and wax or an oil, fat and wax based on synthetic ester (for example, phthalate, adipate, phosphate or trimellitate) and a mixture of synthetic ester and mineral oil at any weight ratio used as a plasticizer for a polymer or a spinning preparation oil and aqueous emulsion of those materials.

30. aqueous emulsion for natural or synthetic rubber, for example, natural latex or latex of carboxylated styrene/butadiene copolymer.

A substance, preferably a polymer material, more preferably a substance selected from the above group is used as the organic material to be stabilized. Among them, polyolefin is preferable and polyethylene and polypropylene are particularly preferable.

[Method for Stabilizing Organic Material]

A method for stabilizing the organic material with respect to deterioration by light, heat, oxygen, ozone and an electromagnetic wave such as X ray and γ ray is to mix at least one kind of compound represented by the general formula (1) or its salt or a mixture thereof in the organic material. The compound of the general formula (1) or its salt or the mixture thereof can be used at various ratios depending on the property of the material to be stabilized, the final use and existence of other additives.

In general, the compound of the general formula (1) or its salt or the mixture thereof is used appropriately in an amount ranging from 0.001 to 15 parts by weight, preferably from 0.01 to 5 parts by weight, and more preferably from 0.05 to 3 parts by weight, for example, relative to 100 parts by weight of the organic material to be stabilized.

The compound of the general formula (1) or its salt or the mixture thereof can be added to the organic material in various convenient steps before preparation of a forming material, for example, before, during or after polymerization or cross-linking. Further, they can be mixed in the organic material in the pure form or in the form of filling in wax, oil or polymer.

The compound of the general formula (1) or its salt or the mixture thereof can be mixed into the organic material by various methods, for example, dry mixing in the powder form or wet mixing in the form of solution or suspension or in the form of master batch. In the operation, the organic material can be used in the form of powder, granule, solution or suspension or in the form of latex.

The material stabilized by the compound of the general formula (1) or its salt or the mixture thereof can be used, for example, for manufacturing a molded article, a film, a tape, a monofilament, a fiber, a surface coating, a coating composition or the like.

[Additives Which can be Used in Combination]

The organic material containing the compound of the general formula (1) or its salt or the mixture thereof can be added, if desired, in combination with other usually used additives for the organic material, for example, an anti-oxidant, a UV ray absorber, a photostabilizer, a pigment, a filler, a plasticizer, an anti-static agent, a flame retardant, a lubricant, a corrosion inhibitor and a metal inactivating agent.

As examples of the above additives, the following compounds can be listed.

1. Antioxidants (1.1) Alkylated monophenols, for example, 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenol having a linear or branched side chain, for example 2,6-dinonyl-4-methylphenol, 2,4-dimethyl-6-(1'-methylundecyl-1-yl)phenol, 2,4-dimethyl-6-(1'-methylheptadec-1-yl)phenol, 2,4-dimethyl-6-(1'-methyltridec-1'-yl)phenol and mixtures thereof.

(1.2) Alkylthiomethylphenols, for example, 2,4-di-octylthiomethyl-6-tert-butylphenol, 2,4-di-octylthiomethyl-6-methylphenol, 2,4-di-octylthiomethyl-6-ethylphenol and 2,6-di-dodecylthiomethyl-4-nonylphenol.

(1.3) Hydroquinones and alkylated hydroquinones, for example, 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhidroquinone, 2,5-di-tert-butyl-4-hydroxyanisole, 3,5-di-tert-butyl-4-hydroxyanisole, 3,5-di-tert-butyl-4-hydroxyphenylstearate, bis(3,5-di-tert-butyl-4-hydroxyphenyl)adipate.

(1.4) Tocopherols, for example, α-tocopherol, β-tocopherol, γ-tocopherol, δ-tocopherol, and mixtures thereof (vitamine E).

(1.5) Hydroxylated thiodiphenyl ethers, for example, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thio-bis(3,6-di-sec-amylphenol), 4,4'-bis(2,6-dimethyl-4-hydroxyphenyl)disulfide.

(1.6) Alkylidenebisphenols, for example 2, 2'-methylene-bis(6-tert-butyl-4-methylphenol), 2,2'-methylene-bis(6-tert-butyl-4-ethylphenol), 2,2'-methylene-bis[4-methyl-6-(α-methylcyclohexyl)phenol], 2,2'-methylene-bis(4-methyl-6-cyclohexylphenol), 2,2'-methylene-bis(6-nonyl-4-methlphenol), 2,2'-methylene-bis(4,6-di-tert-butylphenol), 2,2'-ethylidene-bis(4,6-di-tert-butylphenol), 2,2'-ethylidene-bis(6-tert-butyl-4-isobutylphenol), 2,2'-methylene-bis[6-(α-methylbenzyl)-4-nonylphenol], 2,2'-methylene-bis[6-(α,α-dimethylbenzyl)-4-nonylphenol], 4,4'-methylene-bis(2,6-di-tert-butylphenol), 4,4'-methylene-bis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethyleneglycol-bis[3,3-bis(3'-tert-butyl-4'-hydroxyphenyl)butylate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, and 1,1,5,5-tetrakis(5-tert-butyl-4-hydroxy-2-methylphenyl)pentane.

(1.7) O-, N- and S-benzyl compounds, for example, 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)-dithioterephthalate, bis(3,5-di-tert-butyl-4-hydroxybenzyl)sulfide, and isooctyl-3,5-di-tert-butyl-4-hydroxybenzylmercaptoacetate.

(1.8) a hydroxybenzylated malonate, for example, dioctadecyl-2,2-bis(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis(3,5-di-tert-butyl-4-hydroxybenzyl)-malonate, and bis[4-(1,1,3,3-tetramethylbutyl)phenyl]-2,2-bis(3,5-di-tert-butyl-4-hydroxybenzyl)-malonate.

(1.9) Aromatic hydroxybenzyl compounds, for example, 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, and 2,4,6-tris(3,5-di-tert-butyl-4-hydroxybenzyl)phenol.

(1.10) Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmerpapto-4,6-bis(3,5-di-tert-butyl-4-hydroxyphenoxy)-1,3,5-toriazine, 2,4,6-tris(3,5-di-tert-butyl-4-hydroxyphenoxy)-1,2,3-toriazine, 1,3,5-tris(3,5-di-tert-butyl-4-hydroxybenzyl)isocyanu rate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-toriazine, 1,3,5-tris(3,5-dicyclohexyl-4-hydroxybenzyl)isocyanurate.

(1.11) Benzylphosphonates, for example, dimethyl-2,5-di-tert-butyl-4-hydroxybenzyl phosphonate, diethyl-3,5-di-tert-butyl-4-hydroxybenzyl phosphonate, dioctadecyl-3,5-di-tert-butyl-4-hydroxybenzyl phosphonate, dioctadecyl-5-tert-butyl-4-hydroxy-3-methlbenzyl phosphonate, and the calcium salt of the monoethyl ester of 3,5-di-tert-butyl-4-hydroxybenzyl phosphonic acid.

(1.12) Acylaminophenols, for example 4-hydroxylauranilide, 4-hydroxystearanilide, octyl N-(3,5-di-tert-butyl-4-hydroxyphenyl)carbamate.

(1.13) Esters of β-(3,5-di-tert-butyl-4-hydroxyphenyl)propionic acid with the following mono- or polyhydric alcohols, for example, with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalic diamide, 3-thiaundecanol, 3-thiapentadecanol, trimethylhexanediol, trimethylolpropane, 4-hydroxymethyl-1-phospha-2,6,7-trioxabicyclo[2.2.2]octane.

(1.14) Esters of β-(5-tert-butyl-4-hydroxy-3-methylphenyl)propionic acid with the following mono- or polyhydric alcohols, for example, with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalic diamide, 3-thiaundecanol, 3-thiapentadecanol, trimethylhexanediol, trimethylolpropane, 4-hydroxymethyl-1-phospha-2,6,7-trioxabicyclo[2.2.2]octane.

(1.15) Esters of β-(3,5-dicyclohexyl-4-hydroxyphenyl)propionic acid with the following mono- or polyhydric alcohols, for example, with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalic diamide, 3-thiaundecanol, 3-thiapentadecanol, trimethylhexanediol, trimethylolpropane, 4-hydroxymethyl-1-phospha-2,6,7-trioxabicyclo[2.2.2]octane.

(1.16) Esters of 3,5-di-tert-butyl-4-hydroxyphenyl acetic acid with the following mono- or polyhydric alcohol, for example, with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalic diamide, 3-thiaundecanol, 3-thiapantadecanol, trimethylhexanediol, trimethylolpropane, 4-hydroxymethyl-1-phospha-2,6,7-trioxabicyclo [2.2.2]octane.

(1.17) amides of β-(3,5-di-tert-butyl-4-hydroxyphenyl) propionic acid, for example, N,N'-bis(3,5-di-tert-butyl-4-hydroxyphenylpropionyl)hexamethylenedimaine, N,N'-bis(3,5-di-tert-butyl-4-hydroxyphenylpropionyl) trimethylenedimaine, N,N'-bis(3,5-di-tert-butyl-4-hydroxyphenylpropionyl)hydrozine.

(1.18) Ascorbic acid (vitamin C)

(1.19) Aminic antioxidants, for example, N,N'-diisopropyl-p-phenylenediamine, N,N'-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamide)diphenylamine, N,N'-dimethyl-N,N'-sec-butyl-p-phenylenediamine, diphenylamine, N-aryldiphenylamine, 4-isopropoxydiphenylamine, N-phenyl-1-naphthylamine, N-phenyl-2-naphthylamine, octylated diphenylamine, p,p'-di-tert-butyl-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminophenylmethane, 1,2-bis[(2-methylphenyl)amino] ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamine, mixture of mono- and dialkylated isopropy/isohexyldiphenylamine, mixture of mono- and dialkylated tert-butyldiphenylamine, 2,3-dihydro-3,3-dimethyl-4H-1,4-benzothiazine, phenothiazine, N-arylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl-hexamethylenediamine, bis(2,2,6,6-tetramethylpiperid-4-yl) sebacate, 2,2,6,6-tetramethylpiperid-4-one, and 2,2,6,6-tetramethylpiperidin-4-ol.

2. UV absorbers and Light Stabilizers (2.1) 2-(2'-Hydroxyphenyl)benzotriazole, for example, 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2'-octyloxycarbonylethyl)phenyl)-5-chlorobenzotriazole, 2-(3'-tert-butyl-5'-[2-(2-ethylhexyloxy) carbonylethyl]-2'-hydroxyphenyl)-5-chlorobenzotriazole, 2-(3'-tert-butyl-2'-hydroxy-5'-(2-methoxycarbonylethyl) phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octoxycarbonylethyl)phenyl) benzotriazole, 2-(3'-tert-butyl-5'-(2-(2-ethylhexyloxy) carbonylethyl)-2'-hydroxyphenyl)benzotriazole, 2-(3'-dodecyl-2'-hydroxy-5'-methylphenyl)benzotriazole, and mixture of 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; transesterification product of 2-[3'-tert-butyl-5'-(2-methoxycarbonylethyl)-2'-hydroxyphenyl]benzotriazole with polyethylene glycol 300; $[R^{21}—CH_2CH_2—COO(CH_2)_3]_2$—, wherein $R^{21}$=3'-tert-butyl-4'-hydroxy-5'-2H-benzotriazole-2-ylphenyl.

(2.2) 2-Hydroxybenzophenones, for example, 4-hydroxy-, 4-methoxy, 4-octoxy, 4-decyloxy-, 4-dodecyloxy-, 4-benzyloxy-, 4,2',4'-trihydroxy- or 2'-hydroxy-4,4'-dimethoxy derivative.

(2.3) Esters of substituted or unsubstituted benzoic acids, for example 4-tert-butylphenylsalicylate, phenyl salicylate, octylphenylsalicylate, dibenzoyl resorcinol, bis(4-tert-butylbenzoyl)resorcinol, benzoyl resorcinol, 2,4-di-tert-butylphenyl3,5-di-tert-butyl-4-hydroxybenzoate, hexadecyl-3,5-di-tert-butyl-4-hydroxybenzoate, octadecyl3,5-di-tert-butyl-4-hydroxybenzoate, 2-methyl-4,6-di-tert-butylphenyl-3,5-di-tert-butyl-4-hydroxybenzoate.

(2.4) Acrylates, for example, ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, buty α-cyano-β-methyl-p-methoxycinnamate, methyl α-carbomethoxy-p-methoxy cinnamate, and N-(β-carbomethoxy-β-cyanovinyl)-2-methylindoline.

(2.5) Nickel compounds, for example, n ickel complexes of 2,2'-thiobis[4-(1,1,3,3-tetramethylbutyl)phenol], such as the 1:1 or 1:2 complex, if desired, with additional ligands such as n-butylamine, triethanolamine or N-cyclohexyl-di-ethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, if desired,with additional ligands.

(2.6) Sterically hindered amines, for example bis(2,2,6,6-tetramethylpiperidyl) sebacate, bis(2,2,6,6-tetramethylpiperidiyl) succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, condensation product of 1-(2-hydroxyethyl)-2,2,6,6-tetramethyl-4-hydroxypiperizine and succinic acid, condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperizine, 4-stearyloxy-2,2,6,6-tetramethylpiperizine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5] decane-2,4-dione, bis(1-octyloxy-2,2,6,6-tetramethylpiperidyl)sebacate, bis(1-octyloxy-2,2,6,6-tetramethylpiperidyl)succinate, condensation product of N,N'-bis(2,2,6,6-tetramethyl-4-piperidyl)-hexamethylenediamine and 4-morpholino-2,6-dichloro-1,3,5-triazine, condensation product of 2-chloro-4,6-bis(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine and 1,2-bis(3-aminopropylamino) ethane, 8-acetyl-3-dodecyl-7,7,9,9-tetramethyl-1,3,8-triazaspiro[4.5]decane-2,4-dione, 3-dodecyl-1-(2,2,6,6- tetramethyl-4-piperidyl)pyrrolidine-2,5-dione, 3-dodecyl-1-(1,2,2,6,6-pentamethyl-4-piperidyl)-pyrrolidine-2,5-dione, mixture of 4-hexadecyloxy and 4-stearoyloxy-2,2,6,6-tetramethylpiperidine, condensation product of N,N'-bis(2,2,6,6-tetramethyl-4-piperidyl)hexamethylenediamine and 4-cyclohexylamino-2,6-dichloro-1,3,5-triazine, condensation product of 1,2-bis(3-aminopropylamino)ethane and 2,4,6-dichloro-1,3,5-triazine, and 4-butylamino-2,2,6,6-tetramethylpiperidine (CAS Reg. No [136504-96-6], N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4.5] decane, reaction product of 7,7,9,9-tetramethyl-2-cycloundecyl-1-oxa-3,8-diaza-4-oxospiro[4.5]decane and epichlorohydrin.

(2.7) Oxamides, for example, 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl) oxamide, 2-ethoxy-5-tert-butyl-2'-ethyloxanilide and its mixture with 2-ethoxy-2'-ethyl-5,4'-di-tert-butoxanilide, mixtures of o- and p-methoxy-disubstituted oxanilides and a mixture of o- and p-ethoxy-disubstituted oxanilides and mixtures of o- and p-ethoxy-disubstituted oxanilides.

(2.8) 2-(2-hydroxyphenyl)-1,3,5-triazine, for example, 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methyphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-toriazine, 2-[4-(dodecyloxy/tridecyloxy-2-hydroxypropoxy)-2-hydroxyphenyl]-4,6-bis(2,4-dimethylphenyl)-1,3,5-toriazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl)-1,3,5-triazine, 2-(2-hydroxy-4-methoxyphenyl-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine.

3. Metal deactivators, for example, N,N'-diphenyl oxalic diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bis-phenylhydrazide, N,N'-diacetyladipoyl dihydrazide, N,N'-bis-salicyloyl-oxalyl dihydrazide, N,N'-bis-salicyloyl-thiopropionyl dihydrazide.

4. Phosphites (phosphorous ester) and phosphonites, for example, triphenyl phosphite, diphenylalkyl phosphite, phenyldialkyl phosphite, tris(nonylphenyl)phosphite, trilauryl phosphite, trioctadecyl phosphite, distearyl-pentaerythritol diphosphite, tris(2,4-di-tert-butylphenyl)phosphite, diisodecylpenta-erythritol diphosphite, bis(2,4-di-tert-butylphenyl)-pentaerythritol diphosphite, bis(2,6-di-tert-butyl-4-methylphenyl)-pentaerythritol diphosphite, di-isodecyloxy-pentaerythritol diphosphite, bis(2,4-di-tert-butyl-6-methylphenyl)-pentaerythritol diphosphite, bis(2,4,6-tris-tert-butylphenyl)-pentaerythritol diphosphite, tristearylsorbitol triphosphite, tetrakis(2,4-di-tert-butylphenyl)-4,4'-biphenylene diphosphonite, 6-isooctyloxy-2,4,8,10-tetra-tert-butyl-12H-dibenz[d,g]-1,3,2-dioxaphosphocine, 6-fluoro-2,4,8,10-tetra-tert-butyl-12-methyl-dibenz[d,g]-1,3,2-dioxaphosphocine, bis(2,4-di-tert-butyl-6-methylphenyl)methylphosphite, bis(2,4-di-tert-butyl-6-methylphenyl)ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitron, for example, N-benzyl-α-phenyl-nitron, N-ethyl-α-methyl-nitron, N-octyl-α-heptyl-nitron, N-lauryl-α-undecyl-nitron, N-tetradecyl-α-tridecyl-nitron, N-hexadecyl-α-pentadecyl-nitron, N-octadecyl-α-heptadecyl-nitron, N-hexadecyl-α-heptadecyl-nitron, N-octadecyl-α-pentadecyl-nitron, N-heptadecyl-α-heptadecyl-nitron, N-octadecyl-α-hexadecyl-nitron, nitron derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony catecholate or tin catecholate.

11. Nucleating agents, for example, inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers).

12. Fillers and reinforcing agents, for example calcium carbonate, silicates, glass fibres, glass bulbs, asbestos, talc, kaolin, mica, barium sulfate, metal oxides and hydroxides, carbon black, graphite.

13. Other additives, for example, plasticisers, lubricants, emulsifiers, pigments, rheology additives, catalysts, flow-control agents, optical brighteners, flameproofing agents, antistatic agents and blowing agents.

The weight ratio of the compound of the general formula (1) or its salt or the mixture thereof with respect to the usually used additive may be 1:0.001 to 1:200.

The compound of the general formula (1) or its salt or the mixture thereof is useful for polyolefin added with a pigment, particularly polyethylene and polypropylene.

The present specification includes a content described in the specification of Japanese Patent Application No. 2005-13663, i.e., a basic application of priority of the present application.

EXAMPLE

In the following, the present invention is explained in more detail based on Examples but the present invention is not limited to these. Further, all percentages represent a percentage per weight unless otherwise indicated. Further, a melting point represents a temperature of finishing of melting when a sample was collected in a capillary at a thickness of approximately 2 to 3 mm and was heated in a bath solution.

Example 1

Preparation of Compound Represented by Formula (5-1)

A solution of 1.72 g of 4-aminomethyl-1,7-diaminoheptane and 19.29 g of 2-chloro-4,6-bis(N-(2,2,6,6-tetramethylpiperidin-4-yl)butylamino)-1,3,5-triazine in 1,3-dimethyl-2-imidazolidinone (DMI) (140 ml) was stirred at 160° C. for 6 hours. After the reaction mixture was left to stand to room temperature, 300 mL of water and 4.84 g of potassium carbonate were added thereto and the mixture was stirred for 30 minutes, followed by extraction with xylene (500 mL). The organic layer obtained by liquid separation was washed with a saturated aqueous NaCl solution and dried with anhydrous magnesium sulfate. After the solvent was distilled off, the concentrated residue was purified by silica gel column chromatography to give 12.15 g of the title compound as a pale yellow solid.

$^1$H NMR (CDCl$_3$): δ=0.73-0.95 (18H, m), 0.73-1.70 (57H, m), 0.95-1.10 (36H, m), 1.15-1.22 (36H, m), 3.05-3.50 (18H, m), 5.15 (6H, br).

MS (FD, m/z): 1659.

Melting point: 113° C.

Example 2

Preparation of Compound Represented by Formula (5-2)

A solution of 1.72 g of 4-aminomethyl-1,7-diaminoheptane and 19.75 g of 2-chloro-4,6-bis(N-(1,2,2,6,6-pentamethylpiperidin-1-yl)butylamino)-1,3,5-triazine in DMI (100 g) was stirred at 160-200° C. for 6 hours. After the reaction mixture was left to stand to room temperature, DMI was distilled off and 500 mL of water and 4.84 g of potassium carbonate were added thereto, followed by stirring of the mixture. After the reaction mixture was extracted with ethyl acetate (600 mL), the obtained organic layer was washed with a saturated aqueous NaCl solution and dried with anhydrous magnesium sulfate. After the solvent was distilled off, the concentrated residue was purified by silica gel column chromatography to give 16.45 g of the title compound as a pale yellow solid.

$^1$H NMR (CDCl$_3$): δ=0.80-0.97 (18H, m), 0.80-1.70 (57H, m), 0.97-1.10 (36H, m), 1.10-1.20 (36H, m), 2.25 (18H, s), 3.20-3.38 (18H, m), 5.12 (6H, br).

MS (FD, m/z): 1743.

Melting point: 115° C.

Example 3

Preparation of Compound Represented by Formula (5-3)

A mixture of 9.95 g of the compound synthesized in Example 1, 38.96 g of 37% formaline and 22.55 g of 98% formic acid was heated under reflux for 12 hours. After the reaction mixture was concentrated, 200 mL of water and 15.18 g of sodium hydrogencarbonate were added thereto and the mixture was stirred at room temperature, followed by extraction with toluene (300 mL). After the organic layer was washed with a saturated aqueous NaCl solution and dried with anhydrous magnesium sulfate, the solvent was distilled off under reduced pressure. The concentrated residue was purified by silica gel column chromatography to give 9.76 g of the title compound as a white solid.

$^1$H NMR (CDCl$_3$): δ=0.82-0.95 (18H, m), 0.82-1.70 (57H, m), 1.10 (36H, s), 1.16 (36H, s), 2.05-2.29 (27H, m), 2.95-3.60 (18H, m), 5.00-5.25 (6H, m).

MS (FD, m/z): 1785.

Melting point: 144° C.

Example 4

Preparation of Compound Represented by Formula (5-4)

A mixture of 83.12 g of a solution of 1.46 g of tris(2-aminoethyl)amine and 20% 2-chloro-4,6-bis(N-(2,2,6,6-tetramethylpiperidin-4-yl)butylamino)-1,3,5-triazine in DMI and 120 mL of DMI was stirred at 180° C. for 8 hours. After the reaction mixture was left to stand to room temperature, 300 mL of water and 300 mL of ethyl acetate were added thereto and the mixture was neutralized by 4.28 g of potassium carbonate. The organic layer obtained by liquid separation was washed with a saturated aqueous NaCl solution and dried with anhydrous magnesium sulfate. After the solvent was distilled off, the concentrated residue was purified by silica gel column chromatography to give 6.05 g of the title compound as a pale yellow solid.

$^1$H NMR (CDCl$_3$): δ=0.90 (18H, t, J=6.5 Hz), 1.10-1.70 (48H, m), 1.13 (36H, s), 1.27 (36H, s), 2.65-2.80 (6H, m), 3.18-3.50 (18H, m), 5.24 (6H, br).

MS (FD, m/z): 1646.

Melting point: 109° C.

Example 5

Preparation of Compound Represented by Formula (5-5)

20.00 g of 2-chloro-4,6-bis(N-(1,2,2,6,6-pentamethylpiperidin-1-yl)butylamino)-1,3,5-triazine was added to a solution of 1.72 g of tris(2-aminoethyl)amine in DMI (80 mL) and the mixture was heated and stirred at 180° C. for 3 hours. 200 mL of ethyl acetate was added thereto and the mixture was washed with water. The organic layer obtained by liquid separation was dried with anhydrous magnesium sulfate and the solvent was distilled off under reduced pressure. The concentrated residue was purified by silica gel column chromatography to give 11.29 g of the title compound as a white solid.

$^1$H NMR (CDCl$^3$): δ=0.89 (18H, t, J=7.3 Hz), 1.00-1.70 (120H, m), 2.20-2.23 (18H, m), 2.63-2.72 (6H, m), 3.24-3.47 (18H, m), 5.00-5.23 (6H, m).

MS (FD, m/z): 1731.

Melting point: 113° C.

Example 6

Preparation of Compound Represented by Formula (5-6)

A mixture of 1.32 g of tris(3-aminopropyl)amine and 58.18 g of a 20% solution of 2-chloro-4,6-bis(N-(2,2,6,6-tetramethylpiperidin-4-yl)butylamino)-1,3,5-triazine in DMI was stirred at 180° C. for 8 hours. After the reaction mixture was left to stand to room temperature, 250 mL of water was added thereto and the mixture was neutralized by 3.00 g of potassium carbonate. This was extracted with ethyl acetate (250 mL) and after the organic layer was washed with a saturated aqueous NaCl solution, it was dried with anhydrous magnesium sulfate. The solvent was distilled off and the concentrated residue was purified by silica gel column chromatography to give 5.07 g of the title compound as a pale brown solid.

$^1$H NMR (CDCl$_3$): δ=0.91 (18H, t, J=6.5 Hz), 1.05-1.80 (54H, m), 1.13 (36H, s), 1.27 (36H, s), 2.45 (6H, s), 3.15-3.45 (18H, m), 5.24 (6H, br).

MS (FD, m/z): 1687.

Melting Point: 104° C.

Example 7

Preparation of Compound Represented by Formula (5-7)

A solution of 1.32 g of tris(3-aminopropyl)amine and 12.25 g of 2-chloro-4,6-bis(N-(1,2,2,6,6-pentamethylpiperidin-4-yl)butylamino-1,3,5-triazine in DMI (70 mL) was stirred at 170° C. for 5 hours. After the reaction mixture was left to stand to room temperature, 250 mL of water was added thereto and the mixture was neutralized by 3.00 g of potassium carbonate. This was extracted with ethyl acetate (250 mL) and after the organic layer was washed with a saturated aqueous NaCl solution, it was dried with anhydrous magnesium sulfate. The solvent was distilled off and the concentrated residue was purified by silica gel column chromatography to give 5.10 g of the title compound as a white solid.

$^1$H NMR (CDCl$_3$): δ=0.80-0.95 (18H, m), 1.00-1.80 (54H, m), 1.08 (36H, s), 1.17 (36H, s), 2.15-2.30 (18H, m), 2.37-2.50 (6H, m), 3.20-3.65 (18H, m), 4.90-5.30 (6H, m).

MS (FD, m/z): 1772.

Melting point: 115° C.

Example 8

Preparation of Compound Represented by Formula (5-8)

10.00 g of 2-chloro-4,6-bis(N-(2,2,6,6-tetramethylpiperidin-4-yl)butylamino)-1,3,5-triazine was added to a solution of 1.49 g of N,N,N',N'-tetrakis(3-aminopropyl)-1,4-butanediamine in DMI (60 mL) and the mixture was heated and stirred at 180° C. for 4 hours. After 200 mL of ethyl acetate was added to the reaction mixture and the mixture was washed with water, the organic layer obtained by liquid separation was dried with anhydrous magnesium sulfate. The solvent was distilled off and the concentrated residue was purified by silica gel column chromatography to give 6.35 g of the title compound as a white solid.

$^1$H NMR (CDCl$_3$): δ=0.85-0.97 (24H, m), 0.99-1.80 (76H, m), 1.13 (48H, s), 1.26 (48H, s), 2.30-2.50 (12H, m), 3.20-3.45 (24H, m), 5.10-5.39 (8H, m).

MS (FD, m/z): 2315.

Melting point: 107° C.

Example 9

Preparation of Compound Represented by Formula (5-9)

8.65 g of 2-chloro-4,6-bis(N-(2,2,6,6-tetramethylpiperidin-4-yl)butylamino)-1,3,5-triazine was added to a solution of 1.54 g of N,N,N',N'-tetrakis(3-(bis(3-aminopropyl)amino) propyl-1,4-butanediamine in DMI (70 mL) and the mixture was heated and stirred at 180° C. for 3 hours. After the reaction mixture was left to stand to room temperature, 200 mL of ethyl acetate and water were added to the reaction mixture and the mixture was neutralized by potassium carbonate. After the organic layer obtained by liquid separation was washed with a saturated aqueous NaCl solution, it was dried with anhydrous magnesium sulfate. The solvent was distilled off under reduced pressure and the obtained concentrated residue was purified by silica gel column chromatography to give 2.86 g of the title compound as a pale yellow solid.

$^1$H NMR (CDCl$_3$): δ=0.80-1.00 (48H, m), 1.00-1.95 (156H, m), 1.15 (96H, s), 1.29 (96H, s), 2.40-2.90 (36H, m), 3.20-3.70 (48H, m), 5.05-5.35 (16H, m).

Melting point: 76° C.

Example 10

Preparation of Compound Represented by Formula (5-10)

(1) Synthesis of N,N,N',N'-tetrakis(2-cyanoethyl) ethylenediamine 53.03 g of acrylonitrile was dropwise added to an aqueous solution (50 ml) of 12.01 g of ethylenediamine under room temperature over 2 hours and the mixture was stirred at 80° C. for 2 hours. After excessive acrylonitrile was distilled off under reduced pressure, 100 mL of ethyl acetate was added thereto and the mixture was washed with water. The organic layer obtained by liquid separation was dried with anhydrous magnesium sulfate and the solvent was distilled off to give 46.56 g of the title compound as a colorless oil.

$^1$H NMR (CDCl$_3$): δ=2.52 (8H, t, J=6.2 Hz), 2.72 (4H, s), 2.84-2.97 (8H, m).

(2) Synthesis of N,N,N',N'-tetrakis(3-aminopropyl) ethylenediamine 5.00 g of N,N,N',N'-tetrakis(2-cyanoethyl)ethylenediamine, 0.50 g of Raney Co and 50 mL of dioxane were charged in an autoclave and a hydrogenation reaction was carried out at an initial hydrogen pressure of 8.0 MPa at 100° C. for 2 hours. After the catalyst was removed by filtration, the filtrate was concentrated to dryness to give 5.09 g of the title compound as a pale red oil.

$^1$H NMR (CDCl$_3$): δ=1.53-1.69 (8H, m), 2.45-2.79 (20H, m).

GC-MS (m/z): 289.

(3) Synthesis of Compound Represented by Formula (5-10)

5.36 g of 2-chloro-4,6-bis(N-(2,2,6,6-tetramethylpiperidin-4-yl)butylamino)-1,3,5-triazine was added to a solution of 0.72 g of N,N,N',N'-tetrakis(3-aminopropyl)ethylenediamine in DMI (40 mL) and the mixture was heated and stirred at 180° C. for 5 hours. After the reaction mixture was left to stand to room temperature, 200 mL of ethyl acetate and water were added to the reaction mixture and the mixture was neutralized by potassium carbonate. After the organic layer obtained by liquid separation was washed with a saturated aqueous NaCl solution, it was dried with anhydrous magnesium sulfate. The solvent was distilled off under reduced pressure and the obtained concentrated residue was purified by silica gel column chromatography to give 3.81 g of the title compound as a pale yellow solid.

$^1$H NMR (CDCl$_3$): δ=0.80-0.97 (24H, m), 1.00-2.00 (72H, m), 1.13 (48H, s), 1.27 (48H, s), 2.35-2.80 (12H, m), 3.18-3.70 (24H, m), 5.24 (8H, br).

MS (FD, m/z): 2288.

Melting point: 91° C.

Example 11

Preparation of Compound Represented by Formula (5-11)

(1) Synthesis of N,N,N',N'-tetrakis(2-cyanoethyl)-1,3-propanediamine 158.63 g of acrylonitrile and 81.99 g of acetic acid were added to a solution of 22.49 g of 1,3-propanediamine in ethanol (300 mL) and the mixture was heated under reflux for 12 hours. After the reaction mixture was concentrated, 600 mL of water, 600 mL of ethyl acetate and 83.04 g of 28% ammonia water were added thereto and the mixture was stirred under room temperature. After the organic layer obtained by liquid separation was washed with water and dried with anhydrous magnesium sulfate, it was concentrated to dryness. The concentrated residue was purified by silica gel column chromatography to give 66.58 g of the title compound as a pale yellow oil.

$^1$H NMR (CDCl$_3$): δ=1.60-1.75 (2H, m), 2.52 (8H, t, J=6.6 Hz), 2.66 (4H, t, J=6.6 Hz), 2.86 (8H, t, J=6.6 Hz).

(2) Synthesis of N,N,N',N'-tetrakis(3-aminopropyl)-1,3-propanediamine 20.05 g of N,N,N',N'-tetrakis(2-cyanoethyl)-1,3-propanediamine, 2.01 g of Raney Co and 100 mL of 1,4-dioxane were charged in an autoclave and a hydrogenation reaction was carried out at an initial hydrogen pressure of 9.0 MPa at 150° C. for 3 hours. After the catalyst was removed by filtration, the obtained filtrate was concentrated to dryness to give 18.57 g of the title compound as a pale yellow oil.

$^1$H NMR (CDCl$_3$): δ=1.21 (8H, br), 1.50-1.68 (10H, m), 2.35-2.50 (12H, m), 2.71 (8H, t, J=6.9 Hz).

(3) Synthesis of Compound Represented by Formula (5-11)

A solution of 1.51 g of N,N,N',N'-tetrakis(3-aminopropyl)-1,3-propanediamine and 12.70 g of 2-chloro-4,6-bis(N-(1,2,2,6,6-pentamethylpiperidin-4-yl)butylamino)-1,3,5-triazine in DMI (100 mL) was stirred at 180° C. for 5 hours. After the reaction mixture was left to stand to room temperature, 200 mL of water and 200 mL of ethyl acetate were added to the reaction mixture and the mixture was neutralized by 3.46 g of potassium carbonate. After the organic layer obtained by liquid separation was washed with water, it was dried with anhydrous magnesium sulfate. After the solvent was distilled off, the concentrated residue was purified by silica gel column chromatography to give 1.90 g of the title compound as a white solid.

$^1$H NMR (CDCl$_3$): δ=0.90 (24H, t), 0.95-1.75 (74H, m), 1.08 (48H, s), 1.14 (48H, s), 2.23 (24H, s), 2.30-2.60 (12H, m), 3.15-3.40 (24H, m), 5.00-5.28 (8H, m).

MS (FD, m/z): 2413.

Melting point: 123° C.

Example 12

Preparation of Compound Represented by Formula (5-12)

(1) Synthesis of N,N,N',N'-tetrakis(2-cyanoethyl)-1,2-diaminopropane 196.92 g of acrylonitrile and 90.08 g of acetic acid were added dropwise to a solution of 22.24 g of 1,2-diaminopropane in ethanol (200 mL) over 30 minutes respectively and the mixture was heated under reflux for 15 hours. After the reaction mixture was concentrated, 500 mL of water, 600 mL of ethyl acetate and 36.49 g of 28% ammonia water were added thereto and the mixture was stirred under room temperature. After the organic layer obtained by liquid separation was washed with a saturated aqueous NaCl solution and dried with anhydrous magnesium sulfate, it was concentrated to dryness. The cconcentrated residue was purified by silica gel column chromatography to give 24.20 g of the title compound as a pale yellow oil.

$^1$H NMR (CDCl$_3$): δ=1.09 (3H, d, J=6.6 Hz), 2.35-2.45 (1H, m), 2.51 (8H, t, J=6.4 Hz), 2.77-2.88 (2H, m), 2.92 (8H, t, J=6.4 Hz).

(2) Synthesis of N,N,N',N'-tetrakis(3-aminopropyl)-1,2-diaminopropane 20.05 g of N,N,N',N'-tetrakis(2-cyanoethyl)-1,2-diaminopropane, 2.01 g of Raney Co and 100 mL of 1,4-dioxane were charged in an autoclave and a hydrogenation reaction was carried out at an initial hydrogen pressure of 9.0 MPa at 160° C. for 3 hours. After the catalyst was removed by filtration, the obtained filtrate was concentrated to dryness to give 20.52 g of the title compound as a white solid.

$^1$H NMR (CDCl$_3$): δ=0.96 (3H, d, J=6.6 Hz), 1.20 (8H, br), 1.50-1.70 (8H, m), 2.17-2.58 (11H, m), 2.62-2.80 (8H, m).

(3) Synthesis of Compound Represented by Formula (5-12)

A solution of 1.51 g of N,N,N',N'-tetrakis(3-aminopropyl)-1,2-diaminopropane and 2-chloro-4,6-bis(N-(1,2,2,6,6-pentamethylpiperidin-4-yl)butylamino)-1,3,5-triazine in DMI (100 mL) was stirred at 170° C. for 12 hours. After the reaction mixture was left to stand to room temperature, 200 mL of water and 200 mL of ethyl acetate were added to the reaction mixture and the mixture was neutralized by 3.46 g of potassium carbonate. After the organic layer obtained by liquid separation was washed with water, it was dried with anhydrous magnesium sulfate. After the solvent was distilled off, the concentrated residue was purified by silica gel column chromatography to give 2.46 g of the title compound as a white solid.

$^1$H NMR (CDCl$_3$): δ=0.75-0.95 (24H, m), 0.80-1.75 (75H, m), 1.08 (48H, s), 1.14 (48H, s), 2.15-2.60 (11H, m), 2.22 (24H, s), 3.15-3.45 (24H, m), 5.00-5.25 (8H, m).

MS (FD, m/z): 2414.

Melting point: 129° C.

Example 13

Preparation of Compound Represented by Formula (5-13)

(1) Synthesis of N,N,N',N'-tetrakis(2-cyanoethyl) dodecamethylenediamine 26.52 g of acrylonitrile was added dropwise to a mixed solution of 20.00 g of dodecyldiamine in water (25 mL)/ethanol (25 mL) at room temperature over 1 hour and the mixture was stirred at 80° C. for 3 hours. After the reaction mixture was concentrated, 100 mL of ethyl acetate was added thereto and the mixture was washed with water. The organic layer was dried with anhydrous magnesium sulfate and concentrated to dryness to give 36.7 g of the title compound as a colorless oil.

$^1$H NMR (CDCl$_3$): δ=1.21-1.33 (16H, m), 1.34-1.52 (4H, m), 2.44-2.55 (12H, m), 2.86 (8H, t, J=6.8 Hz).

(2) Synthesis of N,N,N',N'-tetrakis(3-aminopropyl) dodecamethylenediamine 5.00 g of N,N,N',N'-tetrakis(2-cyanoethyl)dodecamethylenediamine, 0.50 g of Raney Co and 50 mL of 1,4-dioxane were charged in an autoclave and a hydrogenation reaction was carried out at an initial hydrogen pressure of 8.0 MPa at 170° C. for 2 hours. After the catalyst was removed by filtration, the obtained filtrate was concentrated to dryness to give 5.08 g of the title compound as a pale red oil.

$^1$H NMR (CDCl$_3$): δ=1.21-1.33 (16H, m), 1.38-1.50 (4H, m), 1.49-1.63 (8H, m), 2.38 (4H, t, J=7.6 Hz), 2.45 (8H, t, J=7.3 Hz), 2.72 (8H, t, J=6.9 Hz).

(3) Synthesis of Compound Represented by Formula (5-13)

A solution of 1.07 g of N,N,N',N'-tetrakis(3-aminopropyl) dodecamethylenediamine and 5.36 g of 2-chloro-4,6-bis(N-(2,2,6,6-tetramethylpiperidin-4-yl)butylamino)-1,3,5-triazine in DMI (40 mL) was heated and stirred at 180° C. for 5 hours. After the reaction mixture was left to stand to room temperature, 200 mL of ethyl acetate and water were added to the reaction mixture and the mixture was neutralized by potassium carbonate. After the organic layer obtained by liquid separation was washed with a saturated aqueous NaCl solution, it was dried with anhydrous magnesium sulfate. The concentrated residue obtained by distilling off the solvent under reduced pressure was purified by silica gel column chromatography to give 1.41 g of the title compound as a white solid.

$^1$H NMR (CDCl$_3$): δ=0.80-0.97 (24H, m), 0.97-2.00 (92H, m), 1.15 (48H, s), 1.29 (48H, s), 2.22-2.95 (12H, m), 3.10-3.70 (24H, m), 5.05-5.40 (8H, m).

MS (FD, m/z): 2427.

Melting point: 71° C.

Example 14

Preparation of Compound Represented by Formula (5-14)

(1) Synthesis of N,N,N',N'-tetrakis(2-cyanoethyl)-1,3-bis(aminomethyl)cyclohexane 18.63 g of acrylonitrile was added dropwise to a mixed solution of 10.00 g of 1,3-bis(aminomethyl)cyclohexane in water (25 mL)/ethanol (25 mL) at room temperature over 2 hours and the mixture was stirred at 80° C. for 4 hours. After the reaction mixture was concentrated, 100 mL of ethyl acetate was added thereto and the mixture was washed with water. The organic layer was dried with anhydrous magnesium sulfate and concentrated to dryness to give 24.17 g of the title compound as a colorless oil.

$^1$H NMR (CDCl$_3$): δ=0.36-2.17 (10H, m), 2.27-2.41 (4H, m), 2.45-2.50 (8H, m), 2.80-2.91 (8H, m).

(2) Synthesis of N,N,N',N'-tetrakis(3-aminopropyl)-1,3-bis(aminomethyl)cyclohexane 5.00 g of N,N,N',N'-tetrakis(2-cyanoethyl)-1,3-bis(aminomethyl)cyclohexane, 0.50 g of Raney Co and 50 mL of 1,4-dioxane were charged in an autoclave and a hydrogenation reaction was carried out at an initial hydrogen pressure of 8.0 MPa at 180° C. for 2 hours. After the catalyst was removed by filtration, the obtained filtrate was concentrated to dryness to give 5.10 g of the title compound as a pale red oil.

$^1$H NMR (CDCl$_3$): δ=0.38-1.83 (18H, m), 2.11-2.26 (4H, m), 2.40 (8H, t, J=7.0 Hz), 2.72 (8H, t, J=6.9 Hz).

(3) Synthesis of Compound Represented by Formula (5-14)

A solution of 0.93 g of N,N,N',N'-tetrakis(3-aminopropyl)-1,3-bis(aminomethyl)cyclohexane and 5.36 g of 2-chloro-4,6-bis(N-(2,2,6,6-tetramethylpiperidin-4-yl)butylamino)-1,3,5-triazine in DMI (40 mL) was heated and stirred at 180° C. for 5 hours. After the reaction mixture was left to stand to room temperature, 200 mL of ethyl acetate and water were added to the reaction mixture and the mixture was neutralized by potassium carbonate. After the organic layer obtained by liquid separation was washed with a saturated aqueous NaCl solution, it was dried with anhydrous magnesium sulfate. The concentrated residue obtained by distilling off the solvent under reduced pressure was purified by silica gel column chromatography to give 1.82 g of the title compound as a white solid.

$^1$H NMR (CDCl$_3$): δ=0.80-0.95 (24H, m), 0.95-2.00 (82H, m), 1.13 (48H, s), 1.28 (48H, s), 2.30-2.80 (12H, m), 3.00-3.65 (24H, m), 5.10-5.36 (8H, m).

MS (FD, m/z): 2370.

Melting point: 111° C.

Example 15

Preparation of Compound Represented by Formula (5-15)

(1) Synthesis of 1,3-bis(N,N-bis(2-cyanoethyl)aminomethyl)benzene

A mixture of 6.81 g of m-xylilenediamine, 150 mL of acrylonitrile and 12.05 g of acetic acid was heated under reflux for 12 hours. After the reaction mixture was concentrated, 150 mL of water was added thereto and the mixture was neutralized by 28% ammonia water, followed by extraction of the mixture with ethyl acetate (200 mL). After the organic layer was washed with water and dried with anhydrous magnesium sulfate, it was concentrated to dryness to give 16.81 g of the title compound.

$^1$H NMR (CDCl$_3$): δ=2.49 (8H, t, J=6.7 Hz), 2.89 (8H, t, J=6.6 Hz), 3.72 (4H, s), 7.20-7.35 (3H, m), 7.49 (1H, s).

(2) Synthesis of 1,3-bis(N,N-bis(3-aminopropyl)aminomethyl)benzene 6.97 g of 1,3-bis(N,N-bis(2-cyanoethyl)aminomethyl) benzene, 0.70 g of Raney Co and 100 mL of 1,4-dioxane were charged in an autoclave and a hydrogenation reaction was carried out at an initial hydrogen pressure of 9.0 MPa at 180° C. for 2 hours. After the catalyst was removed by filtration, the obtained filtrate was concentrated to dryness to give 6.88 g of the title compound.

$^1$H NMR (CDCl$_3$): δ=1.09 (8H, br), 1.52-1.70 (8H, m), 2.45 (8H, t, J=6.9 Hz), 2.70 (8H, t, J=6.9 Hz), 3.51 (4H, s), 7.15-7.30 (4H, s).

(3) Synthesis of Compound Represented by Formula (5-15)

A mixture of 2.19 g of 1,3-bis(N,N-bis(3-aminopropyl) aminomethyl)benzene and 64.35 g of a solution of 20% 2-chloro-4,6-bis(N-(2,2,6,6-tetramethylpiperidin-4-yl)butylamino)-1,3,5-triazine in DMI was stirred at 180° C. for 8 hours. After the reaction mixture was left to stand to room temperature, 300 mL of water and 300 mL of ethyl acetate were added to the reaction mixture and the mixture was neutralized by 3.33 g of potassium carbonate. The organic layer obtained by liquid separation was washed with a saturated aqueous NaCl solution and dried with anhydrous magnesium sulfate. After the solvent was distilled off, the concentrated residue was purified by silica gel column chromatography to give 8.54 g of the title compound as a pale brown solid.

$^1$H NMR (CDCl$_3$): δ=0.75-0.97 (24H, m), 0.99-1.80 (72H, m), 1.06 (48H, s), 1.26 (48H, s), 2.42 (8H, br), 3.15-3.80 (28H, m), 5.00-5.45 (8H, m), 7.10-7.28 (4H, m).

MS (FD, m/z): 2364.

Melting point: 116° C.

Example 16

Preparation of Compound Represented by Formula (5-16)

(1) Synthesis of 1,4-bis(N,N-bis(2-cyanoethyl)aminomethyl)benzene 18.57 g of acrylonitrile was added dropwise to an aqueous solution (80 mL) of 6.81 g of p-xylilenediamine at room temperature over 1 hour. After the mixture was stirred at an internal temperature of 70° C. for 12 hours, the reaction mixture was concentrated and 100 mL of water was added thereto, followed by extraction of the mixture with ethyl acetate (150 mL). After the organic layer was washed with water and dried with anhydrous magnesium sulfate, it was concentrated to dryness to give 16.27 g of the title compound as a white solid.

$^1$H NMR (CDCl$_3$): δ=2.47 (8H, t, J=6.8 Hz), 2.91 (8H, t, J=6.8 Hz), 3.72 (4H, s), 7.21-7.34 (4H, m).

(2) Synthesis of 1,4-bis(N,N-bis(3-aminopropyl)aminomethyl)benzene 6.97 g of 1,4-bis(N,N-bis(2-cyanoethyl)aminomethyl) benzene, 0.70 g of Raney Co and 100 mL of 1,4-dioxane were charged in an autoclave and a hydrogenation reaction was carried out at an initial hydrogen pressure of 9.0 MPa at 180° C. for 2 hours. After the catalyst was removed by filtration, the obtained filtrate was concentrated to dryness to give 7.00 g of the title compound.

$^1$H NMR (CDCl$_3$): δ=1.09 (8H, br), 1.55-1.65 (8H, m), 2.44 (8H, t, J=6.9 Hz), 2.70 (8H, t, J=6.8 Hz), 3.50 (4H, s), 7.24 (4H, s).

(3) Synthesis of Compound Represented by Formula (5-16)

A mixture of 1.46 g of 1,4-bis(N,N-bis(3-aminopropyl) aminomethyl)benzene and 45.05 g of a solution of 20% 2-chloro-4,6-bis(N-(2,2,6,6-tetramethylpiperidin-4-yl)butylamino)-1,3,5-triazine in DMI was stirred at 180° C. for 6 hours. After the reaction mixture was left to stand to room temperature, 200 mL of water and 200 mL of ethyl acetate were added to the reaction mixture and the mixture was neutralized by 2.38 g of potassium carbonate. The organic layer obtained by liquid separation was washed with a saturated aqueous NaCl solution and dried with anhydrous magnesium sulfate. After the solvent was distilled off, the concentrated residue was purified by silica gel column chromatography to give 6.05 g of the title compound as a pale brown solid.

$^1$H NMR (CDCl$_3$): δ=0.90 (24H, t, J=6.8 Hz), 0.98-1.82 (72H, m), 1.13 (48H, s), 1.21 (48H, s), 2.46 (8H, br), 3.15-3.60 (28H, m), 4.98-5.35 (8H, m), 7.05-7.28 (4H, m).

MS (FD, m/z): 2364.

Melting point: 115° C.

Example 17

Preparation of Compound Represented by Formula (5-17)

(1) Synthesis of N,N,N'N-tetrakis(2-cyanoethyl)-3,9-bis(aminopropyl)-2,4,8,10-tetraoxaspiro[5.5]undecane 26.52 g of acrylonitrile was added dropwise to a mixed solution of 27.4 g of 3,9-bis(aminopropyl)-2,4,8,10-tetraoxaspiro[5.5]undecane in water (25 mL)/ethanol (25 mL) at room temperature over 1 hour and the mixture was stirred at 80° C. for 3 hours. After the reaction mixture was concentrated, 100 mL of ethyl acetate was added thereto and the mixture was washed with water. The organic layer was dried with anhydrous magnesium sulfate and concentrated to dryness to give 46.8 g of the title compound as a colorless oil.

$^1$H NMR (CDCl$_3$): δ=1.54-1.70 (8H, m), 2.47 (8H, t, J=6.8 Hz), 2.56 (4H, t, J=6.9 Hz), 2.86 (8H, t, J=6.9 Hz), 3.33-3.37 (2H, m), 3.51-3.59 (4H, m), 4.48-4.54 (4H, m).

(2) Synthesis of N,N,N',N'-tetrakis(3-aminopropyl)-3,9-bis(aminopropyl)-2,4,8,10-tetraoxaspiro[5.5] undecane 5.00 g of N,N,N'N-tetrakis(2-cyanoethyl)-3,9-bis(aminopropyl)-2,4,8,10-tetraoxaspiro[5.5]undecane, 0.50 g of Raney Co and 50 mL of 1,4-dioxane were charged in an autoclave and a hydrogenation reaction was carried out at an initial hydrogen pressure of 8.0 MPa at 180° C. for 2 hours. After the catalyst was removed by filtration, the obtained filtrate was concentrated to dryness to give 5.01 g of the title compound as a pale red oil.

$^1$H NMR (CDCl$_3$): δ=1.52-1.62 (16H, m), 2.36-2.46 (12H, m), 2.71 (8H, t, J=7.0 Hz), 3.31-3.35 (2H, m), 3.53-3.59 (4H, m), 4.43-4.55 (4H, m).

(3) Synthesis of Compound Represented by Formula (5-17)

A solution of 1.26 g of N,N,N',N'-tetrakis(3-aminopropyl)-3,9-bis(aminopropyl)-2,4,8,10-tetraoxaspiro[5.5]undecane and 5.36 g of 2-chloro-4,6-bis(N-(2,2,6,6-tetramethylpiperidin-4-yl)butylamino)-1,3,5-triazine in DMI (40 mL) was heated and stirred at 180° C. for 5 hours. After the reaction mixture was left to stand to room temperature, 200 mL of ethyl acetate and water were added to the reaction mixture and the mixture was neutralized by potassium carbonate. After the organic layer obtained by liquid separation was washed with a saturated aqueous NaCl solution, it was dried with anhydrous magnesium sulfate. The concentrated residue obtained by distilling off the solvent under reduced pressure was purified by silica gel column chromatography to give 3.44 g of the title compound as a pale yellow solid.

$^1$H NMR (CDCl$_3$): δ=0.90-0.98 (24H, m), 0.98-1.95 (80H, m), 1.14 (48H, s), 1.28 (48H, s), 2.30-2.60 (12H, m), 3.10-3.70 (32H, m), 4.05-4.60 (2H, m), 5.22 (8H, br).

MS (FD, m/z): 2501.

Melting point: 99° C.

Example 18

Preparation of Compound Represented by Formula (5-18)

(1) Synthesis of N,N-bis(2-cyanoethyl)benzylamine 18.58 g of acrylonitrile was added dropwise to an aqueous solution (80 mL) of 10.71 g of benzylamine at room temperature over 1 hour and 20 minutes. Thereafter, the mixture was heated and stirred at 70° C. for 8 hours. After the reaction mixture was concentrated to dryness, 100 mL of water was added thereto, followed by extraction of the mixture with ethyl acetate (150 mL). After the organic layer obtained was washed with water, it was dried with anhydrous magnesium sulfate. The solvent was distilled off to give 19.93 g of the title compound as a colorless oil.

$^1$H NMR (CDCl$_3$): δ=2.45 (4H, t, J=6.8 Hz), 2.91 (4H, t, 6.8 Hz), 3.72 (2H, s), 7.30-7.36 (5H, m).

(2) Synthesis of N,N-bis(3-aminopropyl)benzylamine 8.53 g of N,N-bis(2-cyanoethyl)benzylamine, 0.72 g of Raney Co and 100 mL of methanol were charged in an autoclave and a hydrogenation reaction was carried out at an initial hydrogen pressure of 9.0 MPa at 100° C. for 1 hour. After the catalyst was removed by filtration, the obtained filtrate was concentrated to dryness to give 8.69 g of the title compound as a pale yellow oil.

$^1$H NMR (CDCl$_3$): δ=1.50-1.78 (4H, m), 2.31 (4H, s), 2.45 (4H, t, J=6.9 Hz), 2.71 (4H, t, J=6.8 Hz), 3.58 (2H, s), 7.17-7.50 (5H, m).

(3) Synthesis of N,N-bis(3-(N,N-bis(2-cyanoethyl)amino)propyl)benzylamine 4.43 g of acetic acid was added to 4.00 g of N,N-bis(3-aminopropyl)benzylamine and 100 mL of acrylonitrile and the mixture was heated under reflux for 14 hours. After the reaction mixture was concentrated, 150 mL of water was added thereto and the mixture was neutralized by 4.60 g of 28% ammonia water, followed by extraction of the mixture with ethyl acetate (150 mL). After the organic layer was washed with water, it was dried with anhydrous magnesium sulfate. The solvent was distilled off to give 6.59 g of the title compound as a colorless oil.

$^1$H NMR (CDCl$_3$): δ=1.50-1.70 (4H, m), 2.35-2.65 (16H, m), 2.70-2.95 (8H, m), 3.54 (2H, s), 7.20-7.45 (5H, m).

(4) Synthesis of N,N-bis(3-(N,N-bis(3-aminopropyl)amino)propyl)benzylamine 6.50 g of N,N-bis(3-(N,N-bis(2-cyanoethyl)amino)propyl)benzylamine, 0.65 g of Raney Co and 100 mL of 1,4-dioxane were charged in an autoclave and a hydrogenation reaction was carried out at an initial hydrogen pressure of 9.0 MPa at 180° C. for 2 hours. After the catalyst was removed by filtration, the obtained filtrate was concentrated to dryness to give 6.16 g of the title compound as a pale yellow oil.

$^1$H NMR (CDCl$_3$): δ=1.18 (8H, br), 1.40-1.80 (12H, m), 2.25-2.50 (16H, m), 2.50-2.90 (8H, m), 3.53 (2H, s), 7.15-7.40 (5H, m).

(5) Synthesis of Compound Represented by Formula (5-18)

A mixture of 2.70 g of N,N-bis(3-N,N-bis(3-aminopropyl)amino)benzylamine and 67.03 g of a solution of 20% 2-chloro-4,6-bis(N-(2,2,6,6-tetramethylpiperidin-4-yl)butylamino)-1,3,5-triazine in DMI was stirred at 180° C. for 8 hours. After the reaction mixture was left to stand to room temperature, 300 mL of water and 300 mL of ethyl acetate were added to the reaction mixture and the mixture was neutralized by 3.46 g of potassium carbonate. After the organic layer obtained by liquid separation was washed with a saturated aqueous NaCl solution, it was dried with anhydrous magnesium sulfate. The solvent was distilled off and the concentrated residue was purified by silica gel column chromatography to give 3.41 g of the title compound as a pale brown solid.

$^1$H NMR (CDCl$_3$): δ=0.80-1.00 (24H, m), 1.00-1.90 (76H, m), 1.13 (48H, s), 1.27 (48H, s), 2.30-2.50 (16H, m), 3.10-3.65 (26H, m), 5.05-5.35 (8H, m), 7.10-7.35 (5H, m).

MS (FD, m/z): 2449.

Melting point: 97° C.

Example 19

Preparation of Compound Represented by Formula (5-19)

A solution of 2.53 g of N,N,N',N'-tetrakis(3-aminopropyl)-1,4-butanediamine and 18.51 g of 2-chloro-4,6-bis(N-(1,2,2,6,6-pentamethylpiperidin-4-yl)butylamino)-1,3,5-triazine in DMI (80 mL) was stirred at 160° C. for 4 hours and at 170° C. for 3 hours. After the reaction mixture was left to stand to room temperature, 250 mL of water was added thereto and the mixture was neutralized by 4.53 g of potassium carbonate. This was extracted with ethyl acetate (250 mL) and after the organic layer was washed with a saturated aqueous NaCl solution, it was dried with anhydrous magnesium sulfate. After the solvent was distilled off, the concentrated residue was purified by silica gel column chromatography to give 6.41 g of the title compound as a white solid.

$^1$H NMR (CDCl$_3$): δ=0.83-0.95 (24H, m), 1.00-1.80 (76H, m), 1.08 (48H, s), 1.15 (48H, s), 2.23 (24H, s), 2.30-2.60 (12H, m), 3.20-3.45 (24H, m), 5.05-5.37 (8H, m).

MS (FD, m/z): 2427.

Melting point: 124° C.

Example 20

Preparation of Compound Represented by Formula (5-20)

11.29 g of 2-chloro-4,6-bis(N-(1,2,2,6,6-pentamethylpiperidin-4-yl)butylamino)-1,3,5-triazine and 3.46 g of potassium carbonate were added to a solution of 1.01 g of N,N,N',N'-tetrakis(3-aminopropyl)ethylenediamine in DMI (80 mL) and the mixture was heated and stirred at 160° C. for 40 hours. After the reaction mixture was left to stand to room temperature, 150 mL of ethyl acetate and 150 mL of water were added thereto and the organic layer obtained by liquid separation was washed with water. After it was dried with anhydrous magnesium sulfate, the solvent was distilled off under reduced pressure. The obtained concentrated residue was purified by silica gel column chromatography to give 1.82 g of the title compound as a pale yellow solid.

$^1$H NMR (CDCl$_3$): δ=0.80-0.97 (24H, m), 0.98-1.80 (72H, m), 1.08 (48H, s), 1.55 (48H, s), 2.22 (24H, m), 2.35-3.45 (36H, m), 4.90-5.35 (12H, br).

MS (FD, m/z): 2400.

Melting point: 108° C.

Example 21

Preparation of Compound Represented by Formula (5-21)

7.23 g of 2-chloro-4,6-bis(N-(2,2,6,6-tetramethylpiperidin-4-yl)butylamino)-1,3,5-triazine and 2.07 g of potassium carbonate were added to a solution of 0.91 g of N,N,N',N'-tetrakis(3-aminopropyl)propanediamine in DMI (60 mL) and the mixture was heated and stirred at 130° C. for 20 hours. After the reaction mixture was left to stand to room temperature, 100 mL of ethyl acetate and 100 mL of water were added thereto and the organic layer obtained by liquid separation was washed with water. Subsequently, the organic layer was extracted with 1% hydrochloric acid and ethyl acetate was added to the obtained aqueous layer, followed by neutralization of the mixture with potassium carbonate. After the organic layer obtained by liquid separation was washed with water, it was dried with anhydrous magnesium sulfate. The solvent was distilled off under reduced pressure and the concentrated residue was purified by silica gel column chromatography to give 4.23 g of the title compound as a pale yellow solid.

$^1$H NMR (CDCl$_3$): δ=0.91 (24H, t), 0.95-1.75 (74H, m), 1.13 (48H, s), 1.27 (48H, s), 2.30-2.60 (12H, m), 3.15-3.45 (24H, m), 5.00-5.40 (8H, m).

MS (FD, m/z): 2302.

Melting point: 105° C.

Example 22

Preparation of Compound Represented by Formula (5-22)

(1) Synthesis of N,N,N',N'-tetrakis(2-cyanoethyl)-1,6-hexanediamine 53.60 g of acrylonitrile and 30.03 g of acetic acid were successively added dropwise and charged to a solution of 11.62 g of 1,6-hexanediamine in ethanol (70 mL) respectively. After the mixture was heated under reflux for 11 hours, the reaction mixture was concentrated. 200 mL of water, 200 mL of ethyl acetate and 27.37 g of 28% ammonia water were added thereto and the mixture was stirred at room temperature. After the organic layer obtained by liquid separation was washed with water and dried with anhydrous magnesium sulfate, it was concentrated to dryness. The concentrated residue was purified by silica gel column chromatography to give 29.15 g of the title compound.

$^1$H NMR (CDCl$_3$): δ=1.30-1.43 (4H, m), 1.43-1.58 (4H, m), 2.40-2.60 (12H, m), 2.85 (8H, t, J=6.8 Hz).

(2) Synthesis of N,N,N',N'-tetrakis(3-aminopropyl)-1,6-hexanediamine 16.42 g of N,N,N',N'-tetrakis(2-cyanoethyl)-1,6-hexanediamine, 1.64 g of Raney Co and 90 mL of 1,4-dioxane were charged in an autoclave and a hydrogenation reaction was carried out at an initial hydrogen pressure of 9.0 MPa at 180° C. for 2.5 hours. After the catalyst was removed by filtration, the obtained filtrate was concentrated to dryness to give 15.24 g of the title compound.

$^1$H NMR (CDCl$_3$): δ=1.10-1.50 (8H, m), 1.50-1.73 (8H, m), 2.30-2.53 (12H, m), 2.72 (8H, t, J=6.8 Hz).

(3) Synthesis of Compound Represented by Formula (5-22)

3.46 g of potassium carbonate was added to a solution of 1.72 g of N,N,N',N'-tetrakis(3-aminopropyl)-1,6-hexanediamine and 11.49 g of 2-chloro-4,6-bis(N-(2,2,6,6-tetramethylpiperidin-4-yl)butylamino)-1,3,5-triazine in DMI (80 mL) and the mixture was stirred at 130° C. for 15 hours. After the reaction mixture was left to stand to room temperature, 150 mL of water and 150 mL of ethyl acetate were added to the reaction mixture. The organic layer obtained by liquid separation was washed with water and dried with anhydrous magnesium sulfate. After the solvent was distilled off, the concentrated residue was purified by silica gel column chromatography to give 6.22 g of the title compound as a white solid.

$^1$H NMR (CDCl$_3$): δ=0.91 (24H, t), 0.97-1.78 (80H, m), 1.13 (48H, s), 1.27 (48H, s), 2.30-2.60 (12H, m), 3.15-3.45 (24H, m), 5.10-5.48 (8H, m).

MS (FD, m/z): 2344.

Melting point: 101° C.

Example 23

Preparation of Compound Represented by Formula (5-23)

3.46 g of potassium carbonate was added to a solution of 1.72 g of N,N,N',N'-tetrakis(3-aminopropyl)-1,6-hexanediamine and 11.28 g of 2-chloro-4,6-bis(N-(1,2,2,6,6-pentamethylpiperidin-4-yl)butylamino-1,3,5-triazine in DMI (80 mL) and the mixture was stirred at 130° C. for 16 hours. After the reaction mixture was left to stand to room temperature, 150 mL of water and 150 mL of ethyl acetate were added thereto. The organic layer obtained by liquid separation washed with water and dried with anhydrous magnesium sulfate. After the solvent was distilled off, the concentrated residue was purified by silica gel column chromatography to give 4.42 g of the title compound as a white solid.

$^1$H NMR (CDCl$_3$): δ=0.91 (24H, t), 0.97-1.78 (80H, m), 1.09 (48H, s), 1.15 (48H, s), 2.24 (24H, s), 2.30-2.60 (12H, m), 3.15-3.45 (24H, m), 4.90-5.40 (8H, m).

MS (FD, m/z): 2456.

Melting point: 111° C.

Example 24

Preparation of Compound Represented by Formula (5-24)

64.43 g of a solution of 18% 2-chloro-4,6-bis(N-2,2,6,6-tetramethylpiperidin-4-yl)butylamino)-1,3,5-triazine in DMI and 1.75 g sodium hydroxide powder were added to a solution of 0.64 g of glycerine in mesitylene (50 mL) and the mixture was heated and stirred at 180° C. for 4 hours while removing water by azeotrope. After the solvent was distilled off under reduced pressure, 100 mL of water and 100 mL of ethyl acetate were added thereto and the organic layer was obtained by liquid separation. The organic layer was washed with water and dried with anhydrous magnesium sulfate and the solvent was distilled off under reduced pressure. The concentrated residue was purified by silica gel column chromatography to give 8.16 g of the title compound as a pale yellow solid.

$^1$H NMR (CDCl$_3$): δ=0.93 (18H, t, J=7.3 Hz), 0.98-1.70 (48H, m), 1.11 (36H, s), 1.30 (36H, s), 3.20-3.39 (12H, m), 4.10-4.90 (5H, m), 5.00-5.72 (6H, m).

MS (FD, m/z): 1591.

Melting point: 110° C.

Example 25

Preparation of Compound Represented by Formula (5-25)

50 mL of xylene, 1.60 g of sodium hydroxide powder and 15.00 g of 2-chloro-4,6-bis(N-(1,2,2,6,6-pentamethylpiperidin-1-yl)butylamino)-1,3,5-triazine were added to a solution of 0.815 g of glycerine and the mixture was heated and stirred at 150° C. for 4 hours while removing water by azeotropic procedure. 200 mL of ethyl acetate was added thereto and after washed with water, the organic layer obtained by liquid separation was dried with anhydrous magnesium sulfate. The solvent was distilled of under reduced pressure and the concentrated residue was purified by silica gel column chromatography to give 8.65 g of the title compound as a white solid.

$^1$H NMR (CDCl$_3$): δ=0.88 (18H, t, J=7.6 Hz), 0.99-1.70 (120H, m), 2.10-2.30 (18H, m), 3.27-3.39 (12H, m), 4.20-4.90 (6H, m).

MS (FD, m/z): 1676.

Melting point: 134° C.

Example 26

Preparation of Compound Represented by Formula (5-26)

A mixture of 32.50 g of a solution of 0.51 g of 95% 1,1,1-tris(hydroxymethyl)ethane and 20% 2-chloro-4,6-bis(N-(2,2,6,6-tetramethylpiperidin-4-yl)butylamino)-1,3,5-triazine in DMI, 30 mL of mesitylene and 1.00 g of sodium hydroxide powder was dehydrated with azeotropic procedure at 180° C. for 8 hours. After the solvent was distilled off, 100 mL of water was added to the concentrated residue and the mixture was extracted with ethyl acetate (100 mL). After the organic layer obtained by liquid separation was washed with water, it was dried with anhydrous magnesium sulfate. After the solvent was distilled off, the concentrated residue was purified by silica gel column chromatography to give 1.57 g of the title compound as a white solid.

$^1$H NMR (CDCl$_3$): δ=0.93 (21H, m), 1.00-1.75 (48H, m), 1.15 (36H, s), 1.30 (36H, s), 3.17-3.40 (12H, m), 4.10-4.90 (6H, m), 5.00-5.30 (6H, m).

MS (FD, m/z): 1620.

Melting point: 151° C.

Example 27

Preparation of Compound Represented by Formula (5-27)

64.43 g of 18% 2-chloro-4,6-bis(N-(2,2,6,6-tetramethylpiperidin-4-yl)butylamino)-1,3,5-triazine in DMI and 1.75 g of sodium hydroxide powder were added to a solution of 0.78 g of 1,2,4-butanetriol in mesitylene (50 mL) and the mixture was heated and stirred at 180° C. for 2 hours while removing water by azeotrope. After the solvent was distilled off under reduced pressure, 100 mL of water and 100 mL of ethyl acetate were added thereto and the organic layer was obtained by liquid separation. The organic layer and washed with water and dried with anhydrous magnesium sulfate and the solvent was distilled off under reduced pressure. The concentrated residue was purified by silica gel column chromatography to give 8.86 g of the title compound as a pale yellow solid.

$^1$H NMR (CDCl$_3$): δ=0.93 (18H, t, J=7.3 Hz), 0.98-1.70 (50H, m), 1.12 (36H, s), 1.30 (36H, s), 3.10-3.38 (12H, m), 4.05-4.85 (5H, m), 5.00-5.35 (6H, m).

MS (FD, m/z): 1605.

Melting point: 107° C.

Example 28

Preparation of Compound Represented by Formula (5-28)

A mixture of 23.01 g of a solution of 0.34 g of 1,2,6-hexanetriol and 18% 2-chloro-4,6-bis(N-(2,2,6,6-tetramethylpiperidin-4-yl)butylamino)-1,3,5-triazine in DMI, 0.60 g of sodium hydroxide powder and 18 mL of mesitylene was heated under reflux for 3 hours while carrying out dehydration with azeotropic procedure. After DMI and mesitylene were distilled off, 35 mL of water was added thereto and the mixture was extracted with ethyl acetate. After the organic layer was washed with water, it was dried with anhydrous magnesium sulfate and the solvent was distilled off. The concentrated residue was purified by silica gel column chromatography to give 1.63 g of the title compound as a white solid.

$^1$H NMR (CDCl$_3$): δ=0.92 (18H, t, J=7.3 Hz), 1.05-1.73 (54H, m), 1.15 (36H, s), 1.23 (36H, m), 3.23-3.39 (12H, m), 4.05-4.70 (5H, m), 5.00-5.40 (6H, m).

MS (FD, m/z): 1633.

Melting point: 105° C.

Example 29

Preparation of Compound Represented by Formula (5-29)

61.11 g of a solution of 18% 2-chloro-4,6-bis(N-(2,2,6,6-tetramethylpiperidin-4-yl)butylamino)-1,3,5-triazine in DMI and 1.67 g of sodium hydroxide powder were added to a solution of 0.68 g of pentaerythritol in mesitylene (50 mL) and the mixture was heated and stirred at 180° C. for 3 hours while removing water by azeotropic procedure. After the solvent was distilled off under reduced pressure, 100 mL of water and 100 mL of ethyl acetate were added thereto and the organic layer was obtained by liquid separation. The organic layer was washed with water and dried with anhydrous magnesium sulfate and the solvent was distilled off under reduced pressure. The concentrated residue was purified by silica gel column chromatography to give 6.68 g of the title compound as a pale yellow solid.

$^1$H NMR (CDCl$_3$): δ=0.93 (24H, t, J=7.0 Hz), 0.97-1.70 (64H, m), 1.15 (48H, s), 1.30 (48H, s), 3.17-3.39 (16H, m), 4.40-4.90 (8H, m), 5.00-5.30 (8H, m).

MS (FD, m/z): 2135.

Melting point: 115° C.

Example 30

Preparation of Compound Represented by Formula (5-30)

A mixture of 8.54 g of the compound synthesized in Example 29, 25.97 g of 37% formaline and 15.03 g of 98% formic acid was heated under reflux for 12 hours. After the reaction mixture was concentrated, 200 mL of water and potassium carbonate were added thereto to neutralize it, followed by extraction of the mixture with ethyl acetate (300 mL). The organic layer was washed with a saturated aqueous NaCl solution and dried with anhydrous magnesium sulfate, followed by distilling off of the solvent under reduced pressure. The concentrated residue was purified by silica gel column chromatography to give 5.59 g of the title compound as a white solid.

$^1$H NMR (CDCl$_3$): δ=0.80-0.95 (24H, m), 0.95-1.80 (64H, m), 1.12 (48H, s), 1.17 (48H, s), 2.15-2.30 (24H, m), 3.17-3.32 (16H, m), 4.40-4.80 (8H, m), 4.80-5.30 (8H, m).

MS (FD, m/z): 2247.

Melting point: 134° C.

Example 31

Evaluation of Weather Resistance in Polypropylene Resin 0.10 part by weight of the compound obtained in Example as a light stabilizer or a condensation product of N,N'-bis(2,2,6,6-tetramethyl-4-piperidyl)hexamethylenediamine with 4-tert-octylamino-2,6-dichloro-1,3,5-s-triazine (trade name "CHIMASSORB 944", manufactured by Ciba Specialty Chemicals, Inc.) i.e., a light stabilizer as a comparative example and 0.10 part by weight of pentaerythrityl-tetrakis-3-(3,5-di-tert-butyl-4-hydroxyphenyl)propionate (trade name "IRGANOX 1010" manufactured by Ciba Specialty Chemicals, Inc.) as an anti-oxidant relative to 100 parts by weight of unstabilized polypropylene (trade name "Mitsui Polypro™ J707P", manufactured by Mitsui Kagaku Co., Ltd.) were uniformly mixed in a V type mixer. The obtained mixture was granulated by a biaxial extruder and the granulated article was molded to a flat plate of 2 mm×50 mm×70 mm by an injection molding machine. The samples were exposed to a xenon wetherometer and periodically taken out and the surface was observed by a microscope (magnification: 200 times) to give a crack generation time. The obtained results are shown in Table 1.

(1) Apparatus model used in exposure test: manufactured by Atlas Inc., xenon wetheometer Ci4000, water spray 18 minutes/120 minutes, black panel temperature: 83±3° C.

TABLE 1

| Number | Light stabilizer | Crack generation time (hrs) |
| --- | --- | --- |
| 1 | non-addition | 200 |
| 2 | CHIMASSORB 944 | 800 |
| 3 | Compound of Formula (5-1) | 1000 |
| 4 | Compound of Formula (5-2) | 1100 |
| 5 | Compound of Formula (5-3) | 1200 |
| 6 | Compound of Formula (5-4) | 1000 |
| 7 | Compound of Formula (5-5) | 1200 |
| 8 | Compound of Formula (5-6) | 1000 |
| 9 | Compound of Formula (5-7) | 1200 |
| 10 | Compound of Formula (5-8) | 1000 |

As can be seen from Table 1, it is understood that the compound of the present invention has an excellent improvement effect of weather resistance stability as compared with the comparative compound.

Example 32

Evaluation of Weather Resistance in Linear Low Density Polyethylene Resin 0.10 part by weight of the compound obtained in Example as a light stabilizer or bis(2,2,6,6-tetramethyl-piperidyl)sebacate (trade name "SANOL LS-770", manufactured by Sankyo Life Tech Co., Ltd.) and tetrakis(1,2,2,6,6-pentamethyl-4-piperidyl)-1,2,3,4-butanetetracarboxylate (trade name "Adekastab LA-52", manufactured by Asahi Denka Inc.), i.e., light stabilizers as Comparative example and 0.20 part by weight of octadecyl-3-(3,5-di-tert-butyl-4-hydroxyphenyl)propionate (trade name "IRGANOX 1076", manufactured by Ciba Specialty Chemicals, Inc.) as an antioxidant were mixed relative to 100 parts by weight of linear low density polyethylene (trade name "L-LDPE ULTZEX 2-21 L", manufactured by Mitsui Kagaku Co., Ltd.) and after the mixture was kneaded at 200° for 10 minutes using a labo plastomill (manufactured by Toyo Seiki Seisakusho Inc.), it was rolled to a sheet-like shape by a water-cooling type press machine. A part of the sheet was pressure-molded at 220° C. for 6 minutes to give the film-like test piece having a thickness of 0.1 mm. The obtained film was exposed into a xenon wetherometer and a tensile rupture elongation ratio was periodically measured to make it as an index of deterioration. Determination of deterioration showed 50% reduction time of the initial elongation value as a deterioration time. The obtained results are shown in Table 2.

(1) Apparatus model used in exposure test: manufactured by Atlas Inc., xenon wetherometer Ci4000, water spray 18 minutes/120 minutes, black panel temperature: 83±3° C.
(2) kind of machine used in tensil strength test: manufactured by Shimadzu Seisakusho Co., Ltd., Shimadzu auto graph AGS-500D
(3) test condition: cross head speed 120 mm/minute, distance between chucks=25 mm

TABLE 2

| Number | Light stabilizer | Deterioration time (hrs) |
| --- | --- | --- |
| 1 | non-addition | 330 |
| 2 | SANOL LS-770 | 370 |
| 3 | Adekastab LA-52 | 550 |
| 4 | Compound of Formula (5-1) | 1040 |
| 5 | Compound of Formula (5-2) | 880 |
| 6 | Compound of Formula (5-3) | 1150 |
| 7 | Compound of Formula (5-4) | 900 |
| 8 | Compound of Formula (5-5) | 1020 |
| 9 | Compound of Formula (5-6) | 980 |
| 10 | Compound of Formula (5-7) | 890 |
| 11 | Compound of Formula (5-8) | 1050 |
| 12 | Compound of Formula (5-29) | 960 |
| 13 | Compound of Formula (5-30) | 1210 |
| 14 | Compound of Formula (5-24) | 1020 |

As can be seen from Table 2, the compound of the present invention has an excellent improvement effect of weather resistance stability as compared with the comparative compound.

Example 33

Evaluation of Heat Resistance in Polypropylene Resin 0.25 part by weight of the compound obtained in Example as a light stabilizer or (2,2,6,6-tetramethyl-piperidyl)sebacate (trade name "SANOL LS-770", manufactured by Sankyo Life Tech Co., Ltd.), i.e., light stabilizers as Comparative example and 0.20 part by weight of octadecyl-3-(3,5-di-tert-butyl-4-hydroxyphenyl)propionate (trade name "IRGANOX 1076", manufactured by Ciba Specialty Chemicals, Inc.) as an antioxidant were mixed relative to 100 parts by weight of unstabilized polypropylene (trade name "Mitsui Polypro™ J105P", manufactured by Mitsui Kagaku Co., Ltd.) and after the mixture was kneaded at 200° for 10 minutes using a labo plastomill (manufactured by Toyo Seiki Seisakusho Inc.), it was rolled to a sheet-like shape by a water-cooling type press machine. A part of the sheet was pressure-molded at 260° C. for 6 minutes to give the film-like test piece having a thickness of 0.5 mm. The obtained sheet-like test piece was placed in an air oven of 150° C. with age and the days until it was embrittled was measured by a bending test. The obtained results are shown in Table 3.

TABLE 3

| Number | Light stabilizer | Days when embrittlement occurred at 150° C. (hrs) |
| --- | --- | --- |
| 1 | SANOL LS-770 | 5 |
| 2 | Compound of Formula (5-1) | 14 |
| 3 | Compound of Formula (5-2) | 14 |
| 4 | Compound of Formula (5-3) | 14 |
| 5 | Compound of Formula (5-4) | 14 |
| 6 | Compound of Formula (5-5) | 14 |
| 7 | Compound of Formula (5-6) | 14 |
| 8 | Compound of Formula (5-7) | 14 |
| 9 | Compound of Formula (5-8) | 14 |
| 10 | Compound of Formula (5-29) | 13 |
| 11 | Compound of Formula (5-30) | 13 |
| 12 | Compound of Formula (5-24) | 13 |

As can be seen from Table 3, the compound of the present invention has an excellent improvement effect of heat resistance stability as compared with the comparative compound.

Example 34

Evaluation of Compatibility in Low Density Polyethylene Resin 0.30 part by weight of the compound obtained in Example as a light stabilizer or bis(2,2,6,6-tetramethyl-piperidyl)sebacate (trade name "SANOL LS-770", manufactured by Sankyo Life Tech Co., Ltd.) and tetrakis(2,2,6,6-tetramethyl-4-piperidyl)-1,2,3,4-butanetetracarboxylate (trade name "Adekastab LA-57", manufactured by Asahi Denka Inc.), i.e., light stabilizers as Comparative example and 0.20 part by weight of octadecyl-3-(3,5-di-tert-butyl-4-hydroxyphenyl)propionate (trade name "IRGANOX 1076", manufactured by Ciba Specialty Chemicals, Inc.) as an antioxidant were mixed relative to 100 parts by weight of low density polyethylene (trade name "Suntech™ LD M2206", manufactured by Asahi Kasei Inc.) and after the mixture was kneaded at 180° C. for 10 minutes using a labo plastomill (manufactured by Toyo Seiki Seisakusho Inc.), it was rolled to a sheet-like shape by a water-cooling type press machine. A part of the sheet was pressure-molded at 180° C. for 6 minutes to give the film-like test piece having a thickness of 0.5 mm. The obtained test piece was placed on a black base paper at room temperature with age and generation of bloom was measured in every week. The results are shown in Table 4.

TABLE 4

| Number | Light stabilizer | Period until generation of bloom (week) |
|---|---|---|
| 1 | SANOL LS-770 | <1 |
| 2 | Adekastab LA-57 | 7 |
| 3 | Compound of Formula (5-1) | >15 |
| 4 | Compound of Formula (5-6) | >15 |
| 5 | Compound of Formula (5-7) | >15 |
| 6 | Compound of Formula (5-8) | >15 |
| 7 | Compound of Formula (5-24) | >15 |

As can be seen from Table 4, a transferring property to a surface is improved since the period of generation of bloom of the compound of the present invention is longer as compaured with the comparative compound.

Example 35

Evaluation of Pigment Dispersibility in Polypropylene Resin 0.30 part by weigh of the compound obtained in Example as a light stabilizer or a condensation product of N,N'-bis(2,2,6,6-tetramethyl-4-piperidyl)hexamethylenediamine with 4-tert-octylamino-2,6-dichloro-1,3,5-s-triazine (trade name "CHIMASSORB 944", manufactured by Ciba Specialty Chemicals, Inc.) and 1,2,2,6,6-pentamethyl-4-piperidyl/β,β,β',β'-tetramethyl-3,9-[2,4,8,10-tetraoxospiro[5.5]undecan]diethyl(mixing)-1,2,3,4-butanetetracarboxylate (trade name "Adekastab LA-63", manufactured by Asahi Denka Inc.), i.e., a light stabilizer as the Comparative example, 0.10 part by weight of pentaerythrityl-tetrakis-3-(3,5-di-tert-butyl-4-hydroxyphenyl)propionate (trade name "IRGANOX 1010", manufactured by Ciba Specialty Chemicals, Inc.) as an antioxidant, 0.10 part by weight of calcium stearate and 0.30 part by weight of CROMOPHTAL Red BRN as a pigment were mixed relative to 100 parts by weight of unstabilized polypropylene (trade name "Mitsui Polypro™ J105P", manufactured by Mitsui Kagaku Co., Ltd.) and after the mixture was kneaded at 200° C. for 10 minutes using a labo plastomill (manufactured by Toyo Seiki Seisakusho, Inc.), it was rolled to a sheet-like shape by a water-cooling type press machine. A part of the sheet was pressure-molded at 260° C. for 6 minutes to give the film-like test piece having a thickness of 0.15 mm. An influence of the light stability relative to the pigment dispersibility was investigated by measuring color difference of the obtained test piece by a spectrocolorimeter. The results are shown in Table 5. Further, the dispersibility of the pigment particles was made to ○ when the color difference is less than 5.0 and to x when the color difference is 5.0 or more as compared with the case of non-addition.

(1) spectrocolorimeter: manufactured by MINOLTA, CM-3700d

TABLE 5

| Number | Light stabilizer | Dispersibility of pigment | Color difference (difference with initial value) |
|---|---|---|---|
| 1 | Non-addition | ○ | 0 (Initial value) |
| 2 | CHIMASSORB 944 | x | 10.1 |
| 3 | Adekastab LA-63 | x | 8.3 |
| 4 | Compound of Formula (5-1) | ○ | 2.6 |
| 5 | Compound of Formula (5-2) | ○ | 4.9 |
| 6 | Compound of Formula (5-8) | ○ | 1.6 |
| 7 | Compound of Formula (5-29) | ○ | 2.7 |
| 8 | Compound of Formula (5-30) | ○ | 0.7 |
| 9 | Compound of Formula (5-24) | ○ | 0.8 |

As can be seen from Table 5, the compound of the present invention has a characteristic not affecting on the pigment dispersibility as compared with the case of comparative compound.

Example 36

Evaluation of Volatility by Heat

The compound obtained in Example or bis(2,2,6,6-tetramethyl-piperidyl)sebacate (trade name "SANOL LS-770" manufactured by Sankyo Life Tech CO., Ltd) and tetrakis(1,2,2,6,6-pentamethyl-4-piperidyl)-1,2,3,4-butanetetracarboxylate (trade name "Adekastab LA-52", manufactured by Asahi Denka Inc.), i.e., a light stabilizer as the Comparative example were weighed in an aluminum vessel by approximately 5 mg. The mixture was placed in a thermal analysis apparatus and the temperature was raised from room temperature by 5° C. per minutes while introducing air to the thermal analysis apparatus in 50 ml per 1 minutes. The volatility of the compound by high temperature processing was evaluated by measuring the weight remaining ratio at 300° C. of each sample. The obtained results are shown in Table 6.

(1) Thermal analysis apparatus: manufactured by Bulkar AXS Inc., TG-DTA2000S

TABLE 6

| Number | Light stabilizer | Weight remaining ratio (%) |
|---|---|---|
| 1 | SANOL LS-770 | 33.9 |
| 2 | Adekastab LA-52 | 70.9 |
| 3 | Compound of Formula (5-1) | 94.3 |
| 4 | Compound of Formula (5-2) | 94.1 |
| 5 | Compound of Formula (5-3) | 96.1 |
| 6 | Compound of Formula (5-4) | 93.3 |
| 7 | Compound of Formula (5-5) | 95.0 |
| 8 | Compound of Formula (5-6) | 91.5 |
| 9 | Compound of Formula (5-7) | 94.9 |
| 10 | Compound of Formula (5-8) | 94.5 |
| 11 | Compound of Formula (5-29) | 92.3 |
| 12 | Compound of Formula (5-30) | 95.6 |
| 13 | Compound of Formula (5-24) | 91.4 |

As can be seen from Table 6, the compound of the present invention has an excellent improvement effect of anti-volatility as compared with the comparative compound.

Example 37

Evaluation-1 of Weather Resistance in Pigment System Polypropylene Resin 0.10 part by weigh of the compound obtained in Example as a light stabilizer or a condensation product of N,N'-bis(2,2,6,6-tetramethyl-4-piperidyl)hexamethylenediamine with 4-tert-octylamino-2,6-dichloro-1,3,5-s-triazine (trade name "CHIMASSORB 944", manufactured by Ciba Specialty Chemicals, Inc.) and 1,8-bis-N-(2,4-bis(N-(2,2,6,6-tetramethyl-4-piperidyl)butylamino)-1,3,5-triazin-6-yl)amino-4-N-(2,4-bis(N-(2,2,6,6-tetramethyl-4-piperidyl)butylamino)-1,3,5-triazin-6-yl)aminomethyloctane (a compound in Example 1 (exemplary compound No. 7) of Japanese Unexamined Patent Publication No. Sho 59-122487), i.e., a light stabilizer shown in Table 7 as the Comparative example, 0.10 part by weight of pentaerythrityl-tetrakis-3-(3,5-di-tert-butyl-4-hydroxyphenyl)propionate (trade name "IRGANOX 1010", manufactured by Ciba Specialty Chemicals, Inc.) and tris(2,4-di-tert-butylphenyl)phosphite (trade name "IRGAFOS 168", manufactured by Ciba Specialty Chemicals Inc.) as an anti-oxidant, 0.10 part by weight of calcium stearate and 20 part by weight of talc relative to 100 parts by weight of unstabilized polypropylene (trade name "Mitsui Polypro™ J707P", manufactured by Mitsui Kagaku Co., Ltd.) were uniformly mixed in a V type mixer. The obtained mixture was granulated in a biaxial extruder, the pigment was added to the granulated article and the mixture was molded to a flat plate of 2 mm×50 mm×70 mm by an injection molding machine. Those samples were exposed into a xenon wetherometer and periodically taken out and the crack generation time was obtained by observing the surface by a microscope (magnification: 200 times). The obtained results are shown in Table 7.

(1) Apparatus model used in exposure test: manufactured by Atlas Inc., xenon wetherometer Ci4000, water spray 18 minutes/120 minutes, black panel temperature: 83±3° C.

TABLE 7

| Number | Light stabilizer | Crack generation time (hrs) |
| --- | --- | --- |
| 1 | Non-addition | 300 |
| 2 | CHIMASSORB 944 | 1800 |
| 3 | Compound described in Japanese Unexamined Patent Publication No. Sho 59-122487 | 2000 |
| 4 | Compound of Formula (5-4) | 2800 |
| 5 | Compound of Formula (5-5) | 3000 |
| 6 | Compound of Formula (5-6) | 2800 |
| 7 | Compound of Formula (5-7) | 2400 |
| 8 | Compound of Formula (5-8) | 2800 |
| 9 | Compound of Formula (5-19) | 2600 |

As can be seen from Table 7, the compound of the present invention has an excellent improvement effect of weather resistance stability as compared with the comparative compound.

Example 38

Evaluation-2 of Weather Resistance in Pigment System Polypropylene Resin 0.20 part by weigh of the compound obtained in Example as a light stabilizer or a condensation product of N,N'-bis(2,2,6,6-tetramethyl-4-piperidyl)hexamethylenediamine with 4-tert-octylamino-2,6-dichloro-1,3,5-s-triazine (trade name "CHIMASSORB 944", manufactured by Ciba Specialty Chemicals, Inc.), N,N',N'',N'-tetrakis(4,6-bis(butyl-(N-methyl-2,2,6,6-tetramethyl-4-piperidyl)amino)-triazin-2-yl)-4,7-diazadecane-1,1,0-diamine (trade name "CHIMASSORB 944", manufactured by Ciba Specialty Chemicals Inc.), tetrakis (1,2,2,6,6-pentamethyl-4-piperidyl)-1,2,3,4-butanetetracarboxylate (trade name "Adekastab LA-52", manufactured by Asahi Denka Inc.), 1,8-bis-N-(2,4-bis(N-(2,2,6,6-tetramethyl-4-piperidyl)butylamino)-1,3,5-triazin-6-yl)amino-4-N-(2,4-bis(N-(2,2,6,6-tetramethyl-4-piperidyl)butylamino)-1,3,5-triazin-6-yl)aminomethyloctane (a compound in Example 1 (exemplary compound No.: 7) of Japanese Unexamined Patent Publication No. Sho 59-122487), i.e., a light stabilizer shown in Table 8 as the Comparative example, 0.10 part by weight of pentaerythrityl-tetrakis-3-(3,5-di-tert-butyl-4-hydroxyphenyl)propionate (trade name "IRGANOX 1010", manufactured by Ciba Specialty Chemicals, Inc.) and tris(2,4-di-tert-butylphenyl)phosphite (trade name "IRGAFOS 168", manufactured by Ciba Specialty Chemicals Inc.) as an anti-oxidant, 0.10 part by weight of calcium stearate and 20 part by weight of talc relative to 100 parts by weight of unstabilized polypropylene (trade name "Mitsui Polypro™ J707P", manufactured by Mitsui Kagaku Co., Ltd.) were uniformly mixed in a V type mixer. The obtained mixture was granulated in a biaxial extruder, the pigment was added to the granulated article and the mixture was molded to a flat plate of 2 mm×50 mm×70 mm by an injection molding machine. Those samples were exposed into a xenon wetherometer and periodically taken out and the crack generation time was obtained by observing the surface by a microscope (magnification: 200 times). The obtained results are shown in Table 8.

(1) Apparatus model used in exposure test: manufactured by Diepla Wintes Inc., metal wether KU-R5CI-W, light irradiation/dark cycle, black panel temperature: 83±3° C.

TABLE 8

| Number | Light stabilizer | Deterioration time (hrs) |
| --- | --- | --- |
| 1 | Non-addition | 24 |
| 2 | CHIMASSORB 944 | 192 |
| 3 | CHIMASSORB 119 | 264 |
| 4 | ADEKASTAB LA-52 | 288 |
| 5 | Japanese Unexamined Patent Publication No. Sho 59-122487 compound | 264 |
| 6 | Compound of Formula (5-4) | 456 |
| 7 | Compound of Formula (5-5) | 480 |
| 8 | Compound of Formula (5-6) | 480 |
| 9 | Compound of Formula (5-7) | 408 |
| 10 | Compound of Formula (5-8) | 480 |
| 11 | Compound of Formula (5-19) | 456 |

As can be seen from Table 8, the compound of the present invention has an excellent improvement effect of weather resistance stability as compared with the comparative compound.

All publications, patents and patent applications cited in the present specification are incorporated in the present specification as reference as such.

INDUSTRIAL APPLICABILITY

The compound of the present invention imparts the light stability to the organic material of both thin articles and thick articles without causing a problem of bleeding out, fogging, sick house, pigment low dispersibility, contamination of the metal die at molding. Further, the compound also stabilizes the organic material with respect to deterioration by light, heat, oxygen, ozone and electro-magnetic wave such as X ray and γ ray.

We claim:

1. A compound of formula (1)

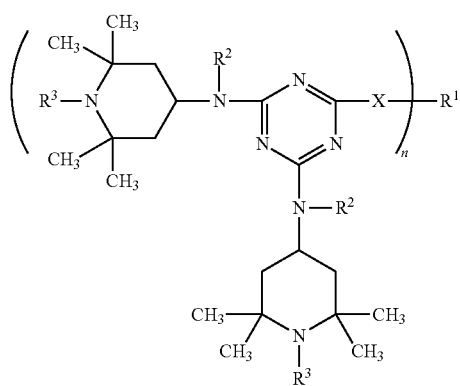

or a salt thereof, wherein
X is $(NR^4)$,
$R^1$ is a group of formula (2-2),

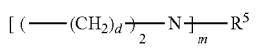

(2-2)

where
$R^5$ is a m-valent hydrocarbon,
m is an integer of from 2 to 8,
d is an integer of from 1 to 6,
$R^2$ is a hydrogen atom or an alkyl group having from 1 to 9 carbon atoms,
$R^3$ is a hydrogen atom, an alkyl group having from 1 to 9 carbon atoms, an alkoxy group having from 1 to 9 carbon atoms or an acyl group having from 2 to 9 carbon atoms,
$R^4$ is a hydrogen atom or an alkyl group having from 1 to 9 carbon atoms and
n is an integer of from 4 to 16.

2. A compound or its salt according to claim 1 where d is 3.

3. A compound or its salt according to claim 1 where $R^3$ is a hydrogen atom or a methyl group.

4. A compound of formula (5-8) to (5-23), (5-33) or (5-34) or a salt thereof

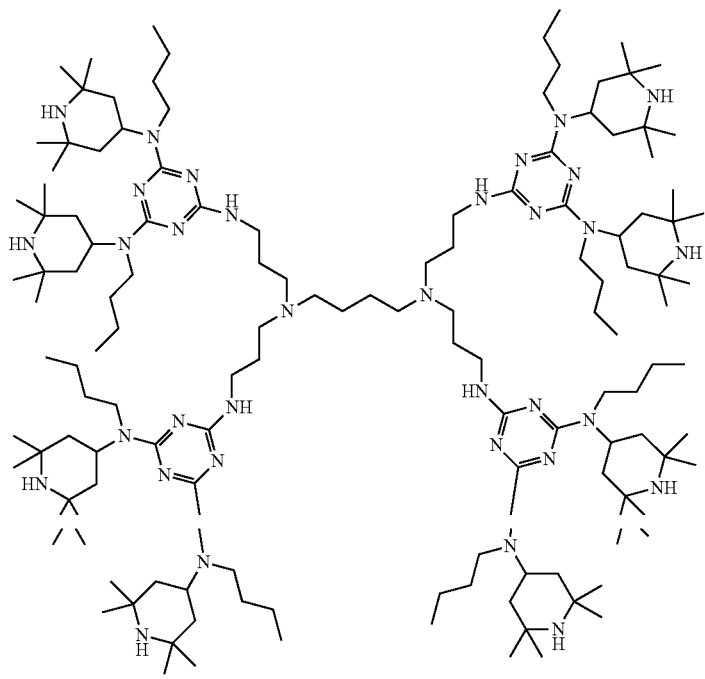

(5-8)

(5-9)
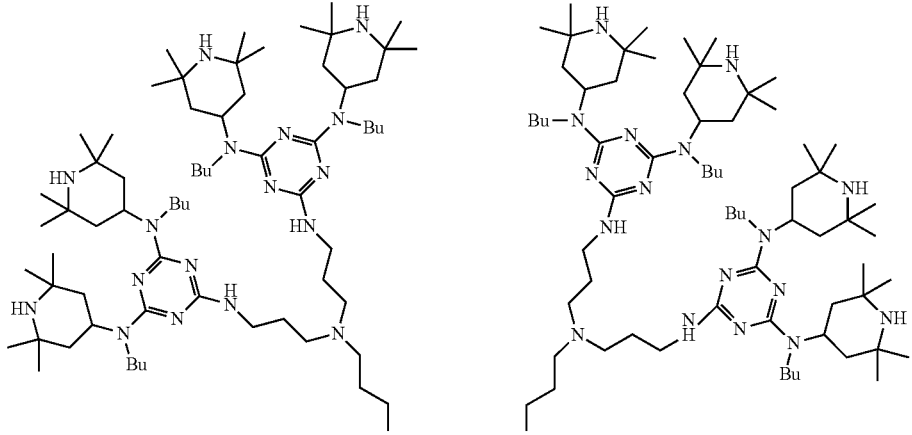
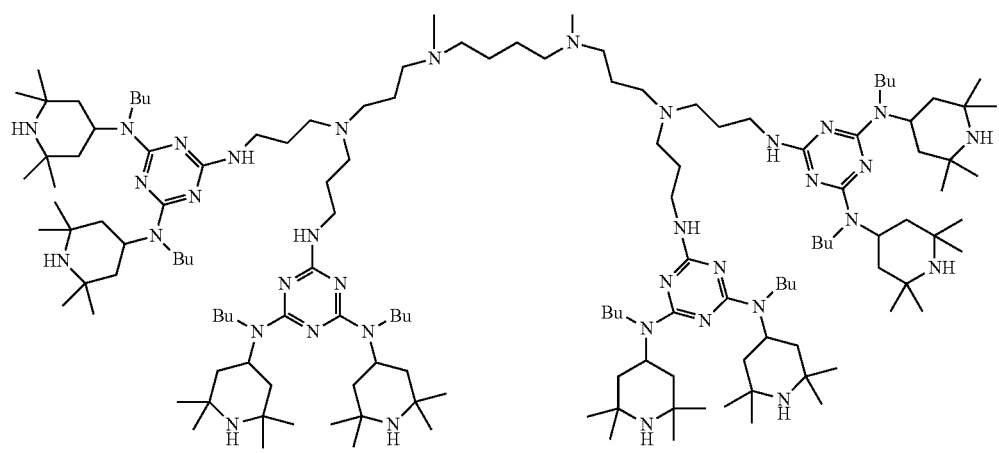
(5-10)
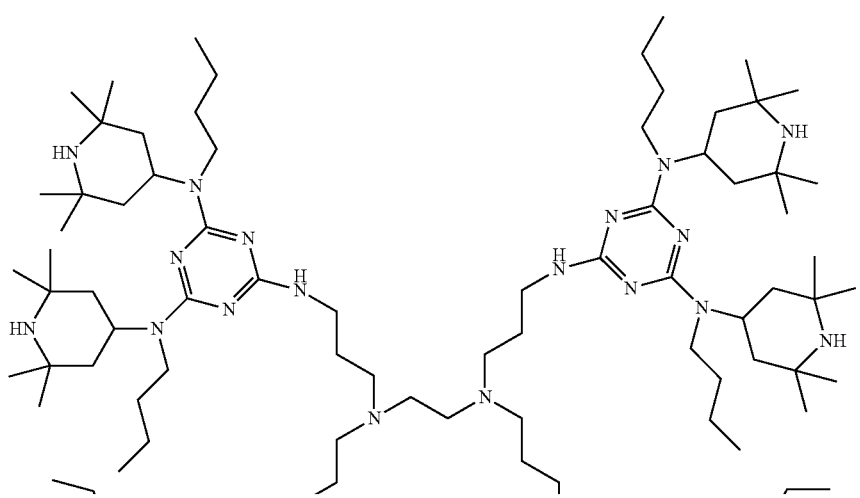

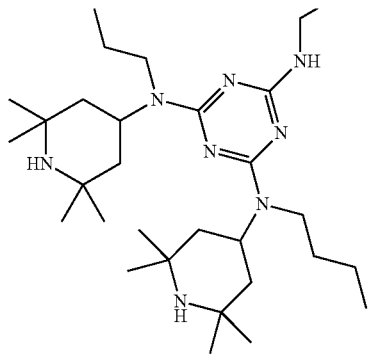 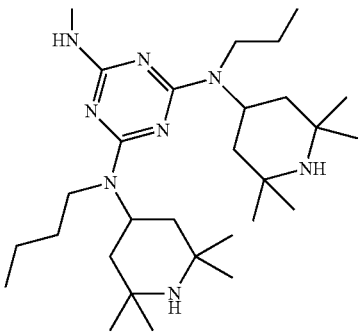
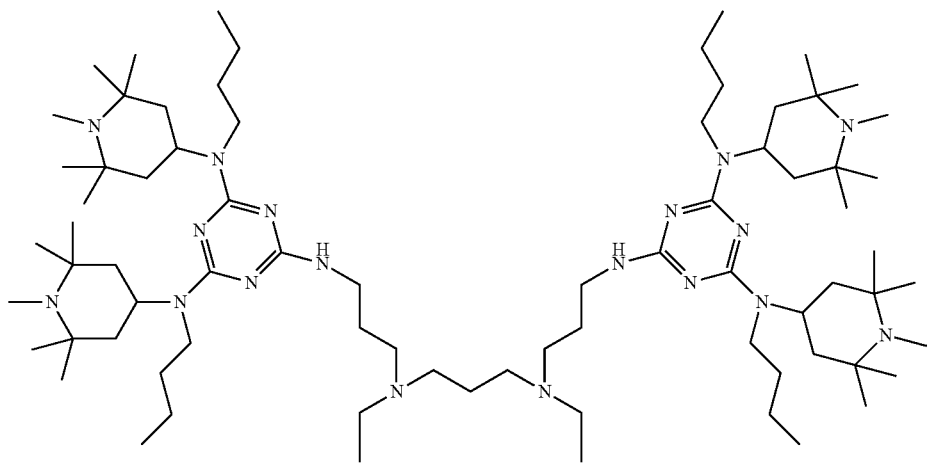
(5-11)
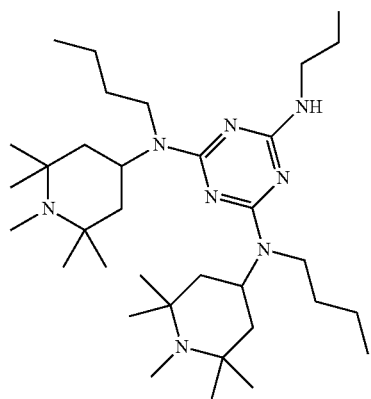 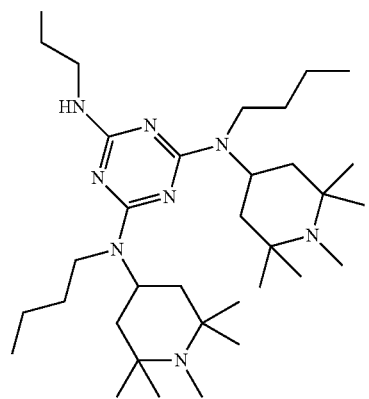

(5-12)
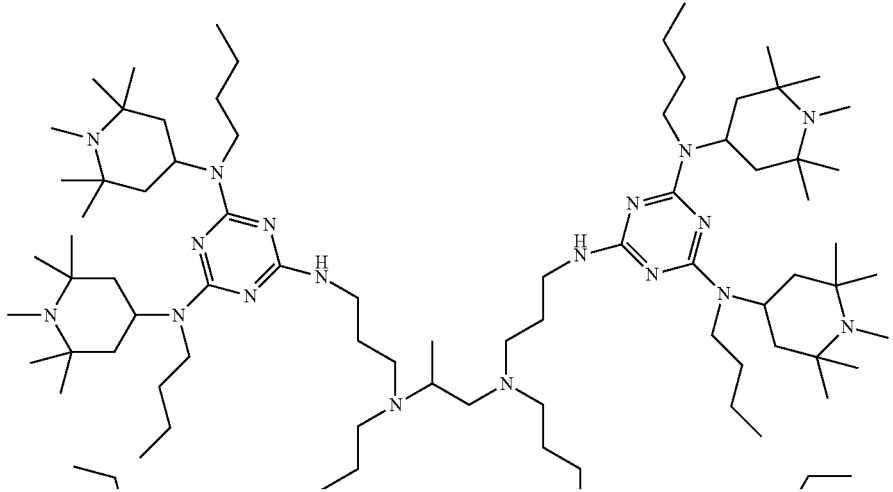
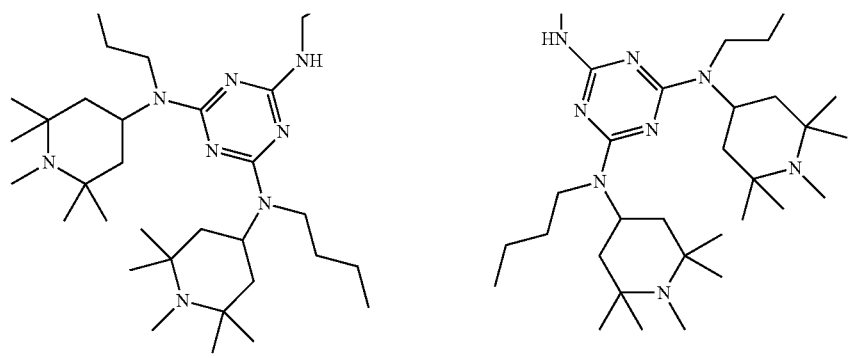
(5-13)
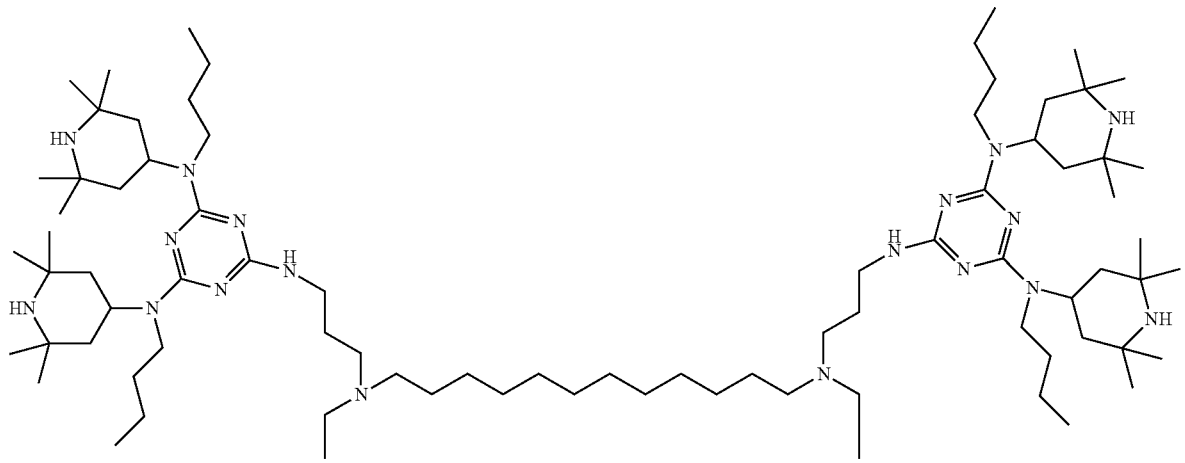

83 84
-continued
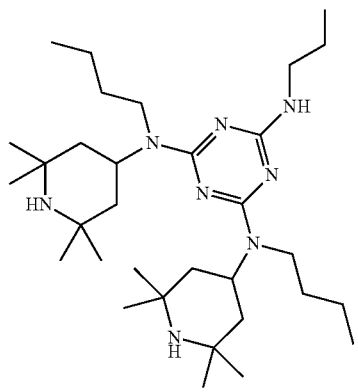
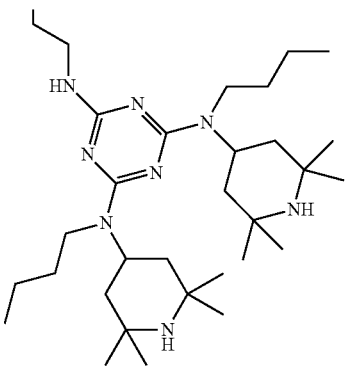
(5-14)
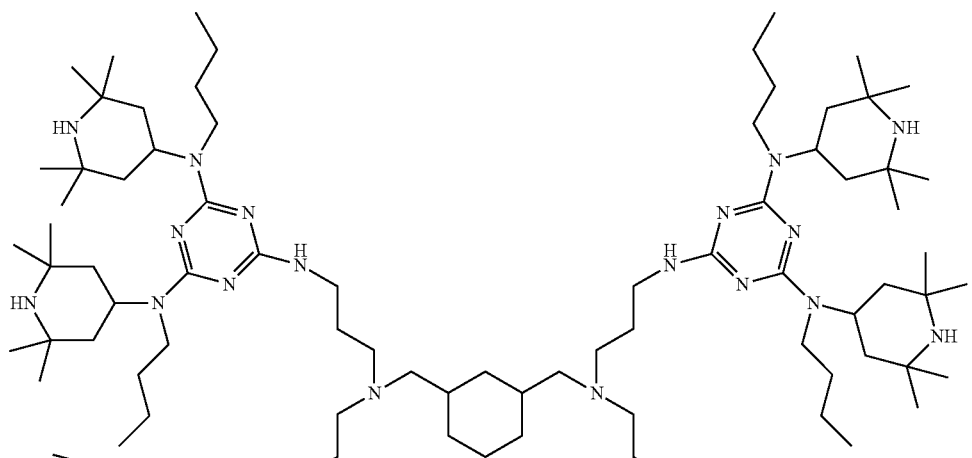
(5-15)
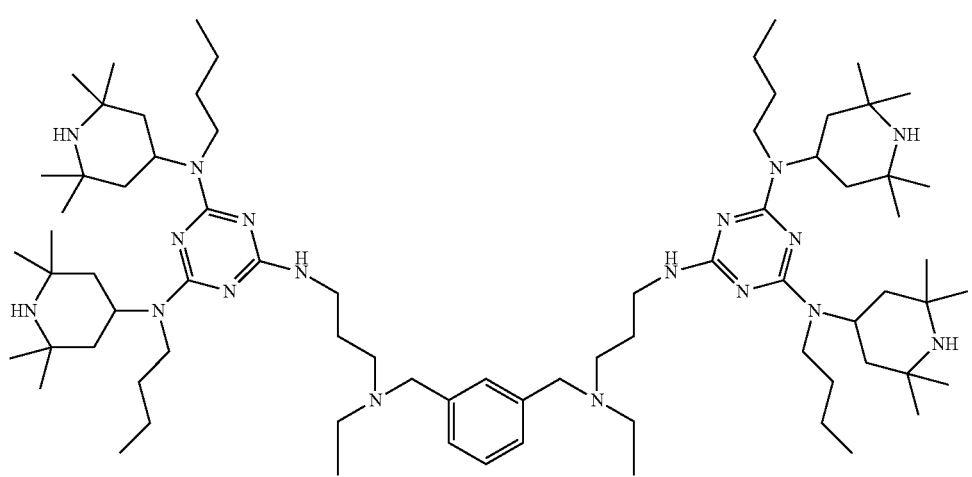

85 86
-continued
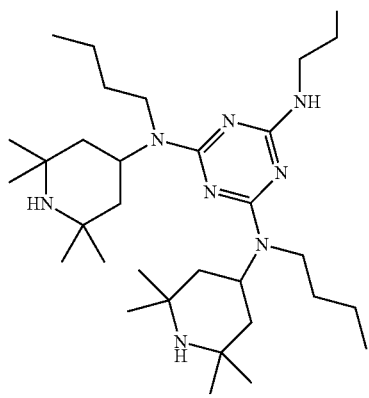
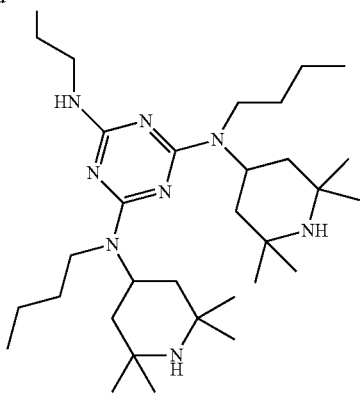
(5-16)
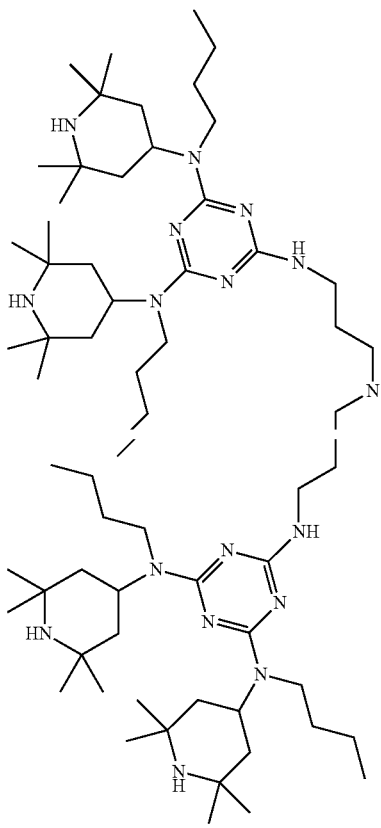
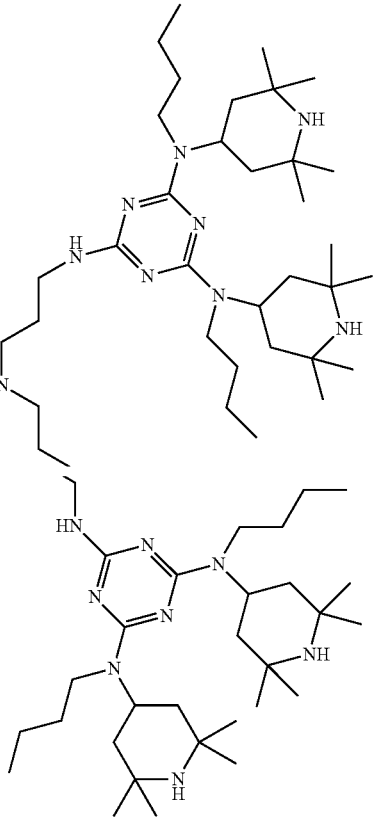
(5-17)
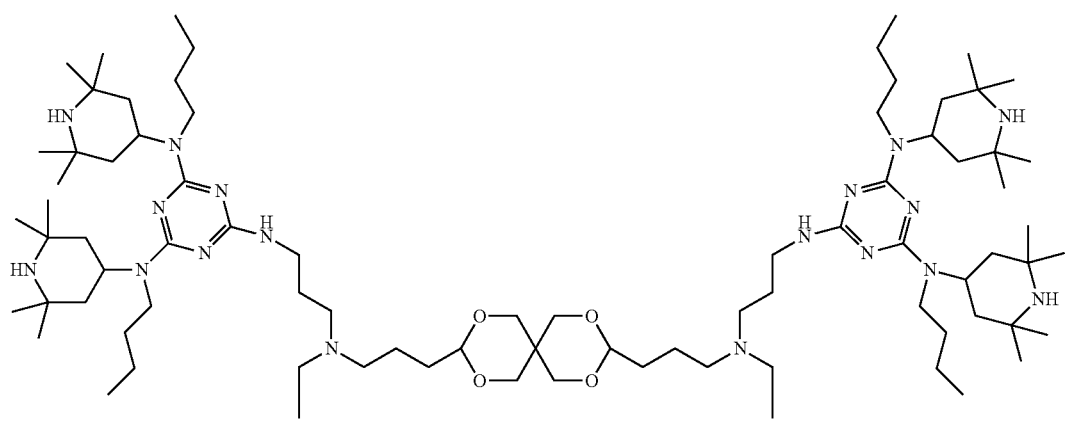

87   88
-continued
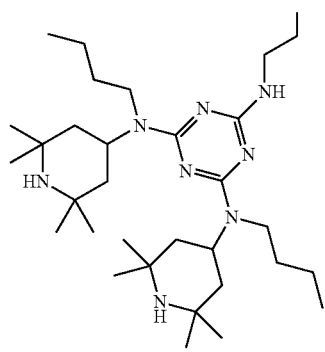
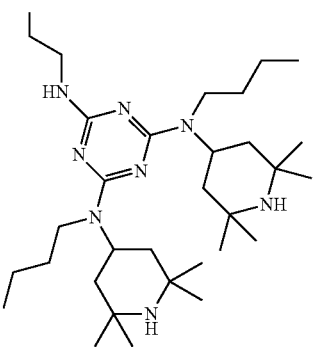
(5-18)
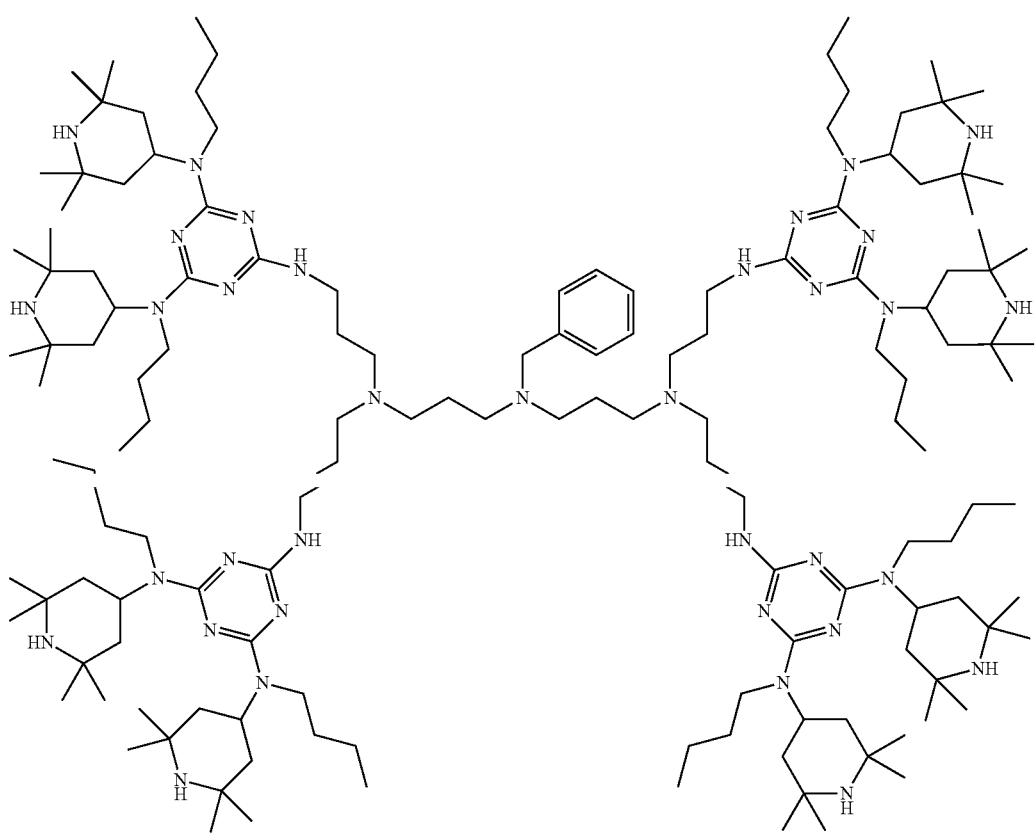
(5-19)
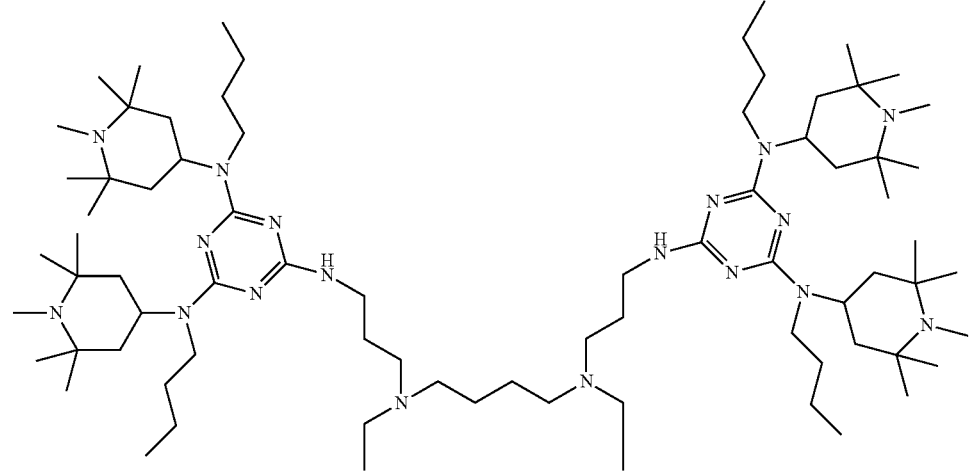

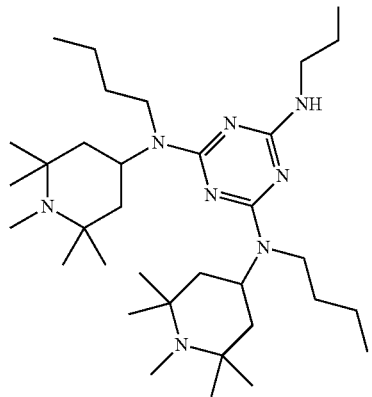
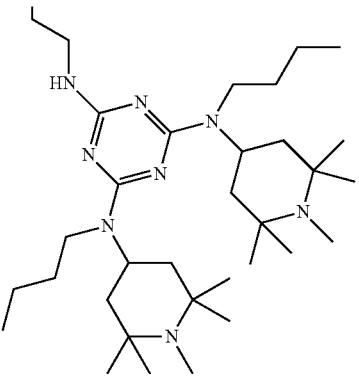
(5-20)
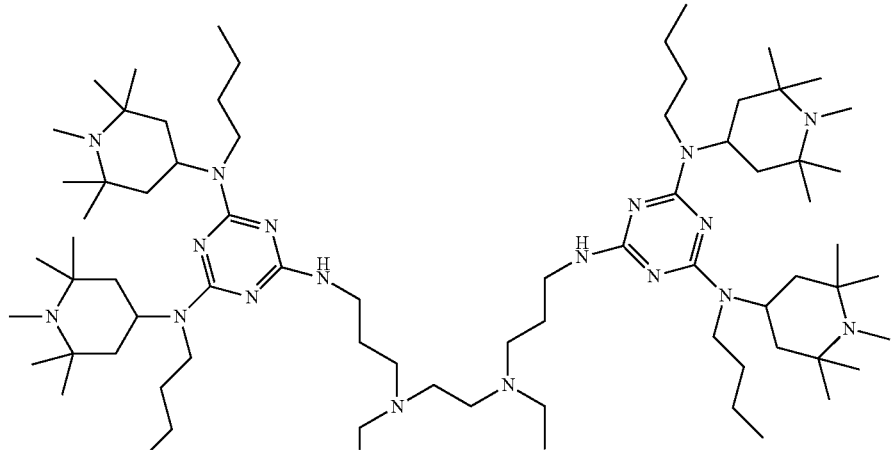
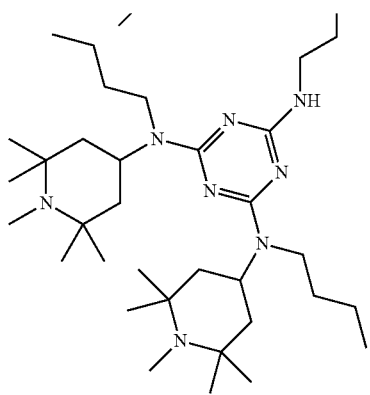
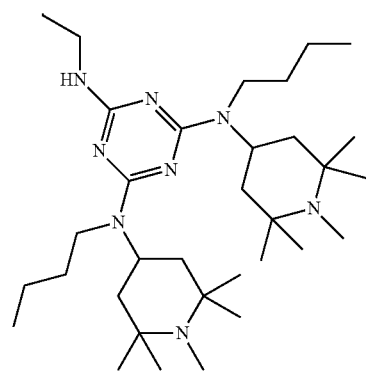

-continued
(5-21)
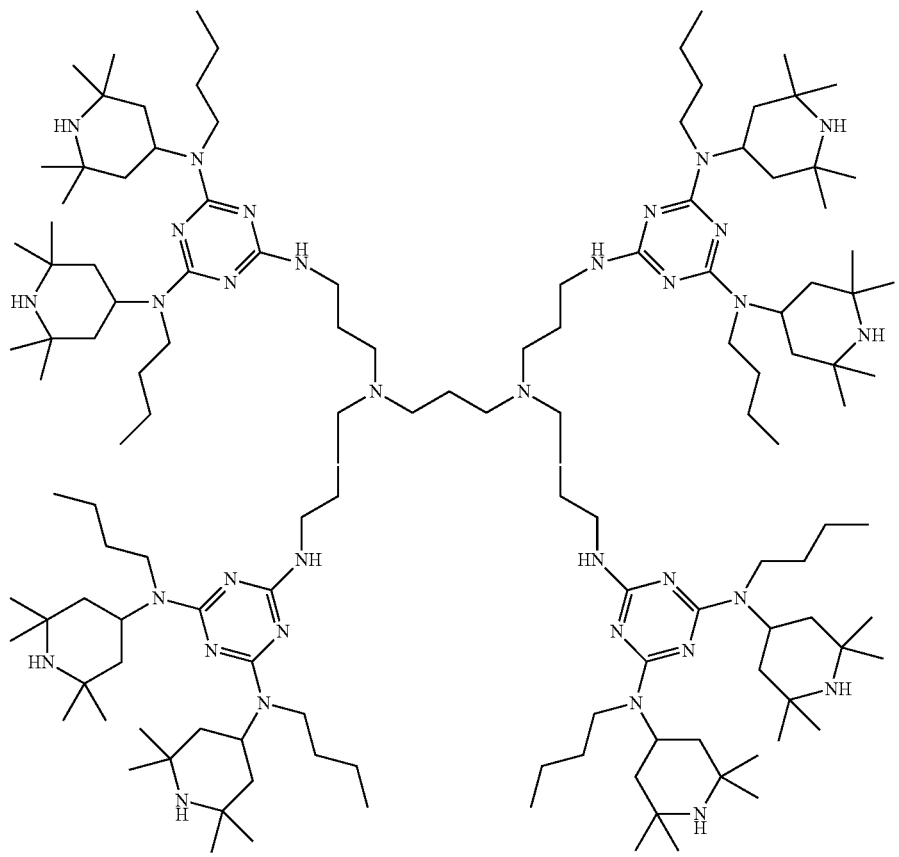
(5-22)
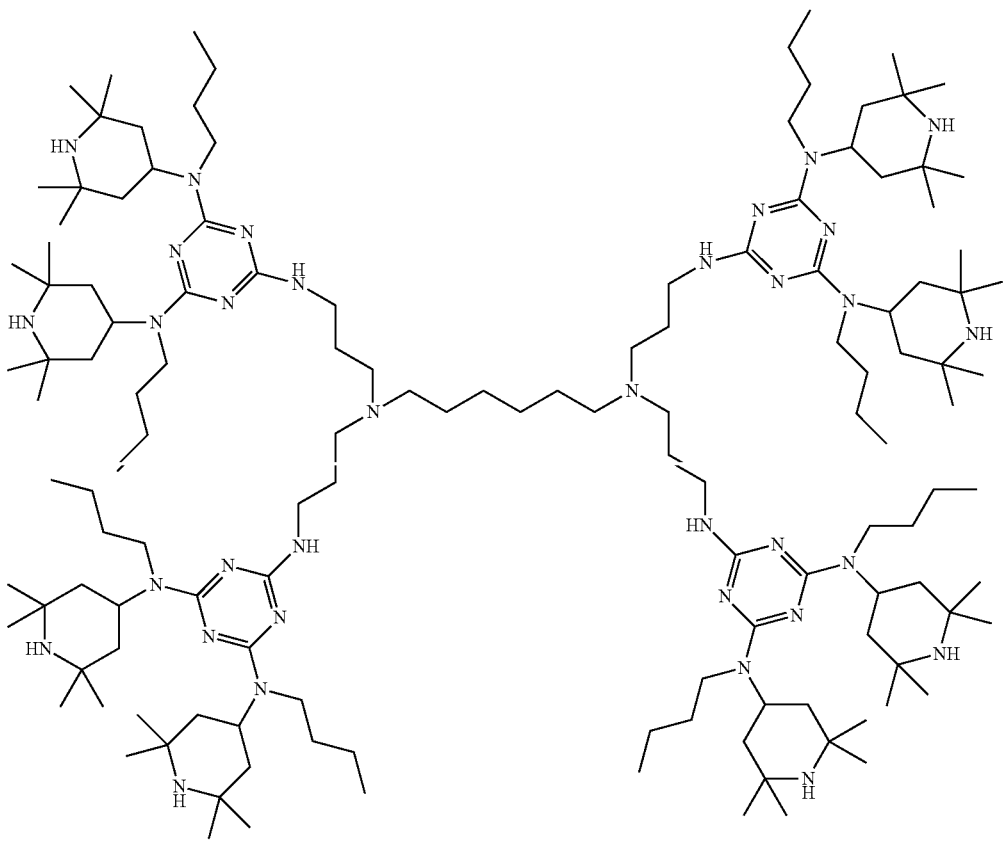

(5-23)
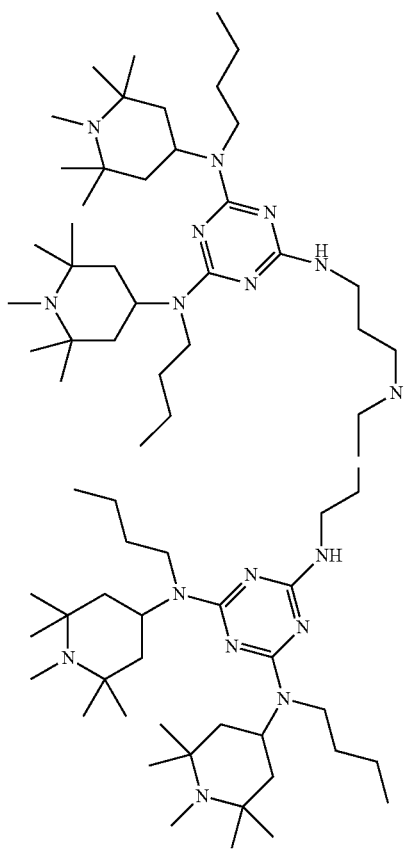
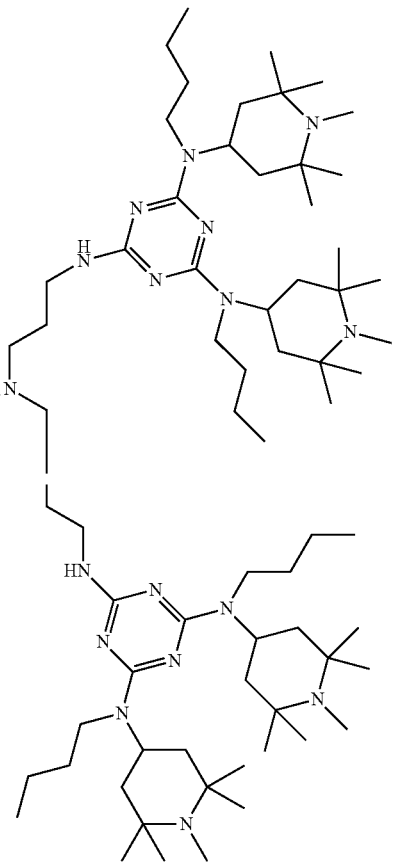
(5-33)
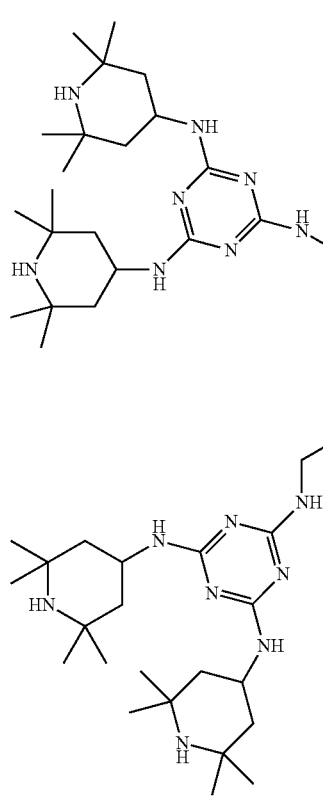
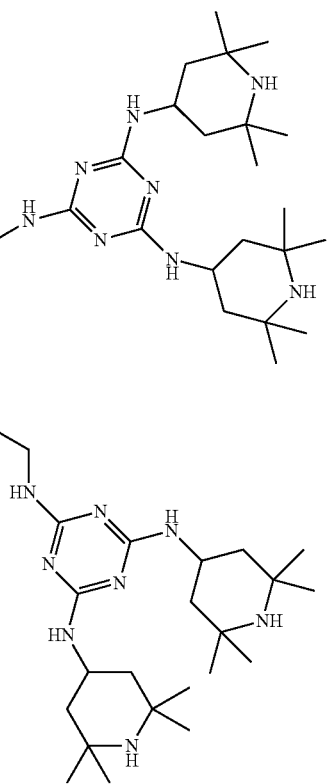

-continued
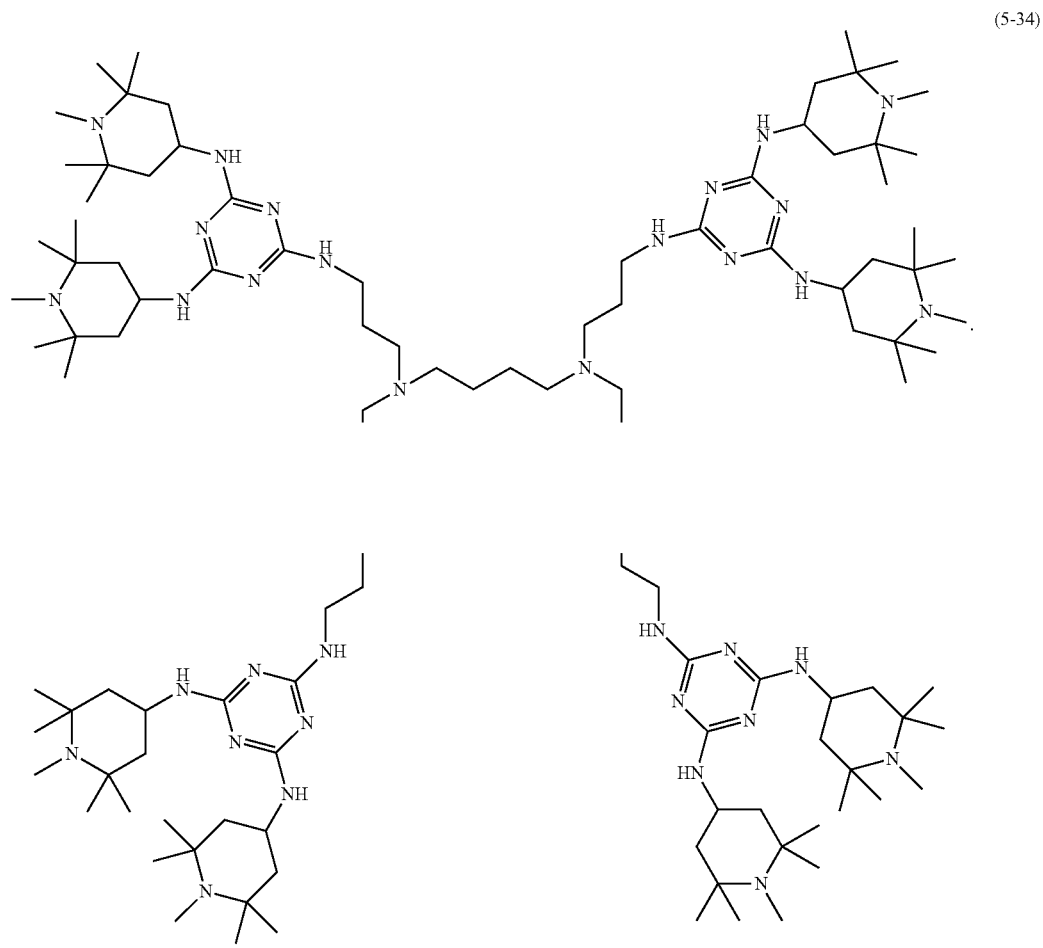
(5-34)
5. A process to prepare a compound of formula (1) according to claim 1
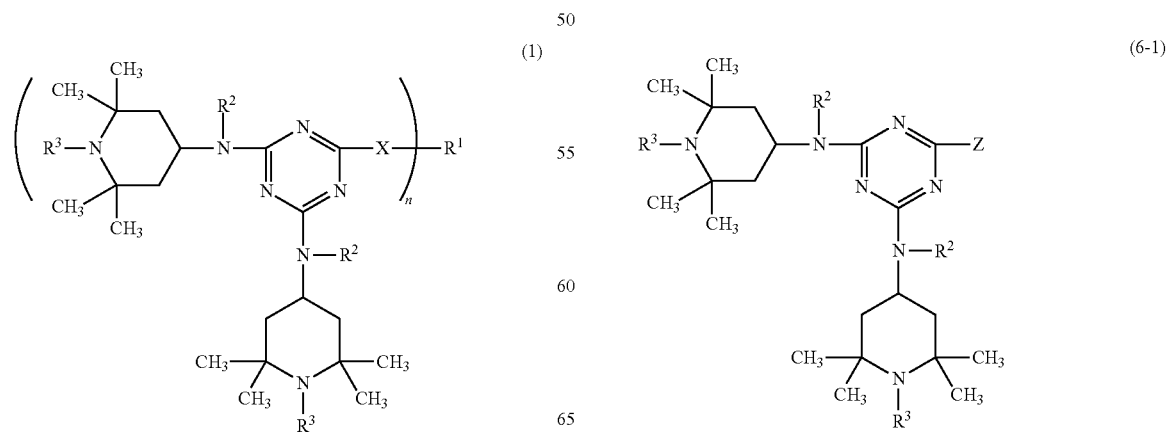
which process comprises coupling a compound of formula (6-1)

with a compound of formula (6-2)

$$R^1—(XH)_n \quad (6\text{-}2)$$

Where Z is a halogen atom and the other groups are defined as in claim 1.

6. A method for stabilizing an organic material relative to deterioration by light, heat, oxygen, ozone and/or an electromagnetic wave, comprising adding to the organic material a compound according to claim 1 or a salt thereof in an amount of from 0.001 to 15 parts by weight, relative to 100 parts by weight of the organic material.

7. An organic material composition in which at least one of the compounds of formula (1) according to claim 1 or at least one salt thereof are present in an amount of from 0.001 to 15 parts by weight, relative to 100 parts by weight of the organic material.

* * * * *